(12) United States Patent
Ray et al.

(10) Patent No.: US 7,598,049 B2
(45) Date of Patent: Oct. 6, 2009

(54) METHODS FOR DIAGNOSIS OF ALZHEIMER'S DISEASE IN BLOOD SAMPLES

(75) Inventors: Sandip Ray, San Francisco, CA (US); Anton Wyss-Coray, Belmont, CA (US)

(73) Assignees: Satoris, Inc., San Jose, CA (US); The Borad of Trustees of the Leland Stanford Junior University, Palo Alto, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 10/993,813

(22) Filed: Nov. 19, 2004

(65) Prior Publication Data

US 2005/0221348 A1 Oct. 6, 2005

(51) Int. Cl.
G01N 33/567 (2006.01)
G01N 33/48 (2006.01)
G01N 31/00 (2006.01)
A61B 5/00 (2006.01)

(52) U.S. Cl. .......................... 435/7.21; 702/19; 702/23; 600/300

(58) Field of Classification Search ........................ None
See application file for complete search history.

(56) References Cited

U.S. PATENT DOCUMENTS

| | | |
|---|---|---|
| 4,683,202 A | 7/1987 | Mullis |
| 4,728,605 A | 3/1988 | Fudenberg et al. |
| 5,874,312 A | 2/1999 | Sredni et al. |
| 6,027,896 A | 2/2000 | Roses et al. |
| 6,114,133 A | 9/2000 | Seubert et al. |
| 6,130,048 A | 10/2000 | Nixon |
| 6,183,971 B1 | 2/2001 | Sasada et al. |
| 6,210,895 B1 | 4/2001 | Schipper et al. |
| 6,251,639 B1 | 6/2001 | Kurn |
| 6,358,681 B2 | 3/2002 | Ginsberg et al. |
| 6,451,547 B1 | 9/2002 | Jackowski et al. |
| 6,461,831 B1 | 10/2002 | Small et al. |
| 6,465,195 B1 | 10/2002 | Holtzman et al. |
| 6,475,161 B2 | 11/2002 | Teicher et al. |
| 6,495,335 B2 | 12/2002 | Chojkier et al. |
| 6,692,918 B2 | 2/2004 | Kurn |
| 6,699,677 B1 | 3/2004 | Schall et al. |
| 2003/0064416 A1 | 4/2003 | Jackowski et al. |
| 2003/0119074 A1 | 6/2003 | Jackowski et al. |
| 2005/0255484 A1 | 11/2005 | Valkirs et al. |
| 2006/0094064 A1 | 5/2006 | Ray et al. |
| 2007/0037200 A1 | 2/2007 | Ray et al. |

FOREIGN PATENT DOCUMENTS

| | | |
|---|---|---|
| EP | 1 050 758 A1 | 11/2000 |
| WO | WO-02/44732 A2 | 6/2002 |
| WO | WO-02/44732 A3 | 6/2002 |
| WO | WO-2005/052592 A2 | 6/2005 |
| WO | WO-2005/052592 A3 | 6/2005 |
| WO | WO-2006/133423 A1 | 12/2006 |

OTHER PUBLICATIONS

Frey et al Neurochem Res. 2005, 30(12): 1501-10.*
D'Asxenzo Curr Opin Mol Ther. 2005, 7(6): 557-64.*
Thavasu et al J Immunol Methods. Aug. 30, 1992;153(1-2):115-24.*
Rikkert et al (Neth J Med. 2003, 61(3): 83-87.*
Ho et al Brain Research Reviews 48 (2005) 360-369.*
Takahama et al Clin Cancer Res 1999, 5(9): 2506-10.*
Brattström Lung Cancer, 2002, 37(1): 57-63.*
Langenfeld Carcinogenesis. 2003, 24(9): 1445-54.*
Mroczko et al Clin Chem Lab Med. 2001; 39(5): 374-9.*
Hsieh et al Proteomics. 2006, 6(10):3189-98.*
Cheung et al Nature Genetics, 2003, 33, 422-425.*
Cobb et al (2002) (Crit Care Med. Dec. 2002;30(12):2711-21.*
Chan E., et al Integrating Transcriptomics and Proteomics, Genomics and Proteomics.*
Tarkowski et al Acta Neurol Scand. 2001;103(3):166-74.*
Hoshikawa et al , Physiol Genomics 12: 209-219, 2003.*
Behan et al. Journal of the American Academy of Geriatrics Society, 18(10):792-797, 1970.*
Frank et al., Neurobiology of Aging, 24:521-536, 2003.*
Hasegawa et al., Gerontology, 46: 185-188, Jul./Aug. 2000.*
Blaber, S.I. et al. (Jan. 29, 2002). "Enzymatic Properties of Rat Myelencephalon-Specific Protease," *Biochemistry* 41(4):1165-1173.
Heese, K. et al. (2000). "Induction of Rat L-Phosphoserine Phosphatase by Amyloid-β (1-42) is Inhibited by Interleukin-11," *Neurosci Lett.* 288(1):37-40.
Huberman, M. et al. (1994). "Correlation of Cytokine Secretion by Mononuclear Cells of Alzheimer Patients and Their Disease Stage," *J. Neuroimmunol.* 52(2):147-152.
Patel, N.S. et al. (Mar. 11, 2005). "Inflammatory Cytokine Levels Correlate with Amyloid Load in Transgenic Mouse Models of Alzheimer's Disease," *J. Neuroinflammation* 2(1):9. (10 total pages).
Robakis, N.K. et al. (1991). "Expression of the Alzheimer's Amyloid Precursor in Brain Tissue and Effects of NGF and EGF on its Metabolism," *Clin. Neuropharmacol.* 14(Suppl. 1):S15-S23.
Xia, M. et al. (Jul. 1998). "Immunohistochemical Study of the β-Chemokine Receptors CCR3 and CCR5 and Their Ligands in Normal and Alzheimer's Disease Brains," *Am. J. Pathol.* 153(1):31-37.
Abraham, J.A. et al. (1986). "Human Basic Fibroblast Factor: Nucleotide Sequence and Genomic Organization," *EMBO J.* 5(10):2523-2528.

(Continued)

*Primary Examiner*—Olga N Chernyshev
*Assistant Examiner*—Stacey MacFarlane
(74) *Attorney, Agent, or Firm*—Morrison & Foerster LLP

(57) ABSTRACT

The inventors have discovered a collection of proteinaceous biomarkers ("AD biomarkers) which can be measured in peripheral biological fluid samples to aid in the diagnosis of neurodegenerative disorders, particularly Alzheimer's disease and mild cognitive impairment (MCI). The invention further provides methods of identifying candidate agents for the treatment of Alzheimer's disease by testing prospective agents for activity in modulating AD biomarker levels.

17 Claims, 4 Drawing Sheets

OTHER PUBLICATIONS

Collins, T. et al. (Aug. 22, 1985). "Cultured Human Endothelial Cells Express Platelet-Derived Growth Factor B Chain: cDNA Cloning and Structural Analysis," *Nature* 316(6030):748-750.

Docherty, A.J.P. et al. (Nov. 7, 1985). "Sequence of Human Tissue Inhibitor of Metalloproteinases and its Identity to Erythroid-Potentiating Activity," *Nature* 318(6041):66-69.

Foster, D.C. et al. (Dec. 1994). "Human Thrombopoietin: Gene Structure, cDNA Sequence, Expression, and Chromosomal Localization," *Proc. Natl. Acad. Sci. U.S.A.* 91(26):13023-13027.

Gasson, J.C. et al. (Jun. 27, 1985). "Molecular Characterization and Expression of the Gene Encoding Human Erythroid-Potentiating Activity," *Nature* 315(6022):768-771.

Gray, A. et al. (Jun. 23, 1983). "Nucleotide Sequence of Epidermal Growth Factor cDNA Predicts a 128,000-Molecular Weight Protein Precursor," *Nature* 303:722-725.

Gray, P.W. et al. (Dec. 20/27, 1984). "Cloning and Expression of cDNA for Human Lymphotoxin, a Lymphokine with Tumour Necrosis Activity," *Nature* 312(5996):721-724.

Hohn, A. et al. (Mar. 22, 1990). "Identification and Characterization of a Novel Member of the Nerve Growth Factor/Brain-Derived Neurotrophic Factor Family," *Nature* 344(6264):339-341.

Marics, I. et al. (Mar. 1989). "Characterization of the *HST*-related *FGF*.6 Gene, a New Member of the Fibroblast Growth Factor Gene Family," *Oncogene* 4(3):335-340.

Masuzaki, H. et al. (Jul. 1995). "Human *Obese* Gene Expression: Adipocyte-Specific Expression and Regional Differences in the Adipose Tissue," *Diabetes* 44(7):855-858.

Rosenthal, A. et al. (Sep. 1991). "Primary Structure and Biological Activity of Human Brain-Derived Neurotrophic Factor," *Endocrinology* 129(3):1289-1294.

Schall, T.J et al. (Apr. 20, 1990). "Molecular Cloning and Expression of a Receptor for Human Tumor Necrosis Factor," *Cell* 61(2):361-370.

Schall, T.J. et al. (Aug. 1, 1988). "A Human T Cell-Specific Molecule is a Member of a New Gene Family," *J. Immunol.* 141(3):1018-1025.

Stetler-Stevenson, W.G. et al. (Aug. 15, 1990). "Tissue Inhibitor of Metalloproteinases-2 (TIMP-2) mRNA Expression in Tumor Cell Lines and Human Tumor Tissues," *J. Biol. Chem.* 265(23):13933-13938.

Taga, T. et al. (Aug. 11, 1989). "Interleukin-6 Triggers the Association of Its Receptor With a Possible Signal Transducer, gp130," *Cell* 58(3):573-581.

ten Dijke, P. et al. (Jul. 1988). "Identification of Another Member of the Transforming Growth Factor Type β Gene Family," *Proc. Natl. Acad. Sci. U.S.A.* 85(13):4715-4719.

Walz, A. et al. (1991). "Formation and Biological Properties of Neutrophil Activating Peptide 2 (NAP-2)," *Chemotactic Cytokines*, pp. 39-46.

Wang, W. et al. (May 1998). "Molecular Cloning and Functional Characterization of Human MIP-1δ, a New C-C Chemokine Related to Mouse CCF-18 and C10," *J. Clin. Immunol.* 18(3):214-222.

Yang, Y.-C. et al. (Oct. 10, 1986). "Human IL-3 (Multi-CSF): Identification by Expression Cloning of a Novel Hematopoietic Growth Factor Related to Murine IL-3," *Cell* 47(1):3-10.

Yoshikawa, W. et al. (Mar. 15, 1999). "Characterization of Free α- and β-Chains of Recombinant Macrophage-Stimulating Protein," *Arch. Biochem. Biophys.* 363(2):356-360.

Yoshimura, T. et al. (Jul. 25, 1993). "Cloning, Sequencing, and Expression of Human Macrophage Stimulating Protein (MSP, MST1) Confirms MSP as a Member of the Family of Kringle Proteins and Locates the MSP Gene on Chromosome 3," *J. Biol. Chem.* 268(21):15461-15468.

Zsebo, K.M. et al. (Oct. 5, 1990). "Stem Cell Factor is Encoded at the *S/* Locus of the Mouse and is the Ligand for the c-*kit* Tyrosine Kinase Receptor," *Cell* 63(1):213-224.

Agrawal, R. et al. (May 1993). "Mining Association Rules Between Sets of Items in Large Databases," *Proc. of the 1993 ACM SIGMOD Conference on Management of Data*, Washington, D.C., pp. 207-216.

Burbach, G.J. et al. (Mar. 10, 2004). "Induction of Brain-Derived Neurotrophic Factor in Plaque-Associated Glial Cells of Aged APP23 Transgenic Mice," *J. Neurosci.* 24(1Q):2421-2430.

Citron, M. et al. (Jan. 1997). "Mutant Presenilins of Alzheimer's Disease Increase Production of 42-Residue Amyloid β-Protein in Both Transfected Cells and Transgenic Mice," *Nat. Med.* 3(1):67-72.

Fahnestock, M. et al. (2002). "Neurotrophic Factors and Alzheimer's Disease: Are we Focusing on the Wrong Molecule?," *J. Neural Transm.* (62 Suppl.):241-252.

Fiala, M. et al. (Jul. 1998). "Amyloid-β Induces Chemokine Secretion and Monocyte Migration Across a Human Blood-Brain Barrier Model," *Mol. Med.* 4(7):480-489.

Folstein, M.F. et al. (1975). "'Mini-Mental State': A Practical Method For Grading The Cognitive State of Patients for the Clinician," *J. Psychiat. Res.* 12:189-198.

Galasko, D. (Oct. 2001). "Biological Markers and the Treatment of Alzheimer's Disease," *Journal of Molecular Neuroscience* 17(2):119-125.

Gottardo, R. et al. (2003). "Statistical Analysis of Microarray Data: A Bayesian Approach," *Biostatistics* 4(4):597-620.

Hastie, T. et al. (2001). "Supervised Harvesting of Expression Trees," *Genome Biology* 2(1):research0003.1-0003.12.

Higgins, G.A. et al. (2003). "Transgenic Mouse Models of Alzheimer's Disease: Phenotype and Application," *Behav. Pharmacol.* 14(5-6):419-438.

Hohlfeld, R. et al. (2000). "The Neuroprotective Effect of Inflammation: Implications for the Therapy of Multiple Sclerosis," *J. Neuroimmunol.* 107:161-166.

International Search Report mailed Aug. 3, 2005 for PCT Application No. PCT/US2004/039275 filed Nov. 19, 2004, 3 pages.

Kohonen, T. (Jan. 1982). "Self-Organized Formation of Topologically Correct Feature Maps," *Biological Cybernetics* 43(1):59-69.

Li, X.-L. et al. (Sep. 2, 2002). "Impairment of Long-term Potentiation and Spatial Memory in Leptin Receptor-Deficient Rodents," *Neuroscience* 113(3):607-615.

Masliah, E. et al. (Jul./Aug. 1995). "PDGF is Associated with Neuronal and Glial Alterations of Alzheimer's Disease," *Neurobiol. Aging* 16(4):549-556.

Oddo, S. et al. (Jul. 31, 2003). "Triple-Transgenic Model of Alzheimer's Disease with Plaques and Tangles: Intracellular Aβ and Synaptic Dysfunction," *Neuron* 39(3):409-421.

Power, D.A. et al. (Mar.-Apr. 2001). "Circulating Leptin Levels and Weight Loss in Alzheimer's Disease Patients," *Dement. Geriatr. Cogn. Disord.* 12(2):167-170.

R&D Systems, Inc. (Jun. 18, 2003). "Quantikine® HS: Human G-CSF Immunoassay, Catalog Nunmber HSCSO," located at http://archive.org/web/20030618210843/http://www.rndsystems.com/asp/c_search.asp?anyall=1&keywords=Quanitkine+HS, last visited on Mar. 16, 2005, 16 pages.

Sanna, V. et al. (Jan. 2003). "Leptin Surge Precedes Onset of Autoimmune Encephalomyelitis and Correlates with Development of Pathogenic T Cell Responses," *The Journal of Clinical Investigation* 111(2):241-250.

Tusher, V.G. et al. (Apr. 24, 2001). "Significant Analysis of Microarrays Applied to the Ionizing Radiation Response," *Proc. Natl. Acad. Sci. U.S.A.* 98(9):5116-5121.

International Search Report mailed Oct. 6, 2006 for PCT Application No. PCT/US06/22561 filed Jun. 8, 2006, 4 pages.

Kopp, R. et al. (Oct. 2003). "Reduced Survival of Rectal Cancer Patients With Increased Tumor Epidermal Growth Factor Receptor Levels," *Dis. Colon Rectum.* 46(10):1391-1399.

Lim, H.S. et al. (2005, Available Online Dec. 21, 2004). "Angiopoietin-1 and Angiopoietin-2 in Diabetes Mellitus: Relationship to VEGF, Glycaemic Control, Endothelial Damage/Dysfunction and Atherosclerosis," *Artherosclerosis* 180(1):113-118.

Thøgersen, V.B. et al. (Aug. 15, 2001). "A Subclass of HER1 Ligands are Prognostic Markers for Survival in Bladder Cancer Patients," *Cancer Res.* 61(16):6227-6233.

Bertram, L. et al. (Jan. 2007). "Systematic Meta-analyses of Alzheimer Disease Genetic Association Studies: The AlzGene Database," *Nature Genetics* 39(1):17-23 + 76 supplemental pages.

Ray, S. et al. (Manuscript submitted Sep. 26, 2006). "Early Alzheimer's Disease Defined by Patterns of Cellular Communication Factors in Plasma," *Nature*, 17 pages.

Allsop, D. et al. (Apr. 1988). "Immunohistochemical Evidence for the Derivation of a Peptide Ligand from the Amyloid β-Protein Precursor of Alzheimer Disease," *Proc. Natl. Acad. Sci. USA* 85:2790-2794.

Araujo, D.M. et al. (1990). "Potential Neurotrophic Factors in the Mammalian Central Nervous System: Functional Significance in the Developing and Aging Brain," *Int. Rev. Neurobiol.* 32:141-174.

Araujo, D.M. et al. (Aug. 1994). "Induction of Immune System Mediators in the Hippocampal Formation in Alzheimer's and Parkinson's Diseases: Selective Effects on Specific Interleukins and Interleukin Receptors," *Neuroscience* 61(4)745-754.

Baskin, F. et al. (May 1, 1997). "Altered Apolipoprotein E Secretion in Cytokine Treated Human Astrocyte Cultures," *J. Neurol. Sci.* 148(1):15-18.

Birecree, E. et al. (Jun. 21, 1991). "Epidermal Growth Factor and Its Receptor in the Developing Human Nervous System," *Dev. Brain Res.* 60(2):145-154.

Bright, J.J. et al. (Jan. 15, 2004). "Signaling Through JAK2-STAT5 Pathway Is Essential for IL-3-Induced Activation of Microglia," *Glia* 45(2):188-196.

Bright, J.J. et al. (Sep. 2004, e-pub. Jul. 20, 2004). "Signaling Through JAK2-STAT5 Pathway Is Essential for IL-3-Induced Activation of Microglia," Erratum, *Glia* 47(4):387.

Canet-Aviles, R-M. et al. (Jun. 15, 2002). "Muscarine Enhances Soluble Amyloid Precursor Protein Secretion in Human Neuroblastoma SH-SY5Y by a Pathway Dependent on Protein Kinase $C_a$, Src-Tyrosine Kinase and Extracellular Signal-Regulated Kinase But Not Phospholipase C," *Brain Res. Mol. Brain Res.* 102:62-72.

Cheng, B. et al. (Aug. 1992). "Glucose Deprivation Elicits Neurofibillary Tangle-like Antigenic Changes in Hippocampal Neurons: Prevention by NGF and bFGF," *Exp. Neurol.* 117(2):114-123.

Cosgaya, J.M. et al. (Jul. 1996). "Nerve Growth Factor and Ras Regulate β-Amyloid Precursor Protein Gene Expression in PC12 Cells," *J. Neurochem.* 67(1):98-104.

Ebadi, M. et al. (Apr.-May 1997). "Neurotrophins and Their Receptors in Nerve Injury and Repair," *Neurochem. Int.* 30(4-5):347-374.

Ekinci, F.J. et al. (Oct. 15, 1999). "Activation of the L Voltage-sensitive Calcium Channel by Mitogen-activated Protein (MAP) Kinase following Exposure of Neuronal Cells to β-Amyloid: MAP Kinase Mediates β-Amyloid-Induced Neurodegeneration," *J. Biol. Chem.* 274(42):30322-30327.

Fisher, A. et al. (Aug.-Oct. 2002). "AF150(S) and AF267B: M1 Muscarinic Agonists as Innovative Therapies for Alzheimer's Disease," *J. Mol. Neurosci.* 19(1-2):145-153.

Gray, C.W. et al. (Jun. 1993). "Induction of β-Amyloid Precursor Protein Isoform mRNAs by bFGF in Astrocytes," *Neuroreport* 4(6):811-814.

Hashimoto, Y. et al. (Sep. 2003). "The Cytoplasmic Domain of Alzheimer's Amyloid-β Protein Precursor Causes Sustained Apoptosis Signal-Regulating Kinase 1/c-Jun $NH_2$-Terminal Kinase-Mediated Neurotoxic Signal via Dimerization," *J. Pharmacol. Exp. Ther.* 306(3):889-902.

Hays, S.J. (Aug. 1998). "Therapeutic Approaches to the Treatment of Neuroinflammatory Diseases," *Curr. Pharm. Des.* 4(4):335-348.

Hoffer, B. et al. (1997). "Treatment Strategies for Neurodegenerative Diseases Based on Trophic Factors and Cell Transplantation Techniques," *J. Neural Transm. Suppl.* 49(3-4):1-10. (Japanese language document.).

Huberman, M. et al. (Jul. 1994). "Correlation of Cytokine Secretion by Mononuclear Cells of Alzheimer Patients and Their Disease Stage," *J. Neuroimmunol.* 52:147-152.

Ikeda, S. (Nov. 1989). "Alzheimer's Disease and Amyloid β-Protein," *No To Shinkei [Brain and Nerve]* 41(11):1051-1064.

Kataoka, S. et al. (1996). "Physician Education: Apoptosis," *Oncologist* 1:399-401.

Mentz, S. et al. (Mar. 1999). "Mechanism of Thrombin Clearance by Human Astrocytoma Cells," *J. Neurochem.* 72(3):980-987.

Miller, J.W. (May 2002). "Vitamin $B_{12}$ Deficiency, Tumor Necrosis Factor-α, and Epidermal Growth Factor: A Novel Function for Vitamin $B_{12}$?" *Nutr. Rev.* 60(5-Pt. 1):142-144.

Quirion, R. et al. (Aug. 1991). "Growth Factors and Lymphokines: Modulators of Cholinergic Neuronal Activity," *Can. J. Neurol. Sci.* 18(3 Suppl):390-393.

Refolo, L.M. et al. (Oct. 31, 1989). "Nerve and Epidermal Growth Factors Induce the Release of the Alzheimer Amyloid Precursor from PC 12 Cell Cultures," *Biochem. Biophys. Res. Commun.* 164(2):664-670.

Reynolds, W.F. et al. (Nov. 14, 2000). "MPO and APOEε4 Polymorphisms Interact to Increase Risk for AD in Finnish Males," *Neurology* 55(9):1284-1290.

Robakis, N.K. et al. (1991). "Expression of the Alzheimer Amyloid Precursor in Brain Tissue and Effects of NGF and EGF on Its Metabolism," *Clin. Neuropharmacol.* 14(Suppl. 1):S15-S23.

Rochette, M.J. et al. (Aug. 2002). "γ-Secretase: Substrates and Inhibitors," *Mol. Neurobiol.* 26(1):81-95.

Satoh, J. et al. (Jun. 2000). "β-Catenin Expression in Human Neural Cell Lines Following Exposure to Cytokines and Growth Factors," *Neuropathology* 20(2):113-123.

Satoh, J. et al. (Dec. 2000). "Amyloid Precursor Protein β-Secretase (BACE) mRNA Expression in Human Neural Cell Lines Following Induction of Neuronal Differentiation and Exposure to Cytokines and Growth Factors," *Neuropathology* 20(4):289-296.

Sharma, A. et al. (Nov. 1997). "Pharmacological Basis of Drug Therapy of Alzheimer's Disease," *Indian J. Exp. Biol.* 35(11):1146-1155.

Slack, B.E. et al. (1997). "Rapid Stimulation of Amyloid Precursor Protein Release by Epidermal Growth Factor: Role of Protein Kinase C," *Biochem . J.* 327:245-249.

Styren, S.D. et al. (Apr. 2, 1990). "Epidermal Growth Factor Receptor Expression in Demented and Aged Human Brain," *Brain Res.* 512(2):347-352.

Thatte, U. et al. (Oct. 1997). "Apoptosis: Clinical Relevance and Pharmacological Manipulation," *Drugs* 54(4):511-532.

Treanor, J.J.S. et al. (Jan. 2, 1991). "Low Affinity Nerve Growth Factor Receptor Binding in Normal and Alzheimer's Disease Basal Forebrain," *Neurosci. Lett.* 121(1-2):73-76.

Uchida, Y. (Nov. 1999). "Regulation of Growth Inhibitory Factor Expression by Epidermal Growth Factor and Interleukin-1β in Cultured Rat Astrocytes," *J. Neurochem.* 73(5):1945-1953.

Van Nostrand, W.E. et al. (May 11, 1990). "Protease Nexin-II (Amyloid β-Protein Precursor): A Platelet α-Granule Protein," *Science* 248(4956):745-748.

Villa, A. et al. (May 2001). "Nerve Growth Factor Modulates the Expression and Secretion of β-Amyloid Precursor Protein Through Different Mechanisms in PC12 Cells," *J. Neurochem.* 77(4):1077-1084.

Yankner, B.A. et al. (Nov. 1990). "Nerve Growth Factor Potentiates the Neurotoxicity of β Amyloid," *Proc. Natl. Acad. Sci. USA* 87:9020-9023.

Zhang, L. et al. (May-Jun. 1999). "Oxidative Stress Differentially Modulates Phosphorylation of ERK, p38 and CREB Induced by NGF or EGF in PC12 Cells," *Neurobiol. Aging* 20(3):271-278.

Zhao, B. et al. (Apr. 1, 1998). "Involvement of Cytokines in Normal CNS Development and Neurological Diseases: Recent Progress and Perspectives," *J. Neurosci. Res.* 52(1):7-16.

Zwain, I.H. et al. (Jun. 1994). "Regulation of Clusterin Secretion and mRNA Expression in Astrocytes by Cytokines," *Mol. Cell Neurosci.* 5(3):229-237.

de Boer, L. et al. (2004). "Mutations in the NSD1 Gene in Patients with Sotos Syndrome Associate with Endocrine and Paracrine Alterations in the IGF System," *European Journal of Endocrinology* 151:333-341.

Drăghici, S. (2003). *Data Analysis Tools for DNA Microarrays*. Chapman & Hall/CRC, pp. 229, 247-248, and 295.

Hoshikawa, Y. et al. (2003). "Hypoxia Induces Different Genes in the Lungs of Rats Compared with Mice," Erratum—Corrigendum—*Physiol. Genomics* 13:79.

Kovacs, E. (Mar. 2001). "The Serum Levels of IL-12 and IL-16 in Cancer Patients. Relation to the Tumour Stage and Previous Therapy," *Biomedicine & Pharmacotherapy* 55(2):111-116.

Lakatos, P. et al. (May 2000). "Serum Insulin-Like Growth Factor-I, Insulin-Like Growth Factor Binding Proteins, and Bone Mineral Content in Hyperthyroidism," *Thyroid* 10(5):417-423.

Mohan, S. et al. (Aug. 1997). "Serum Insulin-Like Growth Factor Binding Protein (IGFBP)-4 and IGFBP-5 Levels in Aging and Age-Associated Diseases," *Endocrine* 7(1):87-91.

Pasinetti, G.M. et al. (2001). "From cDNA Microarrays to High-Throughput Proteomics. Implications in the Search for Preventive Initiatives to Slow the Clinical Progression of Alzheimer's Disease Dementia," *Restorative Neurology and Neuroscience* 18(2, 3):137-142.

Qin, X. et al. (Sep. 4, 1998). "Structure-Function Analysis of the Human Insulin-Like Growth Factor Binding Protein-4," *The Journal of Biological Chemistry* 273(36):23509-23516.

Sjögren, M. et al. (2003). "Advances in the Detection of Alzheimer's Disease—Use of Cerebrospinal Fluid Biomarkers," *Clinica Chimica Acta* 332(1-2):1-10.

Tham, A. et al. (1993). "Insulin-Like Growth Factors and Insulin-Like Growth Factor Binding Proteins in Cerebrospinal Fluid and Serum of Patients with Dementia of the Alzheimer Type," *Journal of Neural Transmission* 5(3):165-176.

Turner, R.S. (Sep. 2003). "Biomarkers of Alzheimer's Disease and Mild Cognitive Impairment: Are We There Yet?" *Experimental Neurology* 183(1):7-10.

Bimonte-Nelson, H.A. et al. (Jun. 2003). "Testosterone, but not Nonaromatizable Dihydrotestosterone, Improves Working Memory and Alters Nerve Growth Factor Levels in Aged Male Rats," *Exp. Neurol.* 181(2):301-312.

Capsoni, S. et al. (Jun. 6, 2000). "Alzheimer-Like Neurodegeneration in Aged Antinerve Growth Factor Transgenic Mice," *Proc. Natl. Acad. Sci. U.S.A.* 97(12):6826-6831.

Gibbs, R.B. (Mar. 23, 1998). "Levels of trkA and BDNF mRNA, but not NGF mRNA, Fluctuate Across the Estrous Cycle and Increase in Response to Acute Hormone Replacement," *Brain Res.* 787(2):259-268.

Gibbs, R.B. (Nov. 9, 1998). "Levels of trkA and BDNF mRNA, but not NGF mRNA, Fluctuate Across the Estrous Cycle and Increase in Response to Acute Hormone Replacement," Erratum, *Brain Res.* 810(1-2):294.

Hartbauer, M. et al. (2001). "Antiapoptotic Effects of the Peptidergic Drug Cerebrolysin on Primary Cultures of Embryonic Chick Cortical Neurons," *J. Neural Transm.* 108(4):459-473.

Hellweg, R. et al. (1994). "Neurotrophic Factors in Memory Disorders," *Life Sci.* 55(25-26):2165-2169.

Intebi, A.D. et al. (2002-2003). "Alzheimer's Disease Patients Display Gender Dimorphism in Circulating Anorectic Adipokines," *NeuroImmunoModulation* 10(6):351-358.

Kim, S.H. et al. (Dec. 9, 2002). "Brain-Derived Neurotrophic Factor Can Act as a Pronecrotic Factor Through Transcriptional and Translational Activation of NADPH Oxidase," *J. Cell Biol.* 159(5):821-31.

Kingham, P.J. et al. (1999). "Apoptotic Pathways Mobilized in Microglia and Neurones as a Consequence of Chromogranin A-Induced Microglial Activation," *J. Neurochem.* 73(2):538-547.

Lang, U.E. et al. (Mar. 2, 2004; Dec. 29, 2003). "State of the Art of the Neurotrophin Hypothesis in Psychiatric Disorders: Implications and Limitations," *J. Neural Transm.* 111(3):387-411.

Laske, C. et al. (2006). "Stage-Dependent BDNF Serum Concentrations in Alzheimer's Disease," *J. Neural Transm.* 113:1217-1224.

Lee, S.Y. et al. (May 2003, e-pub. Mar. 5, 2003). "17β-Estradiol Activates ICI 182,780-Sensitive Estrogen Receptors and Cyclic GMP-Dependent Thioredoxin Expression for Neuroprotection," *FASEB J.* 17(8):947-948.

Lorigados, L. et al. (Jul. 1992). "Two-Site Enzyme Immunoassay for βNGF Applied to Human Patient Sera," *J. Neurosci. Res.* 32(3):329-339.

Michalski, B. et al. (Mar. 17, 2003). "Pro-Brain-Derived Neurotrophic Factor is Decreased in Parietal Cortex in Alzheimer's Disease," *Mol. Brain Res.* 111(1-2):148-154.

Murase, K. et al. (Jun. 1994). "Neurotrophin-3 (NT-3) Levels in the Developing Rat Nervous System and in Human Samples," *Clin. Chim. Acta* 227(1-2):23-36.

Nonaka, N. et al. (Dec. 9, 2002). "Regional Differences in PACAP Transport Across the Blood-Brain Barrier in Mice: A Possible Influence of Strain, Amyloid β Protein, and Age," *Peptides* 23:2197-2202.

Olson, L. (Nov. 1993). "NGF and the Treatment of Alzheimer's Disease," *Exp. Neurol.* 124(1):5-15.

Phillips, H.S. et al. (Nov. 1991). "BDNF mRNA Is Decreased in the Hippocampus of Individuals with Alzheimer's Disease," *Neuron* 7(5):695-702.

Ping, S.E. et al. (Jul. 1, 2002; e-pub. May 15, 2002). "Estrogen Treatment Suppresses Forebrain P75 Neurotrophin Receptor Expression in Aged, Noncycling Female Rats," *J. Neurosci. Res.* 69(1):51-60.

Reiriz, J. et al. (Mar. 2002). "BMP-2 and cAMP Elevation Confer Locus Coeruleus Neurons Responsiveness to Multiple Neurotrophic Factors," *J. Neurobiol.* 50(4):291-304.

Roher A.E. et al. (Apr. 2000). "Cortical Cholinergic Denervation Elicits Vascular Aβ Deposition," *Ann. N. Y. Acad. Sci.* 903:366-373.

Simpkins, J.W. et al. (Sep. 22, 1997). "Role of Estrogen Replacement Therapy in Memory Enhancement and the Prevention of Neuronal Loss Associated With Alzheimer's Disease," *Am. J. Med.* 103(3A):19S-25S.

Singh, M. et al. (May 1995). "The Effect of Ovariectomy and Estradiol Replacement on Brain-Derived Neurotrophic Factor Messenger Ribonucleic Acid Expression in Cortical and Hippocampal Brain Regions of Female Sprague-Dawley Rats," *Endocrinology* 136(5):2320-2324.

Teunissen, C.E. et al. (2002). "Biochemical Markers Related to Alzheimer's Dementia in Serum and Cerebrospinal Fluid," *Neurobiol. Aging* 23:485-508.

Tong, L. et al. (Jul. 28, 2004). "β-Amyloid Peptide at Sublethal Concentrations Downregulates Brain-Derived Neurotrophic Factor Functions in Cultured Cortical Neurons," *J. Neurosci.* 24(30):6799-6809.

Tuszynski, M.H. et al. (Apr. 1996). "Gene Therapy in the Adult Primate Brain: Intraparenchymal Grafts of Cells Genetically Modified to Produce Nerve Growth Factor Prevent Cholinergic Neuronal Degeneration," *Gene Ther.* 3(4):305-314.

Verdier, Y. et al. (2004). "Binding Sites of Amyloid β-Peptide in Cell Plasma Membrane and Implications for Alzheimer's Disease," *Curr. Protein Pept. Sci.* 5(1):19-31.

Verdier, Y. et al. (May 2004). "Amyloid β-Peptide Interactions with Neuronal and Glial Cell Plasma Membrane: Binding Sites and Implications for Alzheimer's Disease," *J. Pept. Sci.* 10(5):229-248.

Windisch, M. et al. (1998). "Neurotrophic Activities and Therapeutic Experience with a Brain Derived Peptide Preparation," *J. Neural Transm. Suppl.* 53:289-298.

Wirdefeldt, K. et al. (Jul. 26, 2003). "A Linkage Study of Candidate Loci in Familial Parkinson's Disease," *BMC Neurol.* 3, seven pages.

* cited by examiner

METHODS FOR DIAGNOSIS OF ALZHEIMER'S DISEASE IN BLOOD SAMPLES

CROSS-REFERENCE TO RELATED APPLICATIONS

Statement Regarding Federally Sponsored Research or Development

Not applicable.

REFERENCE TO A COMPACT DISK APPENDIX

Not applicable

BACKGROUND OF THE INVENTION

An estimated 4.5 million Americans have Alzheimer's Disease ("AD"). By 2050, the estimated range of AD prevalence will be 11.3 million to 16 million. Currently, the societal cost of AD to the U.S. is $100 billion per year, including $61 billion born by U.S. businesses. Neither Medicare nor most private health insurance covers the long-term care most patients need.

Alzheimer's Disease is a neurodegenerative disease of the central nervous system associated with progressive memory loss resulting in dementia. Two pathological characteristics are observed in AD patients at autopsy: extracellular plaques and intracellular tangles in the hippocampus, cerebral cortex, and other areas of the brain essential for cognitive function. Plaques are formed mostly from the deposition of amyloid beta ("A$\beta$"), a peptide derived from amyloid precursor protein ("APP"). Filamentous tangles are formed from paired helical filaments composed of neurofilament and hyperphosphorylated tau protein, a microtubule-associated protein. It is not clear, however, whether these two pathological changes are only associated with the disease or truly involved in the degenerative process. Late-onset/sporadic AD has virtually identical pathology to inherited early-onset/familial AD (FAD), thus suggesting common pathogenic pathways for both forms of AD. To date, genetic studies have identified three genes that cause autosomal dominant, early-onset AD, amyloid precursor protein ("APP"), presenilin 1 ("PS1"), and presenilin 2 ("PS2"). A fourth gene, apolipoprotein E ("ApoE"), is the strongest and most common genetic risk factor for AD, but does not necessarily cause it. All mutations associated with APP and PS proteins can lead to an increase in the production of A$\beta$ peptides, specifically the more amyloidogenic form, A$\beta_{42}$. In addition to genetic influences on amyloid plaque and intracellular tangle formation, environmental factors (e.g., cytokines, neurotoxins, etc.) may also play important roles in the development and progression of AD.

The main clinical feature of AD is a progressive cognitive decline leading to memory loss. The memory dysfunction involves impairment of learning new information which is often characterized as short-term memory loss. In the early (mild) and moderate stages of the illness, recall of remote well-learned material may appear to be preserved, but new information cannot be adequately incorporated into memory. Disorientation to time is closely related to memory disturbance.

Language impairments are also a prominent part of AD. These are often manifest first as word finding difficulty in spontaneous speech. The language of the AD patient is often vague, lacking in specifics and may have increased automatic phrases and clichés. Difficulty in naming everyday objects is often prominent. Complex deficits in visual function are present in many AD patients, as are other focal cognitive deficits such as apraxia, acalculia and left-right disorientation. Impairments of judgment and problems solving are frequently seen.

Non-cognitive or behavioral symptoms are also common in AD and may account for an event larger proportion of caregiver burden or stress than the cognitive dysfunction. Personality changes are commonly reported and range from progressive passivity to marked agitation. Patients may exhibit changes such as decreased expressions of affection. Depressive symptoms are present in up to 40%. A similar rate for anxiety has also been recognized. Psychosis occurs in 25%. In some cases, personality changes may predate cognitive abnormality.

Currently, the primary method of diagnosing AD in living patients involves taking detailed patient histories, administering memory and psychological tests, and ruling out other explanations for memory loss, including temporary (e.g., depression or vitamin B$_{12}$ deficiency) or permanent (e.g., stroke) conditions. These clinical diagnostic methods, however, are not foolproof.

One obstacle to diagnosis is pinpointing the type of dementia; AD is only one of seventy conditions that produce dementia. Because of this, AD cannot be diagnosed with complete accuracy until after death, when autopsy reveals the disease's characteristic amyloid plaques and neurofibrillary tangles in a patient's brain. In addition, clinical diagnostic procedures are only helpful after patients have begun displaying significant, abnormal memory loss or personality changes. By then, a patient has likely had AD for years.

Given the magnitude of the public health problem posed by AD, considerable research efforts have been undertaken to elucidate the etiology of AD as well as to identify biomarkers (secreted proteins or metabolites) that can be used to diagnose and/or predict whether a person is likely to develop AD. Because AD the CNS is relatively isolated from the other organs and systems of the body, most research (in regards to both disease etiology and biomarkers) has focused on events, gene expression, biomarkers, etc. within the central nervous system. With regards to biomarkers, the proteins amyloid beta and tau are probably the most well characterized. Research has shown that cerebrospinal fluid ("CSF") samples from AD patients contain higher than normal amounts of tau, which is released as neurons degenerate, and lower than normal amounts of beta amyloid, presumably because it is trapped in the brain in the form of amyloid plaques. Because these biomarkers are released into CSF, a lumbar puncture (or "spinal tap") is required to obtain a sample for testing.

A number of U.S. patents have been issued relating to methods for diagnosing AD, including U.S. Pat. Nos. 4,728,605, 5,874,312, 6,027,896, 6,114,133, 6,130,048, 6,210,895, 6,358,681, 6,451,547, 6,461,831, 6,465,195, 6,475,161, and 6,495,335. Additionally, a number of reports in the scientific literature relate to certain biochemical markers and their correlation/association with AD, including Fahnestock et al., 2002, *J. Neural. Transm. Suppl.* 2002(62):241-52; Masliah et al., 1195, *Neurobiol. Aging* 16(4):549-56; Power et al., 2001, *Dement. Geriatr. Cogn. Disord.* 12(2):167-70; and Burbach et al., 2004, *J. Neurosci.* 24(10):2421-30. Additionally, Li et al. (2002, *Neuroscience* 113(3):607-15) and Sanna et al. (2003, *J. Clin. Invest.* 111(2):241-50) have investigated Leptin in relation to memory and multiple sclerosis, respectively.

All patents and publications cited herein are incorporated by reference in their entirety.

BRIEF SUMMARY OF THE INVENTION

The inventors have discovered a collection of biochemical markers, present in the serum of individuals, which are altered in individuals with Alzheimer's Disease ("AD"). Accordingly, these biomarkers ("AD diagnosis biomarkers") may be used to assess cognitive function, to diagnose or aid in the diagnosis of AD and/or to measure progression of AD in AD patients. AD diagnosis markers may be used individually or in combination for diagnosing or aiding in the diagnosis of AD. The invention provides methods for the diagnosis of AD or aiding the diagnosis of AD in an individual by measuring the amount of one or more AD diagnosis biomarkers in a biological fluid sample, such as a peripheral biological fluid sample from the individual and comparing the measured amount with a reference value for each AD diagnosis biomarker measured. The information thus obtained may be used to aid in the diagnosis or to diagnose AD in the individual. Accordingly, the present invention provides a method of aiding diagnosis of Alzheimer's disease ("AD"), comprising comparing a measured level of at least one AD diagnosis biomarker in a biological fluid sample from an individual to a reference level for the biomarker, wherein the AD diagnosis biomarker is selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD diagnosis biomarker is selected from the group consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β). In other examples, the AD diagnosis marker is selected from the group consisting of BDNF, sIL-6R, IL-8, leptin, MIP-1δ, PDGF-BB, and TIMP-1. In yet other examples, the AD diagnosis marker is selected from the group consisting of sIL-6R, IL-8, and TIMP-1. In further examples, the AD diagnosis marker is selected from the group consisting of BDNF, MIP-1δ, and TIMP-1. In additional examples, the AD diagnosis marker is selected from the group consisting of BDNF, PDGF-BB, leptin and RANTES. In additional examples, the AD diagnosis marker comprises BDNF, PDGF-BB, leptin and RANTES.

Provided herein are methods of aiding diagnosis of Alzheimer's disease ("AD"), comprising comparing a measured level of at least four AD diagnosis biomarkers, wherein said biomarkers comprise BDNF, PDGF-BB, leptin and RANTES, in a biological fluid sample from an individual to a reference level for each AD diagnosis biomarker. In some examples, AD is diagnosed when BDNF is decreased at least about 20% as compared to a reference level of BDNF. In other examples, AD is diagnosed when Leptin is decreased at least about 25% as compared to a reference level of Leptin. In additional examples, AD is diagnosed when RANTES is decreased at least about 16% as compared to a reference level of RANTES. In further examples, severe AD is diagnosed when PDGF-BB is decreased at least about 85% as compared to a reference level of PDGF-BB. In yet further examples, the biological fluid sample is a peripheral biological fluid sample.

Provided herein are methods for monitoring progression of Alzheimer's disease (AD) in an AD patient, comprising: comparing a measured level of at least one AD diagnosis biomarker in a biological fluid sample from an individual to a reference level for the biomarker, wherein the AD diagnosis biomarker is selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD diagnosis biomarker is selected from the group consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β). In other examples, the AD diagnosis marker is selected from the group consisting of BDNF, PDGF-BB, leptin and RANTES.

The inventors have also discovered methods of identifying individuals with mild cognitive deficit (MCI), a clinically recognized disorder considered distinct from AD in which cognition and memory are mildly deficient. The inventors have found that the biomarker RANTES is decreased in individuals with MCI. Individuals with MCI can be distinguished from those with AD by measuring biomarkers which are reduced in AD patients, but not those individuals with MCI (e.g., Leptin). Accordingly, the invention provides methods for diagnosing or aiding in the diagnosis of MCI by obtaining a measured value for the level of RANTES in a peripheral biological fluid sample and comparing that measured value against a reference value. In certain embodiments, such methods include obtaining a measuring value for Leptin levels in the peripheral biological fluid sample and comparing that measured level against a reference value. The information thus obtained may be used to aid in the diagnosis or to diagnose MCI in the individual.

Further, the inventors have discovered methods of stratifying AD patients (i.e., sorting individuals with a probable diagnosis of AD or diagnosed with AD into different classes of AD) by obtaining measured values for brain derived neurotrophic factor (BDNF) and BB-homodimer platelet derived growth factor (PDGF-BB) levels in a peripheral biological fluid sample from an AD patient. The measured levels of these two biomarkers are compared with reference values. The information thus obtained may be used to aid in stratification of the AD diagnosis (or probable AD diagnosis) of the individual. Accordingly, the present invention provides methods for stratifying Alzheimer's disease (AD) in an individual, comprising comparing measured values for brain derived neurotrophic factor (BDNF) and BB homodimeric platelet derived growth factor (PDGF-BB) levels in a biological fluid sample from said patient with reference values for BDNF and PDGF-BB. In some examples, the biological fluid sample is a peripheral fluid sample, including blood, serum or plasma. In other examples, the method further comprises comparing measured values for leptin and Rantes levels with reference values for leptin and Rantes, wherein reference values for BDNF, PDGF-BB, leptin and Rantes are for samples from individuals with MMSE scores from 25 to 28, wherein an increase in leptin and PDGF-BB levels and wherein levels of BDNF and RANTES stay substantially the same indicate mild AD as indicated by an MMSE score of 20-25. In additional examples, the method further comprises comparing measured values for leptin and Rantes levels with reference values for leptin and Rantes, wherein reference values for BDNF, PDGF-BB, leptin and Rantes are for samples from individuals with MMSE scores from 20-25, wherein a decrease in Rantes, BDNF, and PDGF levels and wherein levels of Leptin stays substantially the same indicate moderate AD as indicated by an MMSE score of 10-20.

In one aspect, the invention provides methods of aiding in the diagnosis of Alzheimer's disease ("AD") by obtaining a measured level of at least one AD diagnosis biomarker in a peripheral biological fluid sample from an individual, where the AD diagnosis biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β), and comparing the measured level to the reference level. In some embodiments, measured levels are obtained for at least two, three, four, or five AD diagnosis biomarkers. In some embodiments, the comparison of the measured value and the reference value includes calculating a fold difference between the measured value and the reference value. In some embodiments the measured value is obtained by measuring the level of the AD diagnosis biomarker(s) in the sample, while in other embodiments the measured value is obtained from a third party. Also provided are methods of aiding in the diagnosis of Alzheimer's disease ("AD") by comparing a measured level of at least one AD diagnosis biomarker in a peripheral biological fluid sample from an individual with a reference level. Further provided are methods of aiding in the diagnosis of Alzheimer's disease ("AD") by measuring a level of at least one AD diagnosis biomarker in a peripheral biological fluid sample from an individual, wherein a decrease as compared to a reference level suggests a diagnosis of AD.

In another aspect, the invention provides methods for aiding in the diagnosis of mild cognitive impairment (MCI) by obtaining a measured level for RANTES in a peripheral biological fluid sample from an individual, and comparing the measured level to a reference level. In some embodiments, the method for aiding in the diagnosis of MCI also includes obtaining a measured value for Leptin in the peripheral biological fluid sample and comparing measured value for Leptin to a reference level. In certain embodiments, the measured value is obtained by measuring the level of RANTES (and/or Leptin) in the sample, while in other embodiments, the measured value(s) is obtained from a third party. Also provided are methods of aiding in the diagnosis of mild cognitive impairment (MCI) by comparing a measured level for RANTES, and optionally Leptin, in a peripheral biological fluid sample from an individual with a reference level. Further provided are methods for aiding in the diagnosis of MCI by measuring a level for RANTES, and optionally Leptin, in a peripheral biological fluid sample from an individual, wherein a reduction in the RANTES level as compared to a reference level suggests a diagnosis of MCI (in embodiments in which Leptin in measured, a Leptin level that is equal to or greater than the reference level also suggests MCI).

In a further aspect, the invention provides methods for monitoring progression of Alzheimer's disease (AD) in an AD patient by obtaining a measured value for Leptin in a peripheral biological fluid sample; and comparing said measured value for Leptin with a reference value. In certain embodiments, the measured value is obtained by measuring the level of Leptin in the sample to produce, while in other embodiments, the measured value is obtained from a third party. Also provided are methods for monitoring progression of AD in an AD patient by comparing a measured value for Leptin in a peripheral biological fluid sample with a reference value. Further provided are methods for monitoring progression of AD in an AD patient by measuring a level for Leptin in a peripheral biological fluid sample, wherein a decrease in Leptin as compared with a reference value suggests progression (increased severity) of the AD.

In another aspect, the invention provides methods for stratifying AD in an AD patient. In some embodiments, stratification between mild and more advanced AD is carried out by obtaining a measured value for brain derived neurotrophic factor (BDNF) levels in a peripheral biological fluid sample from an AD patient, and comparing the measured value with reference values for BDNF. In other embodiments, stratification between mild, moderate, and severe AD is carried out by obtaining levels for BDNF and BB homodimeric platelet derived growth factor (PDGF-BB), and comparing the measured levels with reference levels for BDNF and PDGF-BB. In certain embodiments, the measured value is obtained by measuring the level(s) of BDNF (and PDGF-BB) in the sample to produce the measured value(s), while in other embodiments, the measured value(s) is obtained from a third party. Also provided are methods for stratifying AD in an AD patient by comparing a BDNF (and, optionally, PDGF-BB) level in a peripheral biological fluid sample from an AD patient with a reference value for BDNF (and PDGF-BB when appropriate). Further provided are methods for stratifying AD in an AD patient by measuring a BDNF level (and, optionally, a PDGF-BB level) in a peripheral biological fluid sample, wherein a low level of BDNF (as compared to a reference value) suggests mild AD, a high level of BDNF (as compared to a reference value) suggests more advanced AD, a high level of BDNF and a low level of PDGF-BB (as compared to reference values) suggests moderate AD, and a high level of BDNF and a high level of PDGF-BB (as compared to reference values) suggests severe AD.

In some embodiments, the peripheral biological fluid sample is a blood sample. In certain embodiments the peripheral biological fluid sample is a plasma sample. In other embodiments, the peripheral biological fluid sample is a serum sample.

In yet another aspect, the invention provides methods of identifying candidate agents for treatment of Alzheimer's Disease by assaying a prospective candidate agent for activity in modulating an AD biomarker, where the AD biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). Provided herein are methods of identifying a candidate agent for treatment of Alzheimer's Disease, comprising: assaying a prospective candidate agent for activity in modulating an AD biomarker, said AD biomarker selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD biomarkers are selected from the group consisting of BDNF, PDGF-BB, Leptin and RANTES.

In a further aspect, the invention provides kits for diagnosing Alzheimer's disease (AD) including at least one reagent specific for an AD diagnosis marker, where the AD diagnosis biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β), and instructions for carrying out a method of aiding in the diagnosis of AD described herein. Provided herein are kits comprising at least one reagent specific for at least one AD diagnosis marker, said at least one AD diagnosis biomarker selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R and instructions for carrying out methods provided herein. Additionally, provided herein are sets of reference values for AD diagnosis biomarkers comprising BDNF, PDGF-BB, Leptin and RANTES and set of reagents specific for AD diagnosis biomarkers, wherein said biomarkers comprise BDNF, PDGF-BB, Leptin and RANTES.

In another aspect, the invention provides kits for identifying individuals with mild cognitive impairment (MCI) including at least one reagent specific for RANTES; and instructions for carrying out method of aiding in the diagnosis of MCI described herein. In certain embodiments, kits for identifying individuals with MCI may also include a reagent specific for Leptin.

In yet another aspect, the invention provides kits for monitoring progression of Alzheimer's disease (AD) in AD patients including at least one reagent specific for Leptin; and instructions for carrying out a method of monitoring AD progression described herein.

In a further aspect, the invention provides kits for stratifying an Alzheimer's disease (AD) patients including at least one reagent specific for brain derived neurotrophic factor (BDNF), at least one reagent specific for BB homodimeric platelet derived growth factor (PDGF-BB), and instructions for carrying out a method of stratifying an AD patient described herein. In yet further examples, kits comprise AD diagnosis markers are selected from the group consisting of BDNF, PDGF-BB, leptin and RANTES. In further examples of kits, the reagent specific for the AD diagnosis biomarker is an antibody, or fragment thereof, that is specific for said AD diagnosis biomarker. In further examples kits further comprise at least one reagent specific for a biomarker that measures sample characteristics.

Provided herein are surfaces comprising attached thereto, at least one reagent specific for each AD diagnosis biomarker in a set of AD diagnosis biomarkers, wherein said set of AD diagnosis biomarkers comprises BDNF, PDGF-BB, leptin and RANTES. Provided herein are surfaces comprising attached thereto, at least one reagent specific for each AD diagnosis biomarker in a set of AD diagnosis biomarkers, wherein said set of AD diagnosis biomarkers consists of BDNF, PDGF-BB, leptin and RANTES; and at least one reagent specific for a biomarker that measures sample characteristics. In further examples, provided herein are surfaces wherein said reagent specific for said AD diagnosis biomarker is an antibody, or fragment thereof, that is specific for said AD diagnosis biomarker.

Provided herein are combinations comprising the surfaces as described herein having attached thereto at least one reagent specific for each AD diagnosis biomarker and a peripheral biological fluid sample from an individual. In some examples, the individual is at least 60, 65, 70, 75, 80, or 85 years of age.

Provided herein are methods for obtaining values for the comparison of the measured level to the reference level of biological fluid samples. The present invention provides computer readable formats comprising the values obtained by the methods described herein.

BRIEF DESCRIPTION OF THE DRAWINGS

FIG. 1B Leptin; and FIG. 1C RANTES, selected from the list from Table 3 shown herein in the Examples. 95 plasma samples from individuals having AD and having mean MMSE scores of 20, and mean age of 74, was compared to plasma sample from 88 age-matched controls having mean MMSE score of 30. Non-parametric, unpaired t tests comparing the mean concentration of each protein was used to determine statistical significance (p-value).

DETAILED DESCRIPTION OF THE INVENTION

Figure 1A:
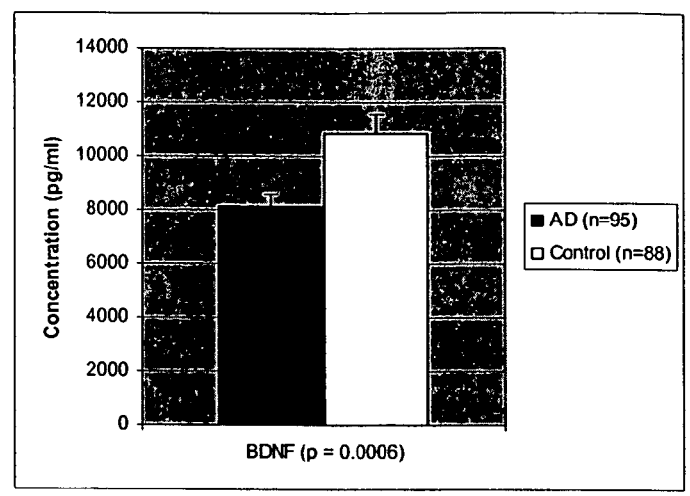
FIGS. 1A-1C show ELISA results for 3 proteins, FIG. 1A BDNF.

Inflammation and injury responses are invariably associated with neuron degeneration in AD, PD, frontotemporal dementia, cerebrovascular disease, multiple sclerosis, and neuropathies. The brain and CNS are not only immunologically active in there own accord, but also have complex peripheral immunologic interactions. Fiala et al. (1998 Mol Med. July; 4(7):480-9) has shown that in Alzheimer's disease, alterations in the permeability of the blood-brain barrier and chemotaxis, in part mediated by chemokines and cytokines, may permit the recruitment and transendothelial passage of peripheral cells into the brain parenchyma. A paradigm of the blood-brain barrier was constructed utilizing human brain endothelial and astroglial cells with the anatomical and physiological characteristics observed in vivo. This model was used to test the ability of monocytes/macrophages to transmigrate when challenged by A beta 1-42 on the brain side of the blood-brain barrier model. In that model Abeta 1-42 and monocytes on the brain side potentiated monocyte transmigration from the blood side to the brain side. In some individuals, circulating monocytes/macrophages, when recruited by chemokines produced by activated microglia and macrophages, could add to the inflammatory destruction of the brain in Alzheimer's disease.

The inventors assert that the monitoring for relative concentrations of many secreted markers measured simultaneously in the serum is a more sensitive method for monitoring the progression of disease than the absolute concentration of any single biochemical markers have been able to achieve. A composite or array embodying the use of 5, 10, 20, 30, 40, 50, 60, 70, 80, 90, 100, 110, 120, 130, 140, 150, 160, 170, 180, 190, 200 markers in Table 7 simultaneously, consisting of antibodies bound to a solid support or protein bound to a solid support, for the detection of inflammation and injury response markers associated with neuron degeneration in AD, PD, frontotemporal dementia, cerebrovascular disease, multiple sclerosis, and neuropathies.

The inventors have discovered a collection of biochemical markers (collectively termed "AD biomarkers") useful for diagnosis of AD, aiding in diagnosis of AD, monitoring AD in AD patients (e.g., tracking disease progression in AD patients, which may be useful for tracking the effect of medical or surgical therapy in AD patients), stratifying AD patients, and diagnosing or aiding in the diagnosis of mild cognitive impairment (MCI) as well as diagnosing or aiding in the diagnosis of cognitive impairment. The AD biomarkers are present in biological fluids of individuals. In some examples, the AD biomarkers are present in peripheral biological fluids (e.g., blood) of individuals, allowing collection of samples by procedures that are relatively non-invasive, particularly as compared to the lumbar puncture procedure commonly used to collect cerebrospinal fluid samples.

Definitions

As used herein, the terms "Alzheimer's patient", "AD patient", and "individual diagnosed with AD" all refer to an individual who has been diagnosed with AD or has been given a probable diagnosis of Alzheimer's Disease (AD).

As used herein, the phrase "AD biomarker" refers to a biomarker that is an AD diagnosis biomarker.

The term "AD biomarker polynucleotide", as used herein, refers to any of: a polynucleotide sequence encoding a AD biomarker, the associated trans-acting control elements (e.g., promoter, enhancer, and other gene regulatory sequences), and/or mRNA encoding the AD biomarker.

As used herein, methods for "aiding diagnosis" refer to methods that assist in making a clinical determination regarding the presence, or nature, of the AD or MCI, and may or may not be conclusive with respect to the definitive diagnosis. Accordingly, for example, a method of aiding diagnosis of AD can comprise measuring the amount of one or more AD biomarkers in a biological sample from an individual.

As used herein, the term "stratifying" refers to sorting individuals into different classes or strata based on the features of a neurological disease. For example, stratifying a population of individuals with Alzheimer's disease involves assigning the individuals on the basis of the severity of the disease (e.g., mild, moderate, advanced, etc.).

As used herein, the term "predicting" refers to making a finding that an individual has a significantly enhanced probability of developing a certain neurological disease.

As used herein, the phrase "neurological disease" refers to a disease or disorder of the central nervous system. Neurological diseases include multiple sclerosis, neuropathies, and neurodegenerative disorders such as AD, Parkinson's disease, amyotrophic lateral sclerosis (ALS), mild cognitive impairment (MCI) and frontotemporal dementia.

As used herein, "biological fluid sample" encompasses a variety of fluid sample types obtained from an individual and can be used in a diagnostic or monitoring assay. The definition encompasses blood, cerebral spinal fluid (CSF), urine and other liquid samples of biological origin. The definition also includes samples that have been manipulated in any way after their procurement, such as by treatment with reagents, solubilization, or enrichment for certain components, such as proteins or polynucleotides.

As used herein, the term "peripheral biological fluid sample" refers to a biological fluid sample that is not derived from the central nervous system (i.e., is not a CSF sample) and includes blood samples and other biological fluids not derived from the CNS.

A "blood sample" is a biological sample which is derived from blood, preferably peripheral (or circulating) blood. A blood sample may be, for example, whole blood, plasma or serum.

An "individual" is a mammal, more preferably a human. Mammals include, but are not limited to, humans, primates, farm animals, sport animals, rodents and pets.

A "Normal" individual or sample from a "Normal" individual as used herein for quantitative and qualitative data refers to an individual who has or would be assessed by a physician as not having AD or MCI, and has an Mini-Mental State Examination (MMSE) (referenced in Folstein et al., *J. Psychiatr. Res* 1975; 12:1289-198) score or would achieve a MMSE score in the range of 25-30. A "Normal" individual is generally age-matched within a range of 5 to 10 years, including but not limited to an individual that is age-matched, with the individual to be assessed.

An "individual with mild AD" is an individual who (a) has been diagnosed with AD or has been given a diagnosis of probable AD, and (b) has either been assessed with the Mini- Mental State Examination (MMSE) (referenced in Folstein et al., *J. Psychiatr. Res* 1975; 12:1289-198) and scored 22-27 or would achieve a score of 22-27 upon MMSE testing. Accordingly, "mild AD" refers to AD in a individual who has either been assessed with the MMSE and scored 22-27 or would achieve a score of 22-27 upon MMSE testing.

An "individual with moderate AD" is an individual who (a) has been diagnosed with AD or has been given a diagnosis of probable AD, and (b) has either been assessed with the MMSE and scored 16-21 or would achieve a score of 16-21 upon MMSE testing. Accordingly, "moderate AD" refers to AD in a individual who has either been assessed with the MMSE and scored 16-21 or would achieve a score of 16-21 upon MMSE testing.

An "individual with severe AD" is an individual who (a) has been diagnosed with AD or has been given a diagnosis of probable AD, and (b) has either been assessed with the MMSE and scored 12-15 or would achieve a score of 12-15 upon MMSE testing. Accordingly, "severe AD" refers to AD in a individual who has either been assessed with the MMSE and scored 12-15 or would achieve a score of 12-15 upon MMSE testing.

As used herein, the term "treatment" refers to the alleviation, amelioration, and/or stabilization of symptoms, as well as delay in progression of symptoms of a particular disorder. For example, "treatment" of AD includes any one or more of: elimination of one or more symptoms of AD, reduction of one or more symptoms of AD, stabilization of the symptoms of AD (e.g., failure to progress to more advanced stages of AD), and delay in progression (i.e., worsening) of one or more symptoms of AD.

As used herein, the phrase "fold difference" refers to a numerical representation of the magnitude difference between a measured value and a reference value for an AD biomarker. Fold difference is calculated mathematically by division of the numeric measured value with the numeric reference value. For example, if a measured value for an AD biomarker is 20 nanograms/milliliter (ng/ml), and the reference value is 10 ng/ml, the fold difference is 2 (20/10=2). Alternatively, if a measured value for an AD biomarker is 10 nanograms/milliliter (ng/ml), and the reference value is 20 ng/ml, the fold difference is 10/20 or –0.50 or –50%).

As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the individual with AD, MCI or cognitive impairment, but at an earlier point in time, or a value obtained from a sample from an AD patient other than the individual being tested, or a "normal" individual, that is an individual not diagnosed with AD. The reference value can be based on a large number of samples, such as from AD patients or normal individuals or based on a pool of samples including or excluding the sample to be tested.

As used herein, "a", "an", and "the" can mean singular or plural (i.e., can mean one or more) unless indicated otherwise.

Methods of the Invention

Methods for Identifying Biomarkers

The invention provides methods for identifying one or more biomarkers useful for diagnosis, aiding in diagnosis, stratifying, assessing risk, monitoring, and/or predicting a neurological disease. In certain aspects of the invention, levels of a group of biomarkers are obtained for a set of peripheral biological fluid samples from one or more individuals. The samples are selected such that they can be segregated into one or more subsets on the basis of a neurological disease (e.g., samples from normal individuals and those diagnosed with amyotrophic lateral sclerosis or samples from individuals with mild Alzheimer's disease and those with severe Alzheimer's disease). The measured values from the samples are compared to each other to identify those biomarkers which differ significantly amongst the subsets. Those biomarkers that vary significantly amongst the subsets may then be used in methods for aiding in the diagnosis, diagnosis, stratification, monitoring, and/or prediction of neurological disease. In other aspects of the invention, measured values for a set of peripheral biological fluid samples from one or more individuals (where the samples can be segregated into one or more subsets on the basis of a neurological disease) are compared, wherein biomarkers that vary significantly are useful for aiding in the diagnosis, diagnosis, stratification, monitoring, and/or prediction of neurological disease. In further aspects of the invention, levels of a set of peripheral biological fluid samples from one or more individuals (where the samples can be segregated into one or more subsets on the basis of a neurological disease) are measured to produced measured values, wherein biomarkers that vary significantly are useful for aiding in the diagnosis, diagnosis, stratification, monitoring, and/or prediction of neurological disease.

The instant invention utilizes a set of peripheral biological fluid samples, such as blood samples, that are derived from one or more individuals. The set of samples is selected such that it can be divided into one or more subsets on the basis of a neurological disease. The division into subsets can be on the basis of presence/absence of disease, stratification of disease (e.g., mild vs. moderate), or subclassification of disease (e.g., relapsing/remitting vs. progressive relapsing).

Biomarkers measured in the practice of the invention may be any proteinaceous biological marker found in a peripheral biological fluid sample. Table 7 contains a collection of exemplary biomarkers. Additional biomarkers are described herein.

Accordingly, the invention provides methods identifying one or more biomarkers which can be used to aid in the diagnosis, diagnose, detect, stratify, and/or predict neurological diseases such as neurodegenerative disorders. The methods of the invention are carried out by obtaining a set of measured values for a plurality of biomarkers from a set of peripheral biological fluid samples, where the set of peripheral biological fluid samples is divisible into at least two subsets in relation to a neurological disease, comparing said measured values between the subsets for each biomarker, and identifying biomarkers which are significantly different between the subsets.

The process of comparing the measured values may be carried out by any method known in the art, including Significance Analysis of Microarrays, Tree Harvesting, CART, MARS, Self Organizing Maps, Frequent Item Set, or Bayesian networks.

In one aspect, the invention provides methods for identifying one or more biomarkers useful for the diagnosis of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying at least one biomarker for which the measured values are significantly different between the subsets. In some embodiments, the comparing process is carried out using Significance Analysis of Microarrays. In certain embodiments, the neurodegenerative disease is from the group consisting of Alzheimer's disease, Parkinson's disease, Huntington's disease, and amyotrophic lateral sclerosis (ALS).

In another aspect, the invention provides methods for identifying at least one biomarker useful for aiding in the diagnosis of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying biomarkers for which the measured values are significantly different between the subsets.

In a further aspect, the invention provides methods for identifying at least one biomarker useful for the stratification of a neurological disease by obtaining measured values from a set of peripheral biological fluid samples for a plurality of biomarkers, wherein the set of peripheral biological fluid samples is divisible into subsets on the basis of strata of a neurological disease, comparing the measured values from each subset for at least one biomarker; and identifying biomarkers for which the measured values are significantly different between the subsets.

In another aspect, the invention provides methods for identifying at least one biomarker useful for the monitoring of a neurological disease by obtaining measured values from a set of peripheral biological fluid samples for a plurality of biomarkers, wherein the set of peripheral biological fluid samples is divisible into subsets on the basis of strata of a neurological disease, comparing the measured values from each subset for at least one biomarker; and identifying biomarkers for which the measured values are significantly different between the subsets.

In yet another aspect, the invention provides methods for identifying at least one biomarker useful for the prediction of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying biomarkers for which the measured values are significantly different between the subsets.

Methods of Assessing Cognitive Function

Provided herein are methods for assessing cognitive function, assessing cognitive impairment, diagnosing or aiding diagnosis of cognitive impairment by obtaining measured levels of one or more AD diagnosis biomarkers in a biological fluid sample from an individual, such as for example, a peripheral biological fluid sample from an individual, and comparing those measured levels to reference levels. Reference to "AD diagnosis markers" herein is a term of convenience to refer to the markers described herein and their use, and is not intended to indicate the markers are only used to diagnose AD. As this disclosure makes clear, these biomarkers are useful for, for example, assessing cognitive function, assessing MCI, assessing risk of developing AD, stratifying AD, etc. AD biomarkers include but are not limited to secreted proteins or metabolites present in a person's biological fluids (that is, a biological fluid sample), such as for example, blood, including whole blood, plasma or serum; urine; cerebrospinal fluid; tears; and saliva. Biological fluid samples encompass clinical samples, and also includes serum, plasma, and other biological fluids. As described herein, assessment of results can depend on whether the data were obtained by the qualitative or quantitative methods described herein and/or type of reference point used. For example, as described in Example 4, qualitative measurement of AD biomarker levels relative to another reference level, which may be relative to the level of another AD biomarker, may be obtained. In other methods described herein, such as in Example 7, quantitative or absolute values, that is protein concentration levels, in a biological fluid sample may be obtained. "Quantitative" result or data refers to an absolute value (see Example 7), which can include a concentration of a biomarker in pg/ml or ng/ml of molecule to sample. An example of a quantitative value is the measurement of concentration of protein levels directly for example by ELISA. "Qualitative" result or data provides a relative value which is as compared to a reference value. In some examples herein (Example 4), qualitative measurements are assessed by signal intensity on a filter. In some examples herein, multiple antibodies specific for AD biomarkers are attached to a suitable surface, e.g. as slide or filter.

In one aspect, the present invention provides methods of aiding diagnosis of Alzheimer's disease ("AD") and diagnosing AD, by obtaining measured levels of one or more AD diagnosis biomarkers in a biological fluid sample from an individual, such as for example, a peripheral biological fluid sample from an individual, and comparing those measured levels to reference levels. In some examples, the AD diagnosis biomarkers are selected from the group shown in Table 7. In other examples, the AD diagnosis biomarkers are selected from the group GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In yet other examples, the AD diagnosis biomarker are selected from the group shown in Table 3. In further examples, the AD diagnosis biomarkers are selected from the group consisting of BDNF, PDGF-BB, Leptin and RANTES. As shown herein in the examples, quantitative Leptin and BDNF levels have a statistically significant positive correlation with MMSE scores; quantitative PDGF-BB levels have a statistically significant negative correlation with MMSE scores in men; and quantitative RANTES levels have a statistically significant positive correlation with PDGF-BB and BDNF. In some examples, the AD diagnosis biomarkers for use in methods of aiding diagnosis of Alzheimer's disease ("AD") and diagnosing AD include two or more of the following 4 biomarkers: BDNF, PDGF-BB, Leptin and RANTES. In further examples, the AD diagnosis biomarkers for use in methods of aiding diagnosis of Alzheimer's disease ("AD") and diagnosing AD comprise Leptin and RANTES; Leptin and BDNF; Leptin and PDGF-BB; Leptin, RANTES and BDNF; Leptin, RANTES and PDGF-BB; Leptin, BDNF and PDGF-BB; RANTES and BDNF; RANTES and PDGF-BB; RANTES, BDNF, and PDGF-BB; BDNF and PDGF-BB; or Leptin, RANTES, BDNF and PDGF-BB. In some examples, the AD diagnosis markers for use in methods of aiding diagnosis of AD or diagnosing AD comprise Leptin, RANTES, BDNF and PDGF-BB. In other examples, the AD diagnosis markers for use in methods of aiding diagnosis of AD or diagnosing AD consist essentially of or consist of Leptin, RANTES, BDNF and PDGF-BB.

Methods of assessing cognitive function, aiding diagnosis of AD and diagnosing AD as described herein may comprise any of the following steps of obtaining a biological fluid sample from an individual, measuring the level of at least one AD diagnosis biomarker in the sample and comparing the measured level to an appropriate reference; obtaining measured levels of at least one AD diagnosis biomarker in a sample and comparing the measured level to an appropriate reference; comparing measured levels of at least one AD diagnosis biomarker obtained from a sample to an appropriate reference; measuring the level of at least one AD diagnosis biomarker in a sample; measuring the level of at least one AD diagnosis biomarker in a sample and comparing the measured level to an appropriate reference; diagnosing AD based on comparison of measured levels to an appropriate reference; or obtaining a measured value for at least one AD diagnosis biomarker in a sample. Comparing a measured level of an AD diagnosis biomarker to a reference level or obtaining a measured value for an AD diagnosis biomarker in a sample may be performed for 1, 2, 3, 4, 5, 6, 7, 8, 9, 10, or more AD diagnosis biomarker(s). The present invention also provides methods of evaluating results of the analytical methods described herein. Such evaluation generally entails reviewing such results and can assist, for example, in advising regarding clinical and/or diagnostic follow-up and/or treatment options. The present invention also provides methods for assessing a biological fluid sample for an indicator of any one or more of the following: cognitive function and/or impairment; MCI; AD; extent of AD, such as, for example, mild, moderate, severe; progression of AD; by measuring the level of or obtaining the measured level of or comparing a measured level of an AD diagnosis biomarker as described herein. Methods of assessing cognitive impairment includes the ADAS-COG, which is generally accepted to be equivalent to MMSE scoring.

For methods of diagnosing AD as described herein, the reference level is generally a predetermined level considered 'normal' for the particular AD diagnosis biomarker (e.g., an average level for age-matched individuals not diagnosed with AD), although reference levels which are determined contemporaneously (e.g., a reference value that is derived from a pool of samples including the sample being tested) are also contemplated. Also provided are methods of aiding in the diagnosis of Alzheimer's disease ("AD") by comparing a measured level of at least one AD diagnosis biomarker in a biological fluid sample, such as, for example, a peripheral biological fluid sample from an individual with a reference level. Further provided are methods of aiding in the diagnosis of Alzheimer's disease ("AD") by measuring a level of at least one AD diagnosis biomarker in a biological fluid sample, such as, for example, a peripheral biological fluid sample from an individual. For the AD diagnosis biomarkers disclosed herein, a measurement for a marker which is below the reference level suggests (i.e., aids in the diagnosis of) or indicates a diagnosis of AD.

In another aspect, the invention provides methods of identifying individuals with mild cognitive impairment (MCI), by obtaining a quantitative measured level for RANTES in a biological fluid sample, such as, for example, a peripheral biological fluid sample from an individual, and comparing that level to a reference level. Generally, the reference level for RANTES is a predetermined level considered 'normal' for RANTES, and may be an age-matched normal level for RANTES, although reference levels which are determined contemporaneously (e.g., a reference value that is derived from a pool of samples including the sample being tested) are also contemplated. Also provided are methods of aiding in the diagnosis of MCI by comparing a quantitative measured level for RANTES in a biological fluid sample, such as, for example, a peripheral biological fluid sample from an individual with a reference level. Further provided are methods for aiding in the diagnosis of MCI by measuring a level for RANTES in a biological fluid sample, such as, for example, a peripheral biological fluid sample from an individual. A finding that the quantitative level of RANTES is low (below the reference level) in the biological fluid sample, such as, for example, the peripheral biological fluid sample from the individual suggests (i.e., aids in the diagnosis of) or indicates a diagnosis of MCI. In certain embodiments, such methods further include measuring, obtaining, and/or comparing the quantitative level of Leptin in the biological fluid sample, such as, for example, a peripheral biological sample. When both RANTES and Leptin levels are utilized, a finding that the quantitative RANTES level is low while the quantitative Leptin level is not (i.e., is substantially the same as or higher than the Leptin reference value) suggests (i.e., aids in the diagnosis of) or indicates a diagnosis of MCI. Accordingly the present invention provides methods for aiding in the diagnosis of mild cognitive impairment (MCI), comprising comparing a measured level for RANTES in a biological fluid sample obtained from an individual to a reference level. In some examples, the methods further comprise comparing a measured value for leptin in the biological fluid sample obtained from the individual to a reference level. In yet other examples, the methods further comprise measuring a level for leptin in said biological fluid sample, thereby producing said measured value for leptin. In yet other examples, the methods comprise measuring a level for RANTES in said biological fluid sample, thereby producing said measured value for RANTES. In yet other examples, the biological fluid sample is a peripheral fluid sample.

In a further aspect, the invention provides methods of monitoring progression of AD in an AD patient. As shown in Example 7, the inventors have found that quantitative levels of RANTES are decreased in AD patients with Questionable AD (MMSE=25-28); and that quantitative levels of RANTES are decreased in AD patients with mild AD (MMSE=20-25), and RANTES levels decrease further as the severity of the AD intensifies. An individual with "Questionable AD" as used herein for quantitative data (also called absolute measurement) is an individual who (a) has been diagnosed with AD or has been given a diagnosis of probable AD, and (b) has either been assessed with the Mini-Mental State Examination (MMSE) (referenced in Folstein et al., *J. Psychiatr. Res* 1975; 12:1289-198) and scored 25-28 or would achieve a score of 25-28 upon MMSE testing. Accordingly, "Questionable AD" refers to AD in a individual having scored 25-28 on the MMSE and or would achieve a score of 25-28 upon MMSE testing. The reference level may be a predetermined level considered 'normal' for the particular RANTES (e.g., an average level for age-matched individuals not diagnosed with AD or MCI), or may be a historical reference level for the particular patient (e.g., a RANTES level that was obtained from a sample derived from the same individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a quantitative value for RANTES from a biological fluid sample, such as for example, a peripheral biological fluid sample and comparing measured value to a reference value. Also provided are methods for monitoring progression of AD in an AD patient by comparing a measured value for leptin in a biological fluid sample, such as for example, a peripheral biological fluid sample with a reference value. Further provided are methods for monitoring progression of AD in an AD patient by measuring a level for leptin in a biological fluid sample, such as for example, a peripheral biological fluid sample. A decrease in the measured value indicates or suggests (diagnoses or suggests a diagnosis) progression (e.g., an increase in the severity) of AD in the AD patient.

In a further aspect, the inventors have found that quantitative Leptin levels are decreased in AD patients with Questionable AD; and that the quantitative levels of Leptin are decreased in AD patients with mild AD, and quantitative Leptin levels decrease further as the severity of the AD intensifies; and the quantitative levels of Leptin are positively correlated with MMSE scores (as described in Example 7). The reference level may be a predetermined level considered 'normal' for the particular Leptin (e.g., an average level for age-matched individuals not diagnosed with AD or MCI), or may be a historical reference level for the particular patient (e.g., a Leptin level that was obtained from a sample derived from the same individual, but at an earlier point in time). Quantitative reference levels which are determined contemporaneously (e.g., a reference value that is derived from a pool of samples including the sample being tested) are also contemplated. Accordingly, the invention provides methods for monitoring progression of AD in an AD patient by obtaining a quantitative measured value for Leptin from a biological fluid sample, such as for example, a peripheral biological fluid sample and comparing measured value to a reference value. Also provided are methods for monitoring progression of AD in an AD patient by comparing a measured value for Leptin in a biological fluid sample, such as for example, a peripheral biological fluid sample with a reference value. Further provided are methods for monitoring progression of AD in an AD patient by measuring a level for Leptin in a biological fluid sample, such as for example, a peripheral biological fluid sample. A decrease in the quantitative measured value indicates or suggests (diagnoses or suggests a diagnosis) progression (e.g., an increase in the severity) of AD in the AD patient.

The inventors have found that quantitative BDNF levels are decreased in AD patients with mild AD, and that the quantitative BDNF levels in women are correlated with MMSE scores and BDNF levels decrease further as the severity of the AD intensifies (as described in Example 7). The reference level may be a predetermined level considered 'normal' for the particular BDNF (e.g., an average level for age-matched individuals not diagnosed with AD or MCI), or may be a historical reference level for the particular patient (e.g., a BDNF level that was obtained from a sample derived from the same individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a quantitative measured value for BDNF from a biological fluid sample, such as for example, a peripheral biological fluid sample and comparing measured value to a reference value. Also provided are methods for monitoring progression of AD in an AD patient by comparing a quantitative measured value for BDNF in a biological fluid sample, such as for example, a peripheral biological fluid sample with a reference value. Further provided are methods for monitoring progression of AD in an AD patient by measuring a level for BDNF in a biological fluid sample, such as for example, a peripheral biological fluid sample. Generally speaking, a decrease in the measured value indicates or suggests (diagnoses or suggests a diagnosis) progression (e.g., an increase in the severity) of AD in the AD patient.

The inventors have found that quantitative PDGF-BB levels are decreased in AD patients with Questionable AD; that PDGF-BB levels are decreased in Questionable AB compared to Mild AD; and that the MMSE scores for male AD patients are negatively correlated with PDGF-BB levels (as described in Example 7). The reference level may be a predetermined level considered 'normal' for the PDGF-BB (e.g., an average level for age-matched male individuals not diagnosed with AD or MCI), or may be a historical reference level for the particular patient (e.g., a PDGF-BB level that was obtained from a sample derived from the same male individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a measured value for PDGF-BB from a biological fluid sample from a male, such as for example, a peripheral biological fluid sample and comparing measured value to a reference value. Also provided are methods for monitoring progression of AD in an AD patient by comparing a measured value for PDGF-BB in a biological fluid sample, such as for example, a peripheral biological fluid sample with a reference value. Further provided are methods for monitoring progression of AD in an AD patient by measuring a level for PDGF-BB in a biological fluid sample such as for example, a peripheral biological fluid sample. A decrease in the measured value indicates or suggests (diagnoses or suggests a diagnosis) progression (e.g., an increase in the severity) of AD in the AD patient.

Additionally, the invention provides methods of stratifying individuals diagnosed with (or having a probable diagnosis of) AD. The inventors have found that analysis of the levels of BDNF, or BDNF and PDGF-BB in biological fluid samples, such as, peripheral biological fluid samples provides information as to the severity of the AD in the AD patient from whom the peripheral biological fluid sample is derived. The reference values for BDNF and PDGF-BB used in these aspects of the invention are most commonly obtained from a population of AD patients other than the AD patient who is the source of the sample being tested (e.g., a mean or median value derived from a large number of AD patients), although reference levels for BDNF and PDGF-BB which are determined contemporaneously (e.g., a reference values that is derived from a pool of samples including the sample being tested) are also contemplated. Accordingly, the invention provides methods of stratifying AD patients into mild, and more advanced (e.g., moderate and severe) stages of AD ("staging") by obtaining a measured level for BDNF, and comparing the measured value with a reference value for BDNF. Accordingly, the invention provides methods of stratifying AD in an AD patient by obtaining a measured value for BDNF, and, optionally, PDGF-BB, in a biological fluid sample, such as a peripheral biological fluid sample, and comparing the measured level to a reference level. The invention also provides methods of stratifying AD in an AD patient by comparing a measured value for BDNF, and, optionally, PDGF-BB, in a biological fluid sample, such as a peripheral biological fluid sample with a reference value. The invention further provides methods of stratifying AD in an AD patient by measuring BDNF and, optionally, PDGF-BB, in a biological fluid sample, such as a peripheral biological fluid sample. As described in Example 4, and under the experimental conditions disclosed in Example 4 which provide qualitative results, samples which have BDNF levels lower than the reference level suggest or indicate mild AD, while samples with BDNF levels higher than the reference level suggest more advanced AD (i.e., moderate or severe AD). Amongst those samples with BDNF levels higher than the reference level, those also having PDGF-BB levels below the reference level suggest or indicate moderate AD, while those samples also having PDGF-BB levels above the reference level suggest or indicate severe AD. It has been found that for Questionable AD (MMSE score in the range of 25-28) the levels of Leptin and PDGF-BB increase significantly whereas BDNF and RANTES do not change significantly. It has been found that from Mild AD (MMSE score in the range of 20-25) to Moderate AD (MMSE score in the range of 10-20) the level of LEPTIN does not decline whereas the levels for RANTES, BDNF and PDGF-BB declines. Accordingly, in some embodiments (as defined by the above MMSE scores from Example 7), Mild AD is indicated in quantitative assays when the levels of Leptin and/or PDGF-BB increase significantly whereas BDNF and RANTES do not change significantly as compared to Questionable AD as a reference. Accordingly, in some embodiments, (as defined by the above MMSE scores from Example 7), Moderate AD is indicated when Leptin does not decline whereas the levels for RANTES, BDNF and PDGF declines as compared to Mild AD as a reference. Accordingly, provided herein are methods comprising comparing measured values for RANTES and Leptin levels in a biological fluid sample from said patient with reference values for RANTES and Leptin; comparing measured values for brain derived neurotrophic factor (BDNF), Leptin, and RANTES, levels in a biological fluid sample from said patient with reference values for BDNF, Leptin, and RANTES; comparing measured values for Leptin and BB homodimeric platelet derived growth factor (PDGF-BB) levels in a biological fluid sample from said patient with reference values for Leptin and PDGF-BB. Accordingly, the present invention provides methods for stratifying Alzheimer's disease (AD) in an individual, comprising comparing measured values for brain derived neurotrophic factor (BDNF) and BB homodimeric platelet derived growth factor (PDGF-BB) levels in a biological fluid sample from said patient with reference values for BDNF and PDGF-BB. In some examples, the methods further comprise comparing measured values for leptin and Rantes levels with reference values for leptin and Rantes, wherein reference values for BDNF, PDGF-BB, leptin and Rantes are for samples from individuals with MMSE scores from 25 to 28, wherein an increase in leptin and PDGF-BB levels and wherein levels of BDNF and RANTES stay substantially the same indicate mild AD as indicated by an MMSE score of 20-25. The present invention also provides methods of further comprising comparing measured values for leptin and Rantes levels with reference values for leptin and Rantes, wherein reference values for BDNF, PDGF-BB, leptin and Rantes are for samples from individuals with MMSE scores from 20-25, wherein a decrease in Rantes, BDNF, and PDGF levels and wherein levels of Leptin stays substantially the same indicate moderate AD as indicated by an MMSE score of 10-20. An AD biomarker that stays "substantially the same" means that there is not a significant change, and that the values stay about the same. In some embodiments, substantially the same is a change less than any of about 12%, 10%, 5%, 2%, 1%. In some embodiments, a significant change means not statistically significant using standard methods in the art. The methods described above are also applicable to methods for assessing progression of AD. It is understood that the cognitive function indicated by the markers herein can be by other measurements with results or indicia that corresponds to approximately the same level of cognitive function as the MMSE scores provided herein.

The present invention also provides methods of aiding diagnosis of Alzheimer's disease ("AD"), comprising comparing a measured level of at least one AD diagnosis biomarker in a biological fluid sample from an individual to a reference level for the biomarker for each biomarker measured, wherein the at least one AD diagnosis biomarker is selected from Table 7 and has a statistically significant positive correlation with MMSE scores that is comparable to BDNF and/or Leptin correlation with MMSE scores, and wherein the at least one AD diagnosis biomarker is not statistically correlated with age. An AD diagnosis biomarker that has a statistically significant positive correlation with MMSE scores that is comparable to BDNF and/or leptin correlation with MMSE scores means that the biomarker is an AD diagnosis marker. In some examples, the AD diagnosis biomarker is selected from the group of biomarkers consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R and in other examples is selected from the group of biomarkers consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β).

The results of the comparison between the measured value(s) and the reference value(s) are used to diagnose or aid in the diagnosis of AD or MCI, to stratify AD patients according to the severity of their disease, or to monitor progression of AD in an AD patient. Accordingly, if the comparison indicates a difference between the measured value(s) and the reference value(s) that is suggestive/indicative of AD or MCI, then the appropriate diagnosis is aided in or made. Conversely, if the comparison of the measured level(s) to the reference level(s) does not indicate differences that suggest or indicate a diagnosis of AD or MCI, then the appropriate diagnosis is not aided in or made. Likewise, when comparison of a measured level for Leptin in a sample derived from an AD patient is decreased in comparison to the reference value, diagnosis of progression of the patient's AD is made or aided in. Similarly, when the comparison of levels of BDNF and PDGF-BB levels in a sample obtained from an AD patient indicates or suggests a particular stage of AD, the diagnosis of the particular stage of AD (mild, moderate or severe) is aided in or made.

As will be understood by those of skill in the art, when, in the practice of the AD diagnosis methods of the invention (i.e., methods of diagnosing or aiding in the diagnosis of AD), more than one AD diagnosis biomarker is used but the markers do not unanimously suggest or indicate a diagnosis of AD, the 'majority' suggestion or indication (e.g., when the method utilizes five AD diagnosis biomarkers, 3 of which suggest/indicate AD, the result would be considered as suggesting or indicating a diagnosis of AD for the individual) is considered the result of the assay. However, in some embodiments in which measured values for at least two AD diagnosis biomarkers are obtained and one of the measured values is for Leptin, the measured value for Leptin must be less than the reference value to indicate or suggest a diagnosis of AD. As will be appreciated by one of skill in the art, methods disclosed herein may include the use of any of a variety of biological markers (which may or may not be AD markers) to determine the integrity and/or characteristics of the biological sample(s). For example, Leptin levels, which are generally higher in females, may be measured as a marker of gender.

In certain embodiments of the invention, levels for AD biomarkers are obtained from an individual at more than one time point. Such "serial" sampling is well suited for the aspects of the invention related to monitoring progression of AD in an AD patient. Serial sampling can be performed on any desired timeline, such as monthly, quarterly (i.e., every three months), semi-annually, annually, biennially, or less frequently. The comparison between the measured levels and the reference level may be carried out each time a new sample is measured, or the data relating to levels may be held for less frequent analysis.

As will be understood by those of skill in the art, biological fluid samples including peripheral biological fluid samples are usually collected from individuals who are suspected of having AD, or developing AD or MCI. The invention also contemplates samples from individuals for whom cognitive assessment is desired. Alternatively, individuals (or others involved in for example research and/or clinicians may desire such assessments without any indication of AD, suspected AD, at risk for AD. For example, a normal individual may desire such information. Such individuals are most commonly 65 years or older, although individuals from whom biological fluid samples, such as peripheral biological fluid samples are taken for use in the methods of the invention may be as young as 35 to 40 years old, when early onset AD or familial AD is suspected.

The invention also provides methods of screening for candidate agents for the treatment of AD and/or MCI by assaying prospective candidate agents for activity in modulating AD biomarkers. The screening assay may be performed either in vitro and/or in vivo. Candidate agents identified in the screening methods described herein may be useful as therapeutic agents for the treatment of AD and/or MCI.

The probability P that the composite is more predictive than any subset of markers present in the composite can be expressed mathematically as:

$$P=1-(1-P_1)(1-P_2)(1-P_3)\ldots(1-P_n)$$

Where the probability $P_1$, $P_2$, $P_n$ represent the probability of individual marker being able to predict clinical phenotypes, and where $1-P_n$ represents the complement of that probability. Any subset of the composite, will always therefore have a smaller value for P.

In accordance with a further embodiment of the present invention, the relative concentrations in serum, CSF, or other fluids of the biomarkers cited in Table 7 as a composite, or collective, or any subset of such a composite, composed of 5 (five) or more elements is more predictive than the absolute concentration of any individual marker in predicting clinical phenotypes, disease detection, stratification, monitoring, and treatment of AD, PD, frontotemporal dementia, cerebrovascular disease, multiple sclerosis, and neuropathies.

AD Diagnosis Biomarkers

Immune mechanisms are an essential part of the host defense system and typically feature prominently in the inflammatory response. A growing number of studies are discovering intriguing links between the immune system and the CNS. For example, it has become clear that the CNS is not entirely sheltered from immune surveillance and that various immune cells can traverse the blood-brain barrier. Invading leukocytes can attack target antigens in the CNS or produce growth factors that might protect neurons against degeneration (Hohlfeld et al., 2000, *J. Neuroimmunol.* 107, 161-166). These responses are elicited through a variety of protein mediators, including but not limited to cytokines, chemokines, neurotrophic factors, collecting, kinins, and acute phase proteins in the immune and inflammatory systems, in intercellular communication across neurons, glial cells, endothelial cells and leukocytes. Without being bound by theory, it is hypothesized that the cytokines, chemokines, neurotrophic factors, collectins, kinins, and acute phase proteins listed in Table 7 are differentially expressed in serum associated with neurodegenerative and inflammatory diseases such as Alzheimer's, Parkinson's disease, Multiple Sclerosis, and neuropathies. Cytokines are a heterogeneous group of polypeptide mediators that have been associated with activation of numerous functions, including the immune system and inflammatory responses. Peripheral cytokines also penetrate the blood-brain barrier directly via active transport mechanisms or indirectly via vagal nerve stimulation. Cytokines can act in an autocrine manner, affecting the behavior of the cell that releases the cytokine, or in a paracrine manner, affecting the behavior of adjacent cells. Some cytokines can act in an endocrine manner, affecting the behavior of distant cells, although this depends on their ability to enter the circulation and on their half-life. The cytokine families include, but are not limited to, interleukins (IL-I alpha, IL-I beta, ILIra and IL-2 to IL-18), tumor necrosis factors (TNF-alpha and TNF-beta), interferons (INF-alpha, beta and gamma), colony stimulating factors (G-CSF, M-CSF, GM-CSF, IL-3 and some of the other ILs), and growth factors (EGF, FGF, PDGF, TGF alpha, TGF betas, BMPs, GDFs, CTGF, and ECGF).

The inventors have discovered a collection of biochemical markers present in peripheral bodily fluids that may be used to assess cognitive function, including diagnose or aid in the diagnosis of AD. These "AD diagnosis markers" include, but are not limited to GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, these "AD diagnosis biomarkers" are: basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, the AD diagnosis markers include one or more of Leptin, RANTES, PDFG-BB and BDNF.

The AD diagnosis biomarkers discovered by the inventors are all known molecules. Brain derived neurotrophic factor (BDNF) is described in, for example Rosenthal et al., 1991, Endocrinology 129(3):1289-94. Basic fibroblast growth factor (bFGF) is described in, for example Abraham et al., 1986, EMBO J. 5(10):2523-28. Epidermal growth factor (EGF) is described in, for example Gray et al., 1983, Nature 303(5919):722-25. Fibroblast growth factor 6 (FGF-6) is described in, for example Marics et al., 1989, Oncogene 4(3): 335-40. Interleukin-3 (IL-3) is described in, for example Yang et al., 1986, Cell 47(1):3-10. Soluble interleukin-6 receptor (sIL-6R) is described in, for example, Taga et al., 1989, Cell 58(3):573-81. Leptin (also known as "ob") is described in, for example Masuzaki et al. 1995, Diabetes 44(7): 855-58. Macrophage inflammatory protein-1 delta (MIP-1δ) is described in, for example Wang et al., 1998, J. Clin. Immunol. 18(3): 214-22. Macrophage stimulating protein alpha chain (MSP-α) is described in, for example, Yoshimura et al., 1993, J. Biol. Chem. 268 (21), 15461-68, and Yoshikawa et al., 1999, Arch. Biochem. Biophys. 363(2):356-60. Neutrophil activating peptide-2 (NAP-2) is described in, for example Walz et al., 1991, Adv. Exp. Med. Biol. 305:39-46. Neurotrophin-3 (NT-3) is described in, for example Hohn et al., 1990, Nature 344 (6264):339-41. BB homodimeric platelet derived growth factor (PDGF-BB) is described in, for example Collins et al., 1985, Nature 316(6030):748-50. RANTES is described in, for example Schall et al., 1988, J. Immunol. 141(3):1018-25. Stem cell factor (SCF) is described in, for example Zseboet al., 1990, Cell 63(1):213-24. Soluble tumor necrosis factor receptor-2 (sTNF RII) is described in, for example Schall et al., 1990, Cell 61(2):361-70. Transforming growth factor-beta 3 (TGF-#3) is described in, for example ten Dijke et al., 1988, Proc. Natl. Acad. Sci. U.S.A. 85 (13):4715-19. Tissue inhibitor of metalloproteases-1 (TIMP-1) is described in, for example, Docherty et al., 1985, Nature 318(6041):66-69 and Gasson et al., 1985, Nature 315(6022):768-71. Tissue inhibitor of metalloproteases-2 (TIMP-2) is described in, for example, Stetler-Stevenson et al., 1190, J. Biol. Chem. 265 (23):13933-38. Tumor necrosis factor beta (TNF-β) is described in, for example Gray et al., 1984, Nature 312(5996):721-24. Thrombopoietin (TPO) is described in, for example, Foster et al., 1994, Proc. Natl. Acad. Sci. U.S.A. 91(26):13023-27.

Although the inventors have found acceptable levels of sensitivity and specificity with single AD diagnosis biomarkers for practice of the AD diagnosis methods, the effectiveness (e.g., sensitivity and/or specificity) of the methods of the AD diagnosis methods of the instant invention are generally enhanced when at least two AD diagnosis biomarkers are utilized. In some examples, the methods of the AD diagnosis methods of the instant invention are generally enhanced when at least four AD diagnosis biomarkers are utilized. Multiple AD diagnosis biomarkers may be selected from the AD diagnosis biomarkers disclosed herein by a variety of methods, including "q value" and/or by selecting for cluster diversity. AD diagnosis biomarkers may be selected on the basis of "q value", a statistical value that the inventors derived when identifying the AD diagnosis biomarkers (see Table 3 in Example 1). "q values" for selection of AD diagnosis biomarkers range from less than about 0.0001 to about 0.05 and in some examples, range from about 0.01 to about 0.05. Alternately (or additionally), AD diagnosis biomarkers may be selected to preserve cluster diversity. The inventors have separated the AD diagnosis biomarkers into a number of clusters (see Table 1). Here the clusters are formed by qualitative measurements for each biomarker which are most closely correlated. As used herein, "correlate" or "correlation" is a simultaneous change in value of two numerically valued random variables such as MMSE scores and quantitative protein concentrations or qualitative protein concentrations. As used herein "discriminate" or "discriminatory" is refers to the quantitative or qualitative difference between two or more samples for a given variable. The cluster next to such a cluster is a cluster that is most closely correlated with the cluster. The correlations between biomarkers and between clusters can represented by a hierarchical tree generated by unsupervised clustering using a public web based software called wCLUTO available at: cluto.ccgb.umn.edu/cgi-bin/wCluto/wCluto.cgi. If more than one AD diagnosis biomarker is selected for testing, in some examples, the AD diagnosis biomarkers selected are at least partially diverse (i.e., the AD diagnosis biomarkers represent at least two different clusters, for example, a set of AD diagnosis biomarkers comprising Leptin, BDNF and/or PDGF-BB from cluster 4 in Table 1 and RANTES from cluster 3 of Table 1), and in some instances the AD diagnosis biomarkers are completely diverse (i.e. no two of the selected AD diagnosis biomarkers are from the same cluster). Accordingly, the invention provides a number of different embodiments for diagnosing or aiding in the diagnosis of AD.

TABLE 1

| Cluster | Biomarker |
|---------|-----------|
| 0 | bFGF |
| 1 | TPO |
| 2 | FGF-6 |
|   | IL-3 |
|   | sIL-6 R |
|   | MIP-1d |
|   | sTNF RII |
|   | TNF-b |
| 3 | RANTES |
|   | TIMP-1 |
|   | TIMP-2 |
| 4 | BDNF |
|   | EGF |
|   | LEPTIN(OB) |
|   | MSP-α |
|   | NAP-2 |
|   | NT-3 |
|   | PDGF-BB |
|   | SCF |
|   | TGF-b3 |

In some embodiments, the level of a single AD diagnosis biomarker in a peripheral biological fluid sample is obtained and the measured level is compared to a reference level to diagnose or aid in diagnosing AD. In certain embodiments where measured level for a single AD diagnosis biomarker is obtained for the practice of the invention, the measured level is for RANTES in the peripheral biological fluid sample.

In other embodiments, the levels of at least two AD diagnosis biomarkers in a peripheral biological fluid sample are obtained and compared to reference levels for each of the markers. Accordingly, the invention provides methods for diagnosing and/or aiding in the diagnosis of AD by measuring the levels of at least 2, 3, 4, 5, 6, 7, 8, 9, 10, 11, 12, 15, or 20 AD diagnosis biomarkers and comparing the measured levels with reference levels. Exemplary embodiments utilize 2, 3, 4, or 5 AD diagnosis biomarkers. In some embodiments, provided herein are methods for diagnosing and/or aiding in the diagnosis of AD by measuring the levels of at least Leptin, RANTES, BDGF, and PDGF-BB.

For those embodiments which utilize more than one AD diagnosis biomarker (i.e., those embodiments in which measured values are obtained for more than one AD diagnosis biomarker), exemplary combinations of AD diagnosis biomarkers shown in Table 3 include (1) Leptin in combination with any of the other AD diagnosis biomarkers (i.e., Leptin and BDNF, Leptin and bFGF, Leptin and EGF, Leptin and FGF-6, Leptin and IL-3, Leptin and sIL-6R, Leptin and MIP- 1δ, Leptin and MSP-α, Leptin and NAP-2, Leptin and NT-3, Leptin and PDGF-BB, Leptin and RANTES, Leptin and SCF, Leptin and sTNR RII, Leptin and TGF-β3, Leptin and TIMP-1, Leptin and TIMP-2, Leptin and TNF-β, and Leptin and TPO), (2) RANTES in combination with any of the other AD diagnosis biomarkers (i.e., RANTES and BDNF, RANTES and bFGF, RANTES and EGF, RANTES and FGF-6, RANTES and IL-3, RANTES and sIL-6R, RANTES and Leptin, RANTES and MIP-1δ, RANTES and MSP-α, RANTES and NAP-2, RANTES and NT-3, RANTES and PDGF-BB, RANTES and SCF, RANTES and sTNR RII, RANTES and TGF-β3, RANTES and TIMP-1, RANTES and TIMP-2, RANTES and TNF-β, and RANTES and TPO); (3) PDGF-BB and any of the other AD diagnosis biomarkers (i.e., PDGF-BB and BDNF, PDGF-BB and bFGF, PDGF-BB and EGF, PDGF-BB and FGF-6, PDGF-BB and IL-3, PDGF-BB and sIL-6R, PDGF-BB and Leptin, PDGF-BB and MIP-1δ, PDGF-BB and MSP-α, PDGF-BB and NAP-2, PDGF-BB and NT-3, PDGF-BB and RANTES, PDGF-BB and SCF, PDGF-BB and sTNR RII, PDGF-BB and TGF-β3, PDGF-BB and TIMP-1, PDGF-BB and TIMP-2, PDGF-BB and TNF-β, and PDGF-BB and TPO); (4) BDNF in combination with any of the other AD diagnosis biomarkers (i.e., BDNF and bFGF, BDNF and EGF, BDNF and FGF-6, BDNF and IL-3, BDNF and sIL-6R, BDNF and Leptin, BDNF and MIP-1δ, BDNF and MSP-α, BDNF and NAP-2, BDNF and NT-3, BDNF and PDGF-BB, BDNF and RANTES, BDNF and SCF, BDNF and sTNR RII, BDNF and TGF-β3, BDNF and TIMP-1, BDNF and TIMP-2, BDNF and TNF-β, and BDNF and TPO); (5) RANTES, PDGF-BB, and NT-3; (6) Leptin, PDGF-BB, and RANTES; (7) BDNF, PDGF-BB, and RANTES; (8) BDNF, Leptin, and RANTES; (9) BDNF, Leptin, and PDGF-BB; (10) PDGF-BB, EGF, and NT-3; (11) PDGF-BB, NT 3, and Leptin; (12) BDNF, Leptin, PDGF-BB, RANTES; and (13) RANTES, PDGF-BB, NT-3, EGF, NAP-2, and Leptin. Additional exemplary combinations of AD diagnosis biomarkers include (14) Leptin in combination with any of the other AD diagnosis biomarkers disclosed herein (i.e., Leptin and GCSF, Leptin and IFN-γ, Leptin and IGFBP-1, Leptin and BMP-6, Leptin and BMP-4, Leptin and Eotaxin-2, Leptin and IGFBP-2, Leptin and TARC, Leptin and ANG, Leptin and PARC, Leptin and Acrp30, Leptin and AgRP(ART), Leptin and ICAM-1, Leptin and TRAIL R3, Leptin and uPAR, Leptin and IGFBP-4, Leptin and IL-1Ra, Leptin and AXL, Leptin and FGF-4, Leptin and CNTF, Leptin and MCP-1, Leptin and MIP 1b, Leptin and VEGF-B, Leptin and IL-8, Leptin and FAS and Leptin and EGF-R), (15) RANTES in combination with any of the other AD diagnosis biomarkers disclosed herein (i.e., RANTES and GCSF, RANTES and IFN-γ, RANTES and IGFBP-1, RANTES and BMP-6, RANTES and BMP-4, RANTES and Eotaxin-2, RANTES and IGFBP-2, RANTES and TARC, RANTES and ANG, RANTES and PARC, RANTES and Acrp30, RANTES and AgRP(ART), RANTES and ICAM-1, RANTES and TRAIL R3, RANTES and uPAR, RANTES and IGFBP-4, RANTES and IL-1Ra, RANTES and AXL, RANTES and FGF-4, RANTES and CNTF, RANTES and MCP-1, RANTES and MIP1b, RANTES and VEGF-B, RANTES and IL-8, RANTES and FAS and RANTES and EGF-R), (16) PDGF-BB in combination with any of the other AD diagnosis biomarkers disclosed herein (i.e., PDGF-BB and GCSF, PDGF-BB and IFN-γ, PDGF-BB and IGFBP-1, PDGF-BB and BMP-6, PDGF-BB and BMP-4, PDGF-BB and Eotaxin-2, PDGF-BB and IGFBP-2, PDGF-BB and TARC, PDGF-BB and ANG, PDGF-BB and PARC, PDGF-BB and Acrp30, PDGF-BB and AgRP(ART), PDGF-BB and ICAM-1, PDGF-BB and TRAIL R3, PDGF-BB and uPAR, PDGF-BB and IGFBP-4, PDGF-BB and IL-1Ra, PDGF-BB and AXL, PDGF-BB and FGF-4, PDGF-BB and CNTF, PDGF-BB and MCP-1, PDGF-BB and MIP1b, PDGF-BB and VEGF-B, PDGF-BB and IL-8, PDGF-BB and FAS and PDGF-BB and EGF-R), (17) BDNF in combination with any of the other AD diagnosis biomarkers disclosed herein (i.e., BDNF and GCSF, BDNF and IFN-γ, BDNF and IGFBP-1, BDNF and BMP-6, BDNF and BMP-4, BDNF and Eotaxin-2, BDNF and IGFBP-2, BDNF and TARC, BDNF and ANG, BDNF and PARC, BDNF and Acrp30, BDNF and AgRP (ART), BDNF and ICAM-1, BDNF and TRAIL R3, BDNF and uPAR, BDNF and IGFBP-4, BDNF and IL-1Ra, BDNF and AXL, BDNF and FGF-4, BDNF and CNTF, BDNF and MCP-1, BDNF and MIP1b, BDNF and VEGF-B, BDNF and IL-8, BDNF and FAS and BDNF and EGF-R).

Measuring Levels of AD Biomarkers

There are a number of statistical tests for identifying biomarkers which vary significantly between the subsets, including the conventional t test. However, as the number of biomarkers measured increases, it is generally advantageous to use a more sophisticated technique, such as SAM (see Tusher et al., 2001, *Proc. Natl. Acad. Sci. U.S.A.* 98(9):5116-21). Other useful techniques include Tree Harvesting (Hastie et al., *Genome Biology* 2001, 2:research0003.1-0003.12), Self Organizing Maps (Kohonen, 1982b, *Biological Cybernetics* 43(1):59-69), Frequent Item Set (Agrawal et al., 1993 "Mining association rules between sets of items in large databases." In Proc. of the ACM SIGMOD Conference on Management of Data, pages 207--216, Washington, D.C., May 1993), Bayesian networks (Gottardo, Statistical analysis of microarray data, A Bayesian approach. Biostatistics (2001), 1,1, pp 1-37), and the commercially available software packages CART and MARS.

The SAM technique assigns a score to each biomarker on the basis of change in expression relative to the standard deviation of repeated measurements. For biomarkers with scores greater than an adjustable threshold, the algorithm uses permutations of the repeated measurements to estimate the probability that a particular biomarker has been identified by chance (calculated as a "q-value"), or a false positive rate which is used to measure accuracy. The SAM technique can be carried out using publicly available software called Significance Analysis of Microarrays (see www-stat class.stanford.edu/~tibs/clickwrap/sam.html).

A biomarkers is considered "identified" as being useful for aiding in the diagnosis, diagnosis, stratification, monitoring, and/or prediction of neurological disease when it is significantly different between the subsets of peripheral biological samples tested. Levels of a biomarker are "significantly different" when the probability that the particular biomarker has been identified by chance is less than a predetermined value. The method of calculating such probability will depend on the exact method utilizes to compare the levels between the subsets (e.g., if SAM is used, the q-value will give the probability of misidentification, and the p value will give the probability if the t test (or similar statistical analysis) is used). As will be understood by those in the art, the predetermined value will vary depending on the number of biomarkers measured per sample and the number of samples utilized. Accordingly, predetermined value may range from as high as 50% to as low as 20, 10, 5, 3, 2, or 1%.

As described herein, the level of at least one AD diagnosis biomarker is measured in a biological sample from an individual. The AD biomarker level(s) may be measured using any available measurement technology that is capable of specifically determining the level of the AD biomarker in a biological sample. The measurement may be either quantitative or qualitative, so long as the measurement is capable of indicating whether the level of the AD biomarker in the peripheral biological fluid sample is above or below the reference value.

The measured level may be a primary measurement of the level a particular biomarker a measurement of the quantity of biomarker itself (quantitative data, such as in Example 7), such as by detecting the number of biomarker molecules in the sample) or it may be a secondary measurement of the biomarker (a measurement from which the quantity of the biomarker can be but not necessarily deduced (qualitative data, such as Example 4), such as a measure of enzymatic activity (when the biomarker is an enzyme) or a measure of mRNA coding for the biomarker). Qualitative data may also be derived or obtained from primary measurements.

Although some assay formats will allow testing of peripheral biological fluid samples without prior processing of the sample, it is expected that most peripheral biological fluid samples will be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood. In some examples, the peripheral biological fluid sample is collected in a container comprising EDTA.

Commonly, AD biomarker levels will be measured using an affinity-based measurement technology. "Affinity" as relates to an antibody is a term well understood in the art and means the extent, or strength, of binding of antibody to the binding partner, such as an AD diagnosis biomarker as described herein (or epitope thereof). Affinity may be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to effect 50% inhibition in a competition assay; used interchangeably herein with "$I_{50}$"). It is understood that, for purposes of this invention, an affinity is an average affinity for a given population of antibodies which bind to an epitope. Values of $K_D'$ reported herein in terms of mg IgG per ml or mg/ml indicate mg Ig per ml of serum, although plasma can be used.

Affinity-based measurement technology utilizes a molecule that specifically binds to the AD biomarker being measured (an "affinity reagent," such as an antibody or aptamer), although other technologies, such as spectroscopy-based technologies (e.g., matrix-assisted laser desorption ionization-time of flight, or MALDI-TOF, spectroscopy) or assays measuring bioactivity (e.g., assays measuring mitogenicity of growth factors) may be used.

Affinity-based technologies include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection).

If immunoassay technology is employed, any immunoassay technology which can quantitatively or qualitatively measure the level of a AD biomarker in a biological sample may be used. Suitable immunoassay technology includes radioimmunoassay, immunofluorescent assay, enzyme immunoassay, chemiluminescent assay, ELISA, immuno-PCR, and western blot assay.

Likewise, aptamer-based assays which can quantitatively or qualitatively measure the level of a AD biomarker in a biological sample may be used in the methods of the invention. Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

A wide variety of affinity-based assays are known in the art. Affinity-based assays will utilize at least one epitope derived from the AD biomarker of interest, and many affinity-based assay formats utilize more than one epitope (e.g., two or more epitopes are involved in "sandwich" format assays; at least one epitope is used to capture the marker, and at least one different epitope is used to detect the marker).

Affinity-based assays may be in competition or direct reaction formats, utilize sandwich-type formats, and may further be heterogeneous (e.g., utilize solid supports) or homogenous (e.g., take place in a single phase) and/or utilize or immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays. Herein, the examples referred to as "quantitative data" the biomarker concentrations were obtained using ELISA. Either of the biomarker or reagent specific for the biomarker can be attached to a surface and levels can be measured directly or indirectly.

In a heterogeneous format, the assay utilizes two phases (typically aqueous liquid and solid). Typically an AD biomarker-specific affinity reagent is bound to a solid support to facilitate separation of the AD biomarker from the bulk of the biological sample. After reaction for a time sufficient to allow for formation of affinity reagent/AD biomarker complexes, the solid support or surface containing the antibody is typically washed prior to detection of bound polypeptides. The affinity reagent in the assay for measurement of AD biomarkers may be provided on a support (e.g., solid or semi-solid); alternatively, the polypeptides in the sample can be immobilized on a support or surface. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, glass and Protein A beads. Both standard and competitive formats for these assays are known in the art. Accordingly, the provided herein are complexes comprising at least one AD diagnosis biomarker bound to a reagent specific for the biomarker, wherein said reagent is attached to a surface. Also provided herein are complexes comprising at least one AD diagnosis biomarker bound to a reagent specific for the biomarker, wherein said biomarker is attached to a surface.

Array-type heterogeneous assays are suitable for measuring levels of AD biomarkers when the methods of the invention are practiced utilizing multiple AD biomarkers. Array-type assays used in the practice of the methods of the invention will commonly utilize a solid substrate with two or more capture reagents specific for different AD biomarkers bound to the substrate a predetermined pattern (e.g., a grid). The peripheral biological fluid sample is applied to the substrate and AD biomarkers in the sample are bound by the capture reagents. After removal of the sample (and appropriate washing), the bound AD biomarkers are detected using a mixture of appropriate detection reagents that specifically bind the various AD biomarkers. Binding of the detection reagent is commonly accomplished using a visual system, such as a fluorescent dye-based system. Because the capture reagents are arranged on the substrate in a predetermined pattern, array-type assays provide the advantage of detection of multiple AD biomarkers without the need for a multiplexed detection system.

In a homogeneous format the assay takes place in single phase (e.g., aqueous liquid phase). Typically, the biological sample is incubated with an affinity reagent specific for the AD biomarker in solution. For example, it may be under conditions that will precipitate any affinity reagent/antibody complexes which are formed. Both standard and competitive formats for these assays are known in the art.

In a standard (direct reaction) format, the level of AD biomarker/affinity reagent complex is directly monitored. This may be accomplished by, for example, determining the amount of a labeled detection reagent that forms is bound to AD biomarker/affinity reagent complexes. In a competitive format, the amount of AD biomarker in the sample is deduced by monitoring the competitive effect on the binding of a known amount of labeled AD biomarker (or other competing ligand) in the complex. Amounts of binding or complex formation can be determined either qualitatively or quantitatively.

The methods described in this patent may be implemented using any device capable of implementing the methods. Examples of devices that may be used include but are not limited to electronic computational devices, including computers of all types. When the methods described in this patent are implemented in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods may also be provided over an electronic network, for example, over the internet, world wide web, an intranet, or other network.

In one example, the methods described in this patent may be implemented in a system comprising a processor and a computer readable medium that includes program code means for causing the system to carry out the steps of the methods described in this patent. The processor may be any processor capable of carrying out the operations needed for implementation of the methods. The program code means may be any code that when implemented in the system can cause the system to carry out the steps of the methods described in this patent. Examples of program code means include but are not limited to instructions to carry out the methods described in this patent written in a high level computer language such as C++, Java, or Fortran; instructions to carry out the methods described in this patent written in a low level computer language such as assembly language; or instructions to carry out the methods described in this patent in a computer executable form such as compiled and linked machine language.

Complexes formed comprising AD biomarker and an affinity reagent are detected by any of a number of known techniques known in the art, depending on the format of the assay and the preference of the user. For example, unlabelled affinity reagents may be detected with DNA amplification technology (e.g., for aptamers and DNA-labeled antibodies) or labeled "secondary" antibodies which bind the affinity reagent. Alternately, the affinity reagent may be labeled, and the amount of complex may be determined directly (as for dye-(fluorescent or visible), bead-, or enzyme-labeled affinity reagent) or indirectly (as for affinity reagents "tagged" with biotin, expression tags, and the like). Herein the examples provided referred to as "qualitative data" filter based antibody arrays using chemiluminesense were used to obtain measurements for biomarkers.

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one AD biomarker is measured, the biological sample may be divided into a number of aliquots, with separate aliquots used to measure different AD biomarkers (although division of the biological sample into multiple aliquots to allow multiple determinations of the levels of the AD biomarker in a particular sample are also contemplated). Alternately the biological sample (or an aliquot therefrom) may be tested to determine the levels of multiple AD biomarkers in a single reaction using an assay capable of measuring the individual levels of different AD biomarkers in a single assay, such as an array-type assay or assay utilizing multiplexed detection technology (e.g., an assay utilizing detection reagents labeled with different fluorescent dye markers).

It is common in the art to perform 'replicate' measurements when measuring biomarkers. Replicate measurements are ordinarily obtained by splitting a sample into multiple aliquots, and separately measuring the biomarker(s) in separate reactions of the same assay system. Replicate measurements are not necessary to the methods of the invention, but many embodiments of the invention will utilize replicate testing, particularly duplicate and triplicate testing.

Reference Levels

The reference level used for comparison with the measured level for a AD biomarker may vary, depending on aspect of the invention being practiced, as will be understood from the foregoing discussion. For AD diagnosis methods, the "reference level" is typically a predetermined reference level, such as an average of levels obtained from a population that is not afflicted with AD or MCI, but in some instances, the reference level can be a mean or median level from a group of individuals including AD patients. In some instances, the predetermined reference level is derived from (e.g., is the mean or median of) levels obtained from an age-matched population.

For MCI diagnosis methods (i.e., methods of diagnosing or aiding in the diagnosis of MCI), the reference level is typically a predetermined reference level, such as an average of levels obtained from a population that is not afflicted with AD or MCI, but in some instances, the reference level can be a mean or median level from a group of individuals including MCI and/or AD patients. In some instances, the predetermined reference level is derived from (e.g., is the mean or median of) levels obtained from an age-matched population.

For AD monitoring methods (e.g., methods of diagnosing or aiding in the diagnosis of AD progression in an AD patient), the reference level may be a predetermined level, such as an average of levels obtained from a population that is not afflicted with AD or MCI, a population that has been diagnosed with MCI or AD, and, in some instances, the reference level can be a mean or median level from a group of individuals including MCI and/or AD patients. Alternately, the reference level may be a historical reference level for the particular patient (e.g., a Leptin level that was obtained from a sample derived from the same individual, but at an earlier point in time). In some instances, the predetermined reference level is derived from (e.g., is the mean or median of) levels obtained from an age-matched population.

For AD stratification methods (i.e., methods of stratifying AD patients into mild, moderate and severe stages of AD), the reference level is normally a predetermined reference level that is the mean or median of levels from a population which has been diagnosed with AD or MCI (preferably a population diagnosed with AD) In some instances, the predetermined reference level is derived from (e.g., is the mean or median of) levels obtained from an age-matched population.

Age-matched populations (from which reference values may be obtained) are ideally the same age as the individual being tested, but approximately age-matched populations are also acceptable. Approximately age-matched populations may be within 1, 2, 3, 4, or 5 years of the age of the individual tested, or may be groups of different ages which encompass the age of the individual being tested. Approximately age-matched populations may be in 2, 3, 4, 5, 6, 7, 8, 9, or 10 year increments (e.g. a "5 year increment" group which serves as the source for reference values for a 62 year old individual might include 58-62 year old individuals, 59-63 year old individuals, 60-64 year old individuals, 61-65 year old individuals, or 62-66 year old individuals).

Comparing Levels of AD Biomarkers

The process of comparing a measured value and a reference value can be carried out in any convenient manner appropriate to the type of measured value and reference value for the AD biomarker at issue. As discussed above, 'measuring' can be performed using quantitative or qualitative measurement techniques, and the mode of comparing a measured value and a reference value can vary depending on the measurement technology employed. For example, when a qualitative calorimetric assay is used to measure AD biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration, such as nanograms of AD biomarker per milliliter of sample, or absolute amount). As with qualitative measurements, the comparison can be made by inspecting the numerical data, by inspecting representations of the data (e.g., inspecting graphical representations such as bar or line graphs).

A measured value is generally considered to be substantially equal to or greater than a reference value if it is at least 95% of the value of the reference value (e.g., a measured value of 1.71 would be considered substantially equal to a reference value of 1.80). A measured value is considered less than a reference value if the measured value is less than 95% of the reference value (e.g., a measured value of 1.7 would be considered less than a reference value of 1.80).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for an AD biomarker. Alternately, a separate device (e.g., a digital computer) may be used to compare the measured value(s) and the reference value(s). Automated devices for comparison may include stored reference values for the AD biomarker(s) being measured, or they may compare the measured value(s) with reference values that are derived from contemporaneously measured reference samples.

In some embodiments, the methods of the invention utilize 'simple' or 'binary' comparison between the measured level(s) and the reference level(s) (e.g., the comparison between a measured level and a reference level determines whether the measured level is higher or lower than the reference level). For AD diagnosis biomarkers, a comparison showing that the measured value for the biomarker is lower than the reference value indicates or suggests a diagnosis of AD. For methods relating to the diagnosis of MCI, a comparison showing that measured value for RANTES is lower than the reference value indicates or suggests a diagnosis of AD. In those embodiments relating to diagnosis of MCI which additionally utilize a measured value for Leptin, a comparison showing that RANTES is less than the reference value while Leptin is substantially equal to or greater than the reference level suggests or indicates a diagnosis of MCI.

As described herein, biological fluid samples may be measured quantitatively (absolute values) or qualitatively (relative values). The respective AD biomarker levels for a given assessment may or may not overlap. As described herein, for some embodiments, qualitative data indicate a given level of cognitive impairment (mild, moderate or severe AD) (which can be measured by MMSE scores) and in other embodiments, quantitative data indicate a given level of cognitive impairment. A shown in Example 4 and under the conditions provided in Example 4 (qualitative data), in those embodiments relating to stratification of AD, a comparison which shows BDNF levels lower than the reference level suggests or indicates mild AD, while a comparison which shows BDNF levels higher than the reference level suggests more advanced AD (i.e., moderate or severe AD), and amongst those samples with BDNF levels higher than the reference level, those also having PDGF-BB levels below the reference level suggest or indicate moderate AD, while those samples also having PDGF-BB levels above the reference level suggest or indicate severe AD. In those embodiments relating to stratification of AD shown in Example 7 (quantitative data), a comparison which shows BDNF levels lower than the reference level where the reference level is Normal suggests or indicates mild AD, while a comparison which shows BDNF levels lower than the reference level where the reference level is Mild AD suggests more advanced AD (i.e., moderate, severe AD), while those samples with leptin levels equal to the reference level where the reference level is Mild AD, those having RANTES levels below the reference level suggest or indicate moderate AD, while those samples with leptin levels equal to the reference level where the reference level is Moderate AD those having PDGF-BB, RANTES, or BDNF levels lower than the reference level suggest or indicate severe AD.

However, in certain aspects of the invention, the comparison is performed to determine the magnitude of the difference between the measured and reference values (e.g., comparing the 'fold' or percentage difference between the measured value and the reference value). A fold difference that is about equal to or greater than the minimum fold difference disclosed herein suggests or indicates a diagnosis of AD, MCI, progression from MCI to AD, or progression from mild AD to moderate AD, as appropriate to the particular method being practiced. A fold difference can be determined by measuring the absolute concentration of a protein and comparing that to the absolute value of a reference, or a fold difference can be measured by the relative difference between a reference value and a sample value, where neither value is a measure of absolute concentration, and/or where both values are measured simultaneously. A fold difference and be in the range of 10% to 95%. An ELISA measures the absolute content or concentration of a protein from which a fold change is determined in comparison to the absolute concentration of the same protein in the reference. An antibody array measures the relative concentration from which a fold change is determined. Accordingly, the magnitude of the difference between the measured value and the reference value that suggests or indicates a particular diagnosis will depend on the particular AD biomarker being measured to produce the measured value and the reference value used (which in turn depends on the method being practiced). Tables 2A-2B list minimum fold difference values for AD biomarkers for use in methods of the invention which utilize a fold difference in making the comparison between the measured value and the reference value. In those embodiments utilizing fold difference values, a fold difference of about the fold difference indicated in Table 2A suggests a diagnosis of AD, wherein the fold change is a negative value. For example, as described herein, BDNF levels (as measured by ELISA) are decreased in AD patients with mild AD, and BDNF levels decrease further as the severity of the AD intensifies. As shown in Table 6, a BDNF fold change of −46% means a reduction of BDNF levels by 46%. As shown in Table 2A, for qualitative measurements using antibodies, a BDNF fold change of 0.60 means a reduction in BDNF levels by about 60%. Table 2B provides additional information regarding fold changes.

TABLE 2A

| Biomarker | Fold Change (as negative value or decrease) |
|---|---|
| BDNF | 0.60 |
| bFGF | 0.75 |
| EGF | 0.60 |
| FGF-6 | 0.70 |
| IL-3 | 0.80 |
| sIL-6 R | 0.75 |
| Leptin | 0.55 |
| MIP-1δ | 0.60 |
| MSP-α | 0.80 |
| NAP-2 | 0.75 |
| NT-3 | 0.75 |
| PDGF-BB | 0.60 |
| RANTES | 0.75 |
| SCF | 0.80 |
| sTNF RII | 0.75 |
| TGF-β3 | 0.80 |
| TIMP-1 | 0.75 |
| TIMP-2 | 0.80 |
| TNF-β | 0.70 |
| TPO | 0.75 |

TABLE 2B

| Protein | Relative Fold Change (n = 51) | q-value | Absolute Fold Change (n = 187) | p-value |
|---|---|---|---|---|
| MIP-1d | −0.54291 | 0.0165 | | |
| PDGF-BB | −0.53687 | 0.0165 | −0.135 | 0.891 |
| LEPTIN(OB) | −0.47625 | 0.0165 | −0.357 | 0.0018 |
| IL-6 R | −0.6763 | 0.0165 | | |
| BDNF | −0.53628 | 0.0165 | −0.355 | 0.0006 |
| TIMP-1 | −0.71622 | 0.0165 | | |
| RANTES | −0.68299 | 0.0165 | −0.184 | 0.0144 |
| EGF | −0.56182 | 0.0165 | | |

TABLE 2B-continued

| Protein | Relative Fold Change (n = 51) | q-value | Absolute Fold Change (n = 187) | p-value |
|---|---|---|---|---|
| TIMP-2 | −0.75011 | 0.0165 | | |
| NAP-2 | −0.67257 | 0.0165 | | |
| sTNF RII | −0.70029 | 0.0165 | | |
| TNF-b | −0.64998 | 0.0165 | | |
| TPO | −0.71405 | 0.0165 | | |
| FGF-6 | −0.66467 | 0.0165 | | |
| NT-3 | −0.69805 | 0.0165 | | |
| bFGF | −0.67351 | 0.0165 | | |
| IL-3 | −0.75802 | 0.0165 | | |
| SCF | −0.73041 | 0.0165 | | |
| TGF-b3 | −0.76912 | 0.0165 | | |
| MSP-a | −0.76466 | 0.0165 | | |

As will be apparent to those of skill in the art, when replicate measurements are taken for the biomarker(s) tested, the measured value that is compared with the reference value is a value that takes into account the replicate measurements. The replicate measurements may be taken into account by using either the mean or median of the measured values as the "measured value."

Screening Prospective Agents for AD Biomarker Modulation Activity

The invention also provides methods of screening for candidate agents for the treatment of AD and/or MCI by assaying prospective candidate agents for activity in modulating AD biomarkers. The screening assay may be performed either in vitro and/or in vivo. Candidate agents identified in the screening methods described herein may be useful as therapeutic agents for the treatment of AD and/or MCI.

The screening methods of the invention utilize the AD biomarkers described herein and AD biomarker polynucleotides as "drug targets." Prospective agents are tested for activity in modulating a drug target in an assay system. As will be understood by those of skill in the art, the mode of testing for modulation activity will depend on the AD biomarker and the form of the drug target used (e.g., protein or gene). A wide variety of suitable assays are known in the art.

When the AD biomarker protein itself is the drug target, prospective agents are tested for activity in modulating levels or activity of the protein itself. Modulation of levels of an AD biomarker can be accomplished by, for example, increasing or reducing half-life of the biomarker protein. Modulation of activity of an AD biomarker can be accomplished by increasing or reducing the availability of the AD biomarker to bind to its cognate receptor(s) or ligand(s).

When an AD biomarker polynucleotide is the drug target, the prospective agent is tested for activity in modulating synthesis of the AD biomarker. The exact mode of testing for modulatory activity of a prospective agent will depend, of course, on the form of the AD biomarker polynucleotide selected for testing. For example, if the drug target is an AD biomarker polynucleotide, modulatory activity is typically tested by measuring either mRNA transcribed from the gene (transcriptional modulation) or by measuring protein produced as a consequence of such transcription (translational modulation). As will be understood by those in the art, many assay formats will utilize a modified form of the AD biomarker gene where a heterologous sequence (e.g., encoding an expression marker such as an enzyme or an expression tag such as oligo-histidine or a sequence derived from another protein, such as myc) is fused to (or even replaces) the sequence encoding the AD biomarker protein. Such heterologous sequence(s) allow for convenient detection of levels of protein transcribed from the drug target.

Prospective agents for use in the screening methods of the invention may be chemical compounds and/or complexes of any sort, including both organic and inorganic molecules (and complexes thereof). As will be understood in the art, organic molecules are most commonly screened for AD biomarker modulatory activity. In some situations, the prospective agents for testing will exclude the target AD biomarker protein.

Screening assays may be in any format known in the art, including cell-free in vitro assays, cell culture assays, organ culture assays, and in vivo assays (i.e., assays utilizing animal models of AD and MCI). Accordingly, the invention provides a variety of embodiments for screening prospective agents to identify candidate agents for the treatment of AD and/or MCI.

In some embodiments, prospective agents are screened to identify candidate agents for the treatment of AD and/or MCI in a cell-free assay. Each prospective agent is incubated with the drug target in a cell-free environment, and modulation of the AD biomarker is measured. Cell-free environments useful in the screening methods of the invention include cell lysates (particularly useful when the drug target is an AD biomarker gene) and biological fluids such as whole blood or fractionated fluids derived therefrom such as plasma and serum (particularly useful when the AD biomarker protein is the drug target). When the drug target is an AD biomarker gene, the modulation measured may be modulation of transcription or translation. When the drug target is the AD biomarker protein, the modulation may of the half-life of the protein or of the availability of the AD biomarker protein to bind to its cognate receptor or ligand.

In other embodiments, prospective agents are screened to identify candidate agents for the treatment of AD and/or MCI in a cell-based assay. Each prospective agent is incubated with cultured cells, and modulation of target AD biomarker is measured. In certain embodiments, the cultured cells are astrocytes, neuronal cells (such as hippocampal neurons), fibroblasts, or glial cells. When the drug target is an AD biomarker gene, transcriptional or translational modulation may be measured. When the drug target is the AD biomarker protein, the AD biomarker protein is also added to the assay mixture, and modulation of the half-life of the protein or of the availability of the AD biomarker protein to bind to its cognate receptor or ligand is measured.

Further embodiments relate to screening prospective agents to identify candidate agents for the treatment of AD and/or MCI in organ culture-based assays. In this format, each prospective agent is incubated with either a whole organ or a portion of an organ (such as a portion of brain tissue, such as a brain slice) derived from a non-human animal and modulation of the target AD biomarker is measured. When the drug target is an AD biomarker gene, transcriptional or translational modulation may be measured. When the drug target is the AD biomarker protein, the AD biomarker protein is also added to the assay mixture, and modulation of the half-life of the protein or of the availability of the AD biomarker protein to bind to its cognate receptor is measured.

Additional embodiments relate to screening prospective agents to identify candidate agents for the treatment of AD and/or MCI utilizing in vivo assays. In this format, each prospective agent is administered to a non-human animal and modulation of the target AD biomarker is measured. Depending on the particular drug target and the aspect of AD and/or MCI treatment that is sought to be addressed, the animal used in such assays may either be a "normal" animal (e.g., C57 mouse) or an animal which is a model of AD or MCI. A number of animal models of AD are known in the art, including the 3×Tg-AD mouse (Caccamo et al., 2003, *Neuron* 39(3):409-21), mice over expressing human amyloid beta precursor protein (APP) and presenilin genes (Westaway et al., 1997, *Nat. Med.* 3(1):67-72), and others (see Higgins et al., 2003, *Behav. Pharmacol.* 14(5-6):419-38). When the drug target is an AD biomarker gene, transcriptional or translational modulation may be measured. When the drug target is the AD biomarker protein, modulation of the half-life of the target AD biomarker or of the availability of the AD biomarker protein to bind to its cognate receptor or ligand is measured. The exact mode of measuring modulation of the target AD biomarker will, of course, depend on the identity of the AD biomarker, the format of the assay, and the preference of the practitioner. A wide variety of methods are known in the art for measuring modulation of transcription, translation, protein half-life, protein availability, and other aspects which can be measured. In view of the common knowledge of these techniques, they need not be further described here.

Kits

The invention provides kits for carrying out any of the methods described herein. Kits of the invention may comprise at least one reagent specific for an AD biomarker, and may further include instructions for carrying out a method described herein. Kits may also comprise AD biomarker reference samples, that is, useful as reference values. "AD diagnosis markers" for use in kits provided herein include, but are not limited to GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, "AD diagnosis biomarkers" for use in kits provided herein include but are not limited to basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, kits comprise any one, two, three or four of the AD diagnosis markers Leptin, RANTES, PDFG-BB and BDNF.

More commonly, kits of the invention comprise at least two different AD biomarker-specific affinity reagents, where each reagent is specific for a different AD biomarker. In some embodiments, kits comprise at least 3, at least 4, at least 5, at least 6, at least 7, at least 8, at least 9, or at least 10 reagents specific for an AD biomarker. In some embodiments, the reagent(s) specific for an AD biomarker is an affinity reagent.

Kits comprising a single reagent specific for an AD biomarker will generally have the reagent enclosed in a container (e.g., a vial, ampoule, or other suitable storage container), although kits including the reagent bound to a substrate (e.g., an inner surface of an assay reaction vessel) are also contemplated. Likewise, kits including more than one reagent may also have the reagents in containers (separately or in a mixture) or may have the reagents bound to a substrate.

In some embodiments, the AD biomarker-specific reagent(s) will be labeled with a detectable marker (such as a fluorescent dye or a detectable enzyme), or be modified to facilitate detection (e.g., biotinylated to allow for detection with a avidin- or streptavidin-based detection system). In other embodiments, the AD biomarker-specific reagent will not be directly labeled or modified.

Certain kits of the invention will also include one or more agents for detection of bound AD biomarker-specific reagent. As will be apparent to those of skill in the art, the identity of the detection agents will depend on the type of AD biomarker-specific reagent(s) included in the kit, and the intended detection system. Detection agents include antibodies specific for the AD biomarker-specific reagent (e.g., secondary antibodies), primers for amplification of an AD biomarker-specific reagent that is nucleotide based (e.g., aptamer) or of a nucleotide 'tag' attached to the AD biomarker-specific reagent, avidin- or streptavidin-conjugates for detection of biotin-modified AD biomarker-specific reagent(s), and the like. Detection systems are well known in the art, and need not be further described here. Accordingly, provided herein are kits for identifying an individual with mild cognitive impairment (MCI), comprising at least one reagent specific for RANTES; and instructions for carrying out the method. In some examples, the kits further comprise a reagent specific for leptin. In other examples, provided herein are kits for monitoring progression of Alzheimer's disease (AD) in an AD patient, comprising at least one reagent specific for leptin; and instructions for carrying out the method. Also provided herein are kits for stratifying an Alzheimer's disease (AD) patient, comprising at least one reagent specific for brain derived neurotrophic factor (BDNF); at least one reagent specific for BB homodimeric platelet derived growth factor (PDGF-BB); and instructions for carrying out the method.

A modified substrate or other system for capture of AD biomarkers may also be included in the kits of the invention, particularly when the kit is designed for use in a sandwich-format assay. The capture system may be any capture system useful in an AD biomarker assay system, such as a multi-well plate coated with an AD biomarker-specific reagent, beads coated with an AD biomarker-specific reagent, and the like. Capture systems are well known in the art and need not be further described here.

In certain embodiments, kits according to the invention include the reagents in the form of an array. The array includes at least two different reagents specific for AD biomarkers (each reagent specific for a different AD biomarker) bound to a substrate in a predetermined pattern (e.g., a grid). Accordingly, the present invention provides arrays comprising "AD diagnosis markers" including, but not limited to GCSF; IFN-g; IGFBP-1; BMP-6; BMP-4; Eotaxin-2; IGFBP-2; TARC; RANTES; ANG; PARC; Acrp30; AgRP (ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, "AD diagnosis biomarkers" include but are not limited to basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, arrays comprise any one, two, three or four of the AD diagnosis markers Leptin, RANTES, PDFG-BB and BDNF. The localization of the different AD biomarker-specific reagents (the "capture reagents") allows measurement of levels of a number of different AD biomarkers in the same reaction. Kits including the reagents in array form are commonly in a sandwich format, so such kits may also comprise detection reagents. Normally, the kit will include different detection reagents, each detection reagent specific to a different AD biomarker. The detection reagents in such embodiments are normally reagents specific for the same AD biomarkers as the reagents bound to the substrate (although the detection reagents typically bind to a different portion or site on the AD biomarker target than the substrate-bound reagents), and are generally affinity-type detection reagents. As with detection reagents for any other format assay, the detection reagents may be modified with a detectable moiety, modified to allow binding of a separate detectable moiety, or be unmodified. Array-type kits including detection reagents that are either unmodified or modified to allow binding of a separate detectable moiety may also contain additional detectable moieties (e.g., detectable moieties which bind to the detection reagent, such as labeled antibodies which bind unmodified detection reagents or streptavidin modified with a detectable moiety for detecting biotin-modified detection reagents).

The instructions relating to the use of the kit for carrying out the invention generally describe how the contents of the kit are used to carry out the methods of the invention. Instructions may include information as sample requirements (e.g., form, pre-assay processing, and size), steps necessary to measure the AD biomarker(s), and interpretation of results.

Instructions supplied in the kits of the invention are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

The following Examples are provided to illustrate the invention, but are not intended to limit the scope of the invention in any way.

EXAMPLES

Example 1

AD Diagnosis Biomarkers

We compared plasma protein expression levels for 120 proteins in 32 cases of serum collected from patients with Alzheimer's Disease (with a mean age of 74) to 19 cases of serum collected from control subjects (also with mean age of 74). Alzheimer's Disease subjects were clinically diagnosed with AD by a neurologist, and had Mini Mental State Exam (MMSE) scores ranging from 26-14.

Plasma samples were assayed using a sandwich-format ELISA on a nitrocellulose filter substrate. Plasma samples were diluted 1:10 in phosphate buffer and incubated with the capture substrate (a nitrocellulose membrane spotted with capture antibodies). The samples were incubated with the capture substrate for two hours at room temperature, then decanted from the capture substrate. The substrate was washed twice with 2 ml of washing buffer (1×PBS; 0.05% Tween-20) at room temp, then incubated with biotinylated detection antibodies for two hours at room temperature. The capture antibody solution was decanted and the substrate was washed twice for 5 min with washing buffer. The washed substrate was then incubated with horseradish peroxidase/streptavidin conjugate for 45 minutes, at which time the conjugate solution was decanted and the membranes were washed with washing buffer twice for 5 minutes. The substrate was transferred onto a piece of filter paper, incubated in enhanced chemiluminescence (ECL) Detection Buffer solution purchased from Raybiotech, Inc. Chemiluminescence was detected and quantified with a chemiluminescence imaging camera. Signal intensities were normalized to standard proteins blotted on the substrate and used to calculate relative levels of biomarkers. In other examples, signal intensities were normalized to the median and used to calculate relative levels of biomarkers.

Relative biomarker levels in plasma are compared between control and AD groups revealing 46 discriminatory biomarkers: GCSF; IFN-g; IGFBP-1; BMP-6; BMP-4; Eotaxin-2; IGFBP-2; TARC; RANTES; ANG; PARC; Acrp30; AgRP (ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. An unsupervised clustering (that is, the clustering algorithm does not know which cases are AD and which are normal) of the 46 discriminatory markers results in the clustering of the samples into 2 groups or clusters, a cluster of control samples, and a cluster of AD samples. Sensitivity was calculated as the number of correctly classed AD samples in the AD cluster/total number of AD samples, which is 29/32 or 90.6%. Specificity was calculated as total number of correctly classed control samples in the control cluster/total number of controls, which is (14/19=73.6%).

Biomarker levels were compared between control and AD groups, revealing 20 biomarkers (shown in Table 3) that are differentially regulated (each is decreased in AD as compared to control) between the two groups. Statistical analysis was performed to find the probability that the finding of differential levels was in error (the "q" value) for any one biomarker. Biomarkers with differential levels and associated q values (shown as percentage values) are shown in Table 3 (fold change indicates the fold change between levels in control vs. AD samples). Sensitivity was calculated as number of AD samples in AD cluster/total number of AD samples, which is 29/32 or 90.6%. Specificity was calculated as total correctly predicted AD/total predicted AD (29/34=85%).

TABLE 3

| Qualitative Biomarker | Fold Change (as negative value or decrease) | q-value (%) |
|---|---|---|
| Brain derived neurotrophic factor (BDNF) | 0.536 | 1.656 |
| Basic fibroblast growth factor (bFGF) | 0.673 | 1.656 |
| Epidermal growth factor (EGF) | 0.561 | 1.656 |
| Fibroblast growth factor-6 (FGF-6) | 0.664 | 1.656 |
| Interleukin-3 (IL-3) | 0.758 | 1.656 |
| Soluble interleukin-6 receptor (sIL-6 R) | 0.676 | 1.656 |
| Leptin (also known as OB) | 0.476 | 1.656 |
| Macrophage inflammatory protein 1-delta (MIP-1δ) | 0.542 | 1.656 |

TABLE 3-continued

| Qualitative Biomarker | Fold Change (as negative value or decrease) | q-value (%) |
|---|---|---|
| MSP-a | 0.764 | 1.656 |
| NAP-2 | 0.672 | 1.656 |
| Neurotrophin-3 (NT-3) | 0.698 | 1.656 |
| Platelet derived growth factor, BB dimer (PDGF-BB) | 0.536 | 1.656 |
| RANTES | 0.682 | 1.656 |
| Stem cell factor (SCF) | 0.730 | 1.656 |
| sTNF RII | 0.700 | 1.656 |
| Transforming growth factor beta-3 (TGF-β3) | 0.769 | 1.656 |
| Tissue inhibitor of metalloproteases-1 (TIMP-1) | 0.716 | 1.656 |
| Tissue inhibitor of metalloproteases-2 (TIMP-2) | 0.750 | 1.656 |
| Tumor necrosis factor beta (TNF-β) | 0.649 | 1.656 |
| TPO | 0.714 | 1.656 |

Example 2

Decision Trees from AD Diagnosis Marker Data

Upon further analysis of the data from example 1, two different decision trees were formulated for diagnosis of AD using AD diagnosis biomarkers.

The first decision tree utilizes sIL-6R, IL-8, and TIMP-1 levels. The rules which make up the decision tree are: (1) If sIL-6R $\leq 5.18$ and IL-8 is $\leq 0.957$, the indication is normal; (2) if sIL-6R $\leq 5.18$ and IL-8 >0.957, the indication is AD; (3) if sIL-6R >5.18 and TIMP-1 $\leq 7.978$, the indication is AD; and (4) if sIL-6R >5.18 and TIMP-1 is >7.978, the indication is normal, wherein the values expressed are relative concentrations.

Accuracy of this decision tree was measured using 10-fold cross-validation testing feature in CART to generate misclassification rates for learning samples and testing samples. Sensitivity was calculated from the testing scores as number of AD samples correctly predicted as AD/total number of AD samples (29/32=0.906). Specificity was calculated from the testing scores as total correctly predicted cases of AD/total number of cases predicted AD (29/33=0.878).

A second decision tree was formulating using BDNF, TIMP-1 and MIP-1δ levels. The rules which make up the decision tree are: (1) if BDNF >4.476, the indication is normal; (2) if BDNF $\leq 4.476$ and TIMP-1 $\leq 8.942$, the indication is AD; (3) if BDNF $\leq 4.476$, TIMP-1 >8.942, and MIP-1δ$\leq 1.89$, the indication is AD; and (4) if BDNF <4.476, TIMP-1 >8.942, and MIP-1δ>1.89, the indication is normal. Accuracy of this decision tree was measured using 10-fold cross-validation testing feature in CART to generate misclassification rates for learning samples and testing samples. Sensitivity was calculated from the testing scores as number of AD samples correctly predicted as AD/total number of AD samples (0.875). Specificity was calculated from the testing scores as total correctly predicted cases of AD/total number of cases predicted AD (0.82).

Example 3

Diagnosis of MCI

Levels of RANTES and Leptin were measured in 18 samples from control subjects (mean age=74) and 6 samples from patients diagnosed with mild cognitive impairment (MCI). MCI patients had been clinically diagnosed by a neurologist, and had an AULT-A7 score of less than 5 and Mini Mental State Exam (MMSE) scores ranging from 30-28. Control subjects had an AULT-A7 score greater than or equal to 5 and MMSE score ranging from 30-28.

RANTES and Leptin levels were measured using an ELISA kit from R&D systems according to the manufacturer's instructions. The raw ELISA expressions values were normalized by dividing each value by the median of all the samples. Analysis of the data showed (a) Leptin is not decreased in MCI patients as compared to control subjects (in the six MCI samples, Leptin was actually 11% higher than the control subjects), and (b) a bimodal distribution of RANTES, where MCI patients had RANTES levels of between 1.043 and 1.183 (levels from control subjects were either $\leq 1.043$ or >1.183). However, closer inspection of the data led us to believe that those control subjects with RANTES $\leq 1.043$ had been incorrectly classified as normal (and should have been diagnosed as MCI).

Reclassification of control subjects with RANTES $\leq 1.043$ as MCI patients allows the creation of a simple rule: if RANTES $\leq 1.183$ and Leptin >=0.676, the indication is MCI. Sensitivity and specificity, calculated as described in Example 2, were 83.3% and 88.88%, respectively.

Example 4

Monitoring and Stratification of AD Patients

Levels of RANTES, Leptin, PDGF-BB, and BDNF were measured in serum samples collected from 36 patients diagnosed with Alzheimer's Disease. (mean age of 74) using ELISA kits from R&D systems according to the manufacturer's instructions. The raw ELISA expressions values were normalized by dividing each value by the median of all the samples. The samples were grouped into three classes on the basis of MMSE score: Class 1 (mild AD), MMSE 27-22; Class 2 (moderate AD), MMSE 21-16; and Class 3 (severe AD), MMSE 15-12.

Upon analysis of the ELISA data, we formulated a decision tree using BDNF and PDGF-BB. The rules which make up the decision tree are: (1) if BDNF $\leq 0.626$, the indication is mild AD; (2) if BDNF >0.626 and PDGF-BB $\leq 0.919$, the indication is moderate AD; and (3) if BDNF >0.626 and PDGF-BB >0.919, the indication is severe AD. The values expressed are relative concentrations that have been normalized to the median. Average normalized levels for Leptin were: Class I=0.886; class II=0.757; class III=0.589. Average normalized levels for BDNF were: Class I=0.595; class II=0.956; class III=1.23. When applied to a set of "test" data, the decision tree produced 58%, 47%, and 57% percent correct stratification of the test samples into mild, moderate, and severe categories.

Example 5

Four Discriminatory Markers

The absolute concentrations in plasma of only 4 discriminatory markers, BDNF, PDGF-BB, LEPTIN, and RANTES measured by ELISA was used to classify samples. ELISA kits were purchased from R&D Systems, and measurements were obtained according to manufacturer recommendations. For example for RANTES, the following protocol was followed.

1. Add 50 µL standards, specimens or controls to appropriate wells.
2. Add 50 µL anti-RANTES Biotin Conjugate to each well.
3. Incubate wells at 37° C. for 1 hour.
4. Aspirate and wash wells 4× with Working Wash Buffer.
5. Add 100 µL Streptavidin-HRP Working Conjugate to each well.
6. Incubate for 30 minutes at room temperature.
7. Aspirate and wash wells 4× with Working Wash Buffer.
8. Add 100 µL of Stabilized Chromogen to each well.
9. Incubate at room temperature for 30 minutes in the dark.
10. Add 100 µL of Stop Solution to each well.
11. Read absorbance at 450 nm.

Following the above protocol, an unsupervised clustering of BDNF, PDGF-BB, LEPTIN, and RANTES was performed using the publicly available web based clustering software wCLUTO at cluto.ccgb.umn.edu/cgi-bin/wCluto/wCluto.cgi. Here the clustering of the 4 proteins resulted in the clustering of the samples into 2 groups or clusters, a cluster of control samples and a cluster of AD samples. Sensitivity was calculated as the number of correctly classed AD samples in the AD cluster/total number of AD samples, which is 21/24 or 87.5%. Specificity was calculated as total number of correctly classed control samples in the control cluster/total number of controls, which is 20/24=83.3%.

Additionally, absolute biomarker levels in plasma (as measured by ELISA) for BDNF, PDGF-BB, and LEPTIN, were correlated with MMSE scores (range 12-30). AD could be identified in MMSE scores in a range of 12-28 and control samples were identified in MMSE scores in the range of 25-30. Table 4 shows the correlations and their statistical significance (p-value). The upper and lower correlations show whether the upper end of the range of MMSE scores and biomarker concentrations or the lower end of the range of MMSE scores and biomarker concentrations are more correlated. Therefore, the correlations show that higher levels of BDNF and Leptin are significantly correlated with better MMSE scores, and that increase in the concentration of BDNF and Leptin from a reference point or an earlier collection is an indication of improvement in cognition as measured by MMSE. Simultaneously, or by itself, the lower the levels of PDGF-BB in men is significantly correlated with better MMSE scores, and a decrease in the concentration of PDGF-BB in male sample compared to an earlier collection in that male, is an indication of improvement in cognition as measured by MMSE.

The results show (Table 4) the correlation between the plasma concentration of 3 discriminatory proteins for AD to the MMSE score of the subjects and the correlation between concentrations of proteins that are discriminatory for AD. There was no correlation between MMSE score and Age among AD subjects and there was no correlation between Age and the concentration of BDNF, PDGF-BB, or LEPTIN in plasma among AD subjects. The p-values show that the correlations are statistically significant. The count shows the number of cases. BDNF has a statistically significant positive correlation with MMSE scores. PDGF-BB has a statistically significant negative correlation with MMSE scores in men. LEPTIN has a statistically significant positive correlation with MMSE scores. This experiment demonstrates that plasma concentrations for PDGF-BB, LEPTIN, and BDNF can be used to monitor the progression of cognitive decline.

TABLE 4

|  | Correlation | Count | Z-value | P-value | 95% Lower | 95% Upper |
|---|---|---|---|---|---|---|
| BDNF to MMSE | 0.184 | 165 | 2.373 | 0.0176 | 0.032 | 0.328 |
| BDNF to MMSE (Females) | 0.229 | 91 | 2.18 | 0.0289 | 0.024 | 0.415 |
| PDGF-BB to MMSE (Males) | −0.207 | 74 | −1.769 | 0.0768 | −0.416 | 0.023 |
| LEPTIN to MMSE | 0.193 | 164 | 2.478 | 0.0132 | 0.041 | 0.336 |
| BDNF to PDGF-BB | 0.700 | 181 | 11.575 | 0.0001 | 0.617 | 0.768 |
| PDGF-BB to RANTES | 0.563 | 181 | 8.5 | 0.0001 | 0.454 | 0.655 |
| BDNF to RANTES | 0.714 | 181 | 11.9 | 0.0001 | 0.634 | 0.779 |

Controls and AD cases were age matched, and had a mean age of 74. The mean MMSE score for AD cases (n=24) was 20, while the mean MMSE score for Control cases (n=24) was 30. Classification of the samples was performed with unsupervised clustering of protein concentration. The total accuracy of classification was 85.4%. This results demonstrated that plasma protein concentrations for BDNF, PDGF-BB, LEPTIN, and RANTES, as measured by ELISA can be used to accurately discriminate between AD and controls.

Example 6

Validation of Mean Protein Concentrations in AD and Controls by ELISA

Figure 1B:
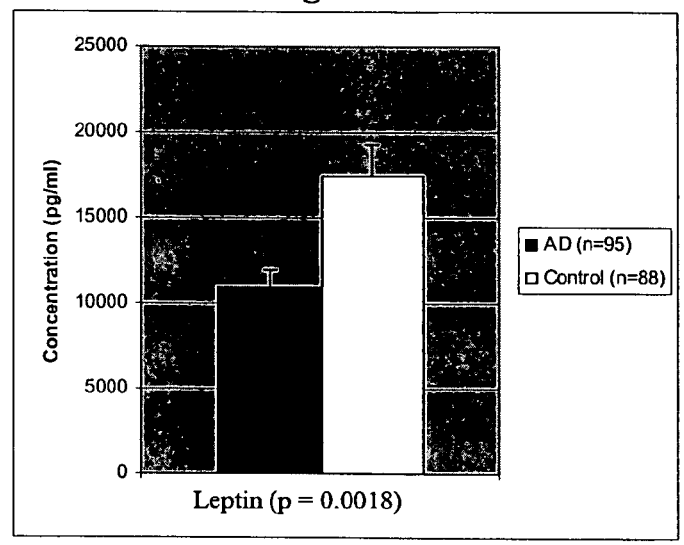
Figure 1C:
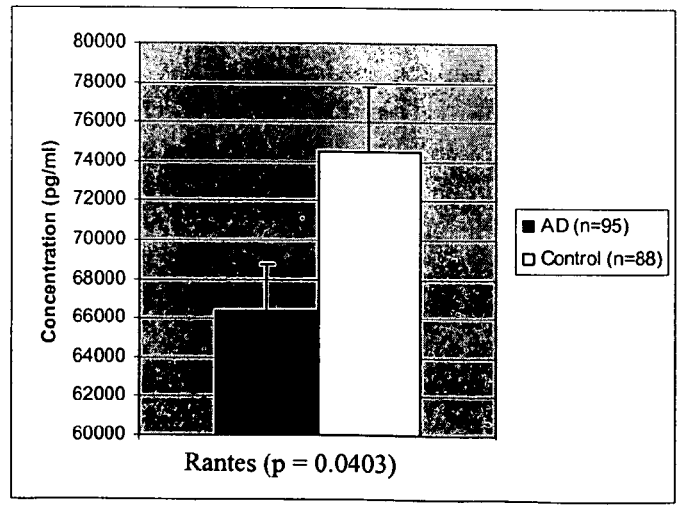

Protein concentrations for proteins, LEPTIN, BDNF and RANTES, in plasma samples of AD (n=95) to age matched Controls (n=88) are shown in FIGS. 1A-1C. One of the four proteins we measured was Brain Derived Neurotrophic Factor (BDNF). The mean concentration of BDNF in AD plasma was 8.1 ng/ml (SE+/−0.4) compared to the mean of control plasma 10.8ng/ml (SE+/−0.68) and the difference was found to be extremely statistically significant (p-value=0.0006). We also found that the concentrations of BDNF were lower in other forms of dementia (5.74ng/ml, n=20) than AD. The mean concentration of a second protein Leptin in AD plasma was found to be 10.9 ng/ml (SE+/−1.06) compared to the mean of control plasma 17.4 ng/ml (SE+/−1.8) and the difference was found to be statistically very significant (p-value=0.0018). The mean concentration of a third protein Rantes in AD plasma was found to be 66.3 ng/ml (SE+/−2.4) compared to control samples 74.5 ng/ml (SE+/−3.2) and the difference was found to be statistically significant (p-value=0.0403). No difference in the means of concentrations for RANTES, PDGF-BB, and BDNF were observed among AD subjects with MMSE scores=/>20 (n=54) and those <20 (n=41).

Example 7

Absolute Biomarker Concentrations in Plasma

Figure 2:
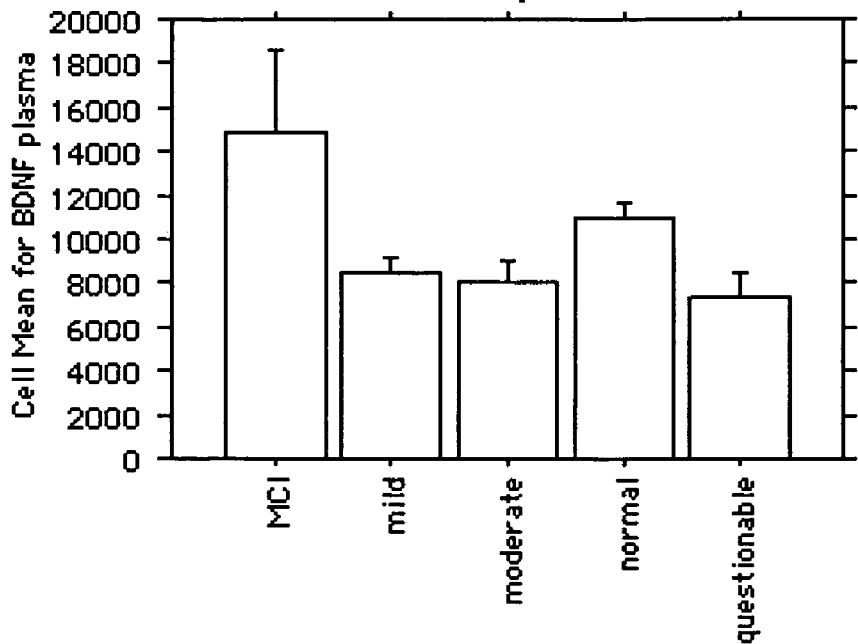
FIG. 2 shows a Cell Bar Chart for concentration of BDNF in plasma. (Cell Bar Chart Grouping Variable(s): stage Error Bars: ±1 Standard error(s) Inclusion criteria: Sparks from Center All)

Additionally, absolute biomarker concentrations in plasma were measured for BDNF, and mean concentrations for Controls was compared to MCI (Mild Cognitive Impairment), MMSE 25-28, MMSE 20-25, and MMSE 10-20. For the purposes of this experiment, the index used in the following example is: questionable AD is=MMSE score in the range of 25-28; mild AD=MMSE score in the range of 20-25; and moderate AD=MMSE score in the range of 10-20 and severe AD =MMSE score in the range of 10-20. For the purpose of Example 7, all individuals assessed as having Questionable AD were diagnosed by a physician as having AD. The FIG. 2 shows that mean concentrations of BDNF in plasma for MMSE 25-28; MMSE 20-25; MMSE 10-20 are significantly lower than the mean concentration in Controls (Normal, mean age 74) and the mean concentration of BDNF in MCI is significantly higher than in Controls and all cases of AD. FIG. 2.

Unpaired t-test for BDNF plasma
Grouping Variable: stage
Hypothesized Difference = 0
Inclusion criteria: Sparks from Center All

|  | Mean Diff. | DF | t-Value | P-Value |
|---|---|---|---|---|
| MCI, mild | 6349.252 | 47 | 3.050 | .0038 |
| MCI, moderate | 6828.574 | 31 | 2.651 | .0125 |
| MCI, normal | 3961.358 | 86 | 1.442 | .1529 |
| MCI, questionable | 7547.218 | 17 | 2.550 | .0207 |
| mild, moderate | 479.322 | 68 | .460 | .6467 |
| mild, normal | −2387.894 | 123 | −2.270 | .0250 |
| mild, questionable | 1197.966 | 54 | .969 | .3369 |
| moderate, normal | −2867.216 | 107 | −2.175 | .0319 |
| moderate, questionable | 718.644 | 38 | .475 | .6372 |
| normal, questionable | 3585.860 | 93 | 1.993 | .0492 |

Group Info for BDNF plasma
Grouping Variable: stage
Inclusion criteria: Sparks from Center All

|  | Count | Mean | Variance | Std. Dev. | Std. Err |
|---|---|---|---|---|---|
| MCI | 6 | 14879.833 | 85932530.967 | 9269.980 | 3784.454 |
| mild | 43 | 8530.581 | 15299257.963 | 3911.427 | 596.487 |
| moderate | 27 | 8051.259 | 22317487.815 | 4724.139 | 909.161 |
| normal | 82 | 10918.476 | 39478328.993 | 6283.178 | 693.861 |
| questionable | 13 | 7332.615 | 15122872.923 | 3888.814 | 1078.563 |

Figure 3:
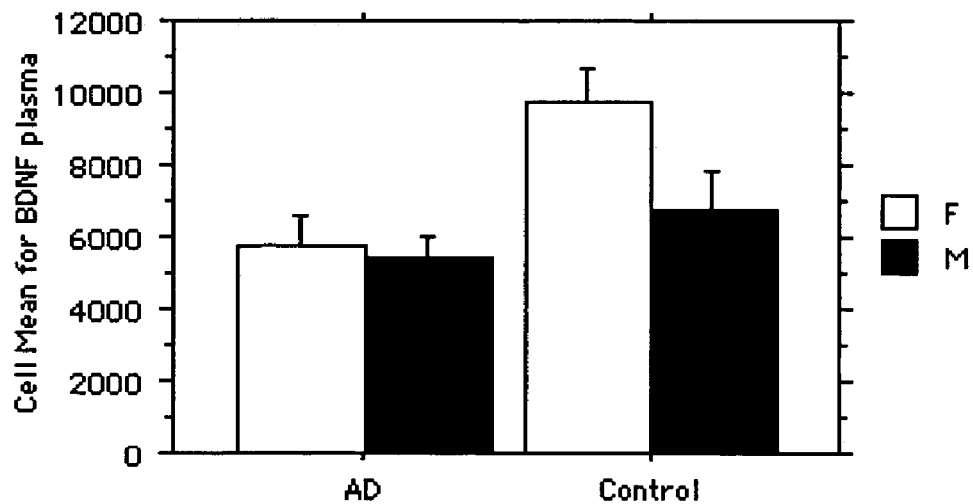
FIG. 3 shows BDNF in control vs AD for male and female. (Cell Bar Chart Grouping Variable(s): Disease Split By: sex Error Bars: ±1 Standard Error(s) Row exclusion: Center All)

Additionally, absolute concentrations of BDNF, in plasma samples collected from four separate Alzheimer's Centers was compared for gender differences in mean concentrations between AD (Females) and Control (Females) and AD (Males) and Control (Males). FIG. 3 shows that there is 40% difference in the concentration of BDNF in AD Females compared to Control Females and the difference is highly statistically significant (p-value=0.004). The difference in the mean concentration of BDNF for all AD cases compared to all Control case was found to be extremely statistically significant (p-value=0.0006).

| | Unpaired t-test for BDNF plasma Grouping Variable: Disease Split By: sex Hypothesized Difference = 0 Row exclusion: Center All | | | |
|---|---|---|---|---|
| | Mean Diff. | DF | t-Value | P-Value |
| AD, Control: Total | −2974.140 | 187 | −3.482 | .0006 |
| AD, Control: F | −3939.353 | 87 | −2.924 | .0044 |
| AD, Control: M | −1348.601 | 92 | −1.165 | .2469 |

Results for totals may not agree with results for individual cells because of missing values for split variables.

| | Group Info for BDNF plasma Grouping Variable: Disease Split By: sex Row exclusion: Center All | | | | |
|---|---|---|---|---|---|
| | Count | Mean | Variance | Std. Dev. | Std. Err |
| AD: Total | 106 | 5596.113 | 24323422.844 | 4931.878 | 479.026 |
| AD: F | 38 | 5775.921 | 25121499.318 | 5012.135 | 813.076 |
| AD: M | 62 | 5396.774 | 24336564.079 | 4933.210 | 626.518 |
| Control: Total | 83 | 8570.253 | 46322420.606 | 6806.058 | 747.062 |
| Control: F | 51 | 9715.275 | 50173107.603 | 7083.298 | 991.860 |
| Control: M | 32 | 6745.375 | 36011373.274 | 6000.948 | 1060.828 |

Results for totals may not agree with results for individual cells because of missing values for split variables.

Figure 4:
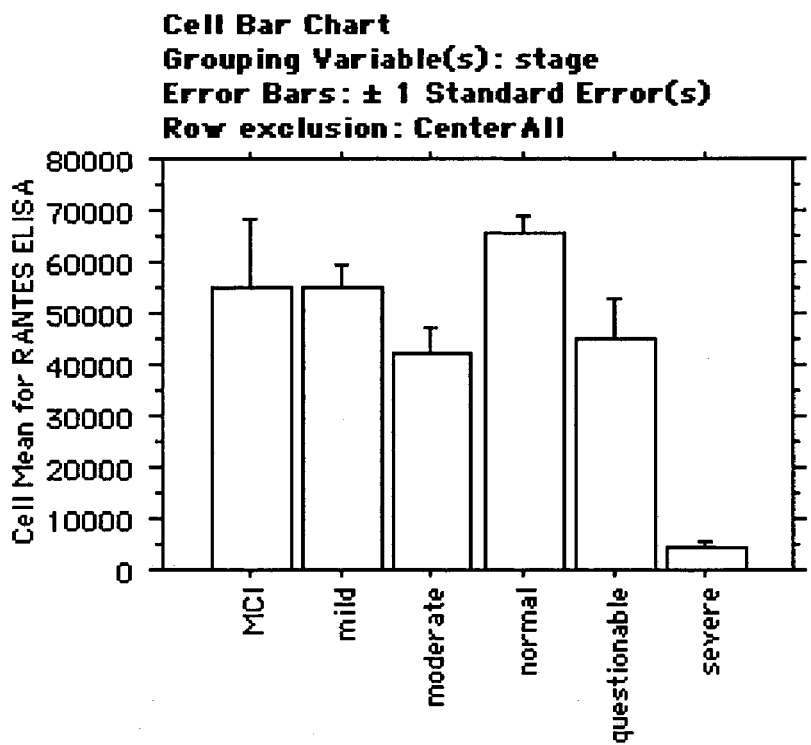
FIG. 4 shows RANTES concentration in plasma. (Cell Bar Chart Grouping Variable(s): stage Error Bars: ±1 Standard Error(s) Row exclusion: Center All)

Additionally, absolute biomarker concentrations in plasma were measured for RANTES in plasma samples collected from four different Alzheimer's Centers, and mean concentrations for Controls were compared to MCI (Mild Cognitive Impairment), MMSE 25-28; (MMSE 20-25; MMSE 10-20; and MMSE 10-20. The index is described above. The mean differences between Mild AD compared to Moderate AD, Mild AD compared to Normal, Mild AD compared to Severe AD, Moderate AD compared to Normal, Questionable AD compared to Normal, Normal to Severe AD were all found to be statistically significant. FIG. 4.

| | Unpaired t-test for RANTES ELISA Grouping Variable: stage Hypothesized Difference = 0 Row exclusion: Center All | | | |
|---|---|---|---|---|
| | Mean Diff. | DF | t-Value | P-Value |
| MCI, mild | 84.789 | 64 | .007 | .9945 |
| MCI, moderate | 12454.688 | 51 | 1.042 | .3022 |
| MCI, normal | −10422.892 | 106 | −.866 | .3884 |
| MCI, questionable | 9682.438 | 29 | .682 | .5007 |
| MCI, severe | 50349.200 | 10 | 1.647 | .1305 |
| mild, moderate | 12369.899 | 97 | 1.814 | .0728 |
| mild, normal | −10507.681 | 152 | −1.775 | .0780 |
| mild, questionable | 9597.649 | 75 | 1.081 | .2830 |
| mild, severe | 50264.411 | 56 | 2.031 | .0470 |
| moderate, normal | −22877.580 | 139 | −3.606 | .0004 |
| moderate, questionable | −2772.250 | 62 | −.315 | .7535 |
| moderate, severe | 37894.512 | 43 | 1.647 | .1069 |
| normal, questionable | 20105.330 | 117 | 2.353 | .0203 |
| normal, severe | 60772.092 | 98 | 2.395 | .0185 |
| questionable, severe | 40666.762 | 21 | 1.624 | .1192 |

| | Group Info for RANTES ELISA Grouping Variable: stage Row exclusion: Center All | | | | |
|---|---|---|---|---|---|
| | Count | Mean | Variance | Std. Dev. | Std. Err |
| MCI | 10 | 54919.200 | 1729660285.733 | 41589.185 | 13151.655 |
| mild | 56 | 54834.411 | 1203622609.701 | 34693.265 | 4636.082 |
| moderate | 43 | 42464.512 | 1036226732.256 | 32190.476 | 4909.002 |
| normal | 98 | 65342.092 | 1275358885.672 | 35712.167 | 3607.474 |
| questionable | 21 | 45236.762 | 1201710117.890 | 34665.691 | 7564.674 |
| severe | 2 | 4570.000 | 2976800.000 | 1725.341 | 1220.000 |

Figure 5:
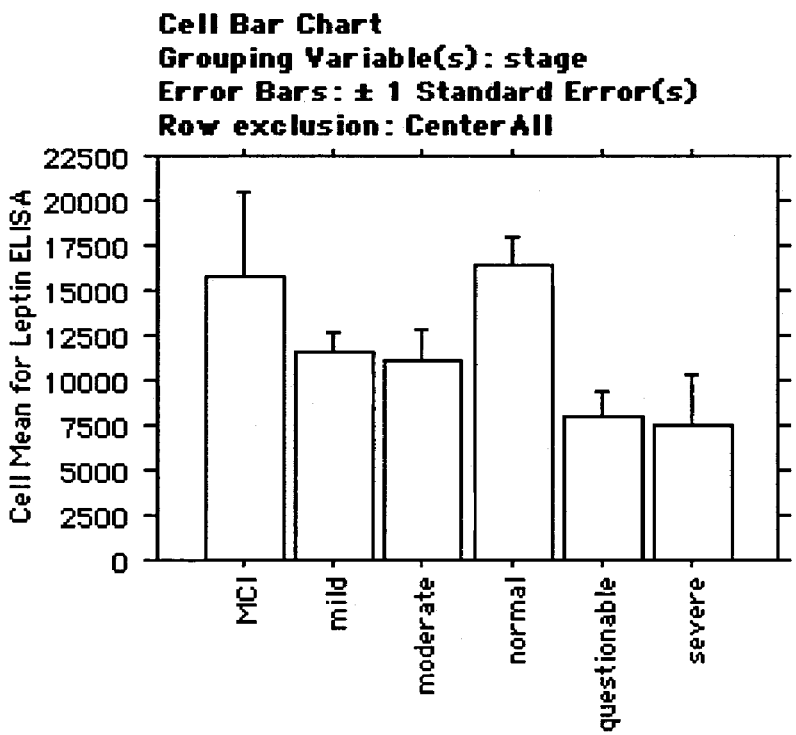
FIG. 5 shows concentration of Leptin in plasma. (Cell Bar Chart Grouping Variable(s): stage Error Bars: ±1 Standard Error(s) Row exclusion: Center All)

Additionally, absolute biomarker concentrations in plasma were measured for Leptin in plasma samples collected from four different Alzheimer's Centers, and mean concentrations for Controls were compared to MCI (Mild Cognitive Impairment); MMSE 25-28; MMSE 20-25; MMSE 10-20; and MMSE 10-20. The mean differences between Questionable AD compared to MCI, Mild AD compared to Normal, Mild AD compared to Questionable AD, Questionable AD compared to Normal, and Moderate AD compared to Normal were all found to be statistically significant. FIG. 5.

| | Unpaired t-test for Leptin ELISA Grouping Variable: stage Hypothesized Difference = 0 Row exclusion: Center All | | | |
|---|---|---|---|---|
| | Mean Diff. | DF | t-Value | P-Value |
| MCI, mild | 4164.889 | 64 | 1.338 | .1856 |
| MCI, moderate | 4707.044 | 51 | 1.061 | .2939 |
| MCI, normal | −650.092 | 105 | −.123 | .9022 |
| MCI, questionable | 7793.348 | 29 | 2.000 | .0550 |
| MCI, severe | 8187.800 | 10 | .739 | .4767 |
| mild, moderate | 542.155 | 97 | .272 | .7860 |
| mild, normal | −4814.981 | 151 | −2.117 | .0359 |
| mild, questionable | 3628.458 | 75 | 1.897 | .0617 |
| mild, severe | 4022.911 | 56 | .734 | .4661 |
| moderate, normal | −5357.136 | 138 | −1.963 | .0516 |
| moderate, questionable | 3086.303 | 62 | 1.085 | .2822 |
| moderate, severe | 3480.756 | 43 | .403 | .6892 |
| normal, questionable | 8443.439 | 116 | 2.368 | .0195 |
| normal, severe | 8837.892 | 97 | .778 | .4383 |
| questionable, severe | 394.452 | 21 | .078 | .9383 |

| | Group Info for Leptin ELISA Grouping Variable: stage Row exclusion: Center All | | | | |
|---|---|---|---|---|---|
| | Count | Mean | Variance | Std. Dev. | Std. Err |
| MCI | 10 | 15727.300 | 225300738.678 | 15010.021 | 4746.585 |
| mild | 56 | 11562.411 | 58790550.756 | 7667.500 | 1024.613 |
| moderate | 43 | 11020.256 | 145797834.909 | 12074.677 | 1841.371 |
| normal | 97 | 16377.392 | 255125297.032 | 15972.642 | 1621.776 |
| questionable | 21 | 7933.952 | 47833192.348 | 6916.154 | 1509.229 |
| severe | 2 | 7539.500 | 16125520.500 | 4015.659 | 2839.500 |

Figure 6:
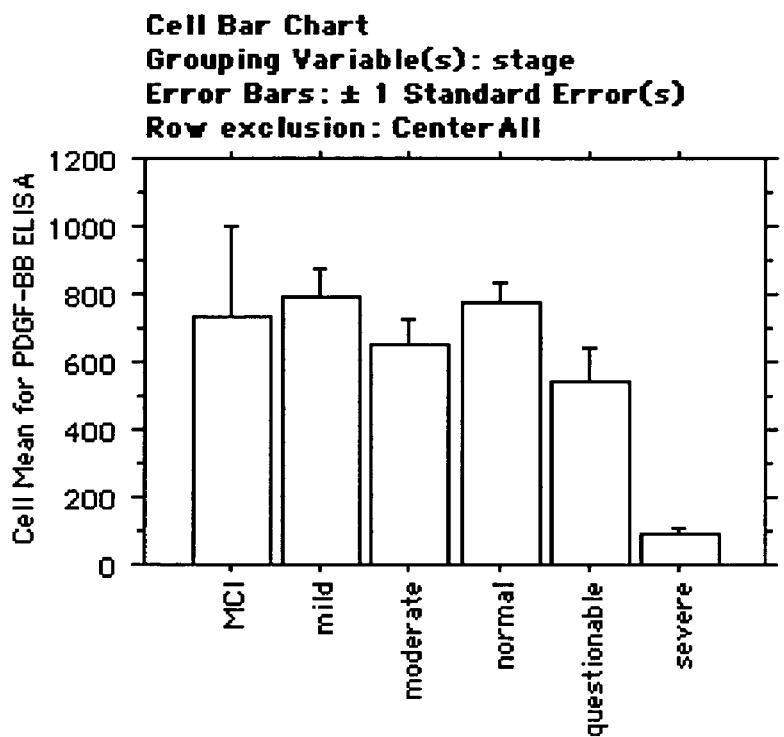
FIG. 6 shows PDGF-BB concentration in plasma. (Cell Bar Chart Grouping Variable(s): stage Error Bars: ±1 Standard Error(s) Row exclusion: Center All)

Additionally, absolute biomarker concentrations in plasma were measured for PDGF-BB in plasma samples collected from four different Alzheimer's Centers, and mean concentrations for Controls were compared to MCI (Mild Cognitive Impairment); MMSE 25-28; MMSE 20-25; MMSE 10-20; and MMSE 10-20. The mean differences between Questionable AD compared to Mild AD, Mild AD compared to Severe AD, Moderate AD compared to Severe AD, Normal compared to Questionable AD, and Normal to Severe AD were all found to be statistically significant. FIG. 6.

Unpaired t-test for PDGF-BB ELISA
Grouping Variable: stage
Hypothesized Difference = 0
Row exclusion: Center All

|  | Mean Diff. | DF | t-Value | P-Value |
|---|---|---|---|---|
| MCI, mild | −62.275 | 58 | −.286 | .7756 |
| MCI, moderate | 81.595 | 44 | .411 | .6831 |
| MCI, normal | −42.865 | 103 | −.210 | .8343 |
| MCI, questionable | 191.571 | 28 | .810 | .4246 |
| MCI, severe | 637.000 | 9 | 1.072 | .3117 |
| mild, moderate | 143.869 | 86 | 1.285 | .2023 |
| mild, normal | 19.410 | 145 | .199 | .8426 |
| mild, questionable | 253.846 | 70 | 1.812 | .0742 |
| mild, severe | 699.275 | 51 | 1.745 | .0871 |
| moderate, normal | −124.459 | 131 | −1.201 | .2320 |
| moderate, questionable | 109.977 | 56 | .869 | .3885 |
| moderate, severe | 555.405 | 37 | 1.716 | .0945 |
| normal, questionable | 234.436 | 115 | 1.767 | .0799 |
| normal, severe | 679.865 | 96 | 1.696 | .0931 |
| questionable, severe | 445.429 | 21 | 1.278 | .2153 |

Group Info for PDGF-BB ELISA
Grouping Variable: stage
Row exclusion: Center All

|  | Count | Mean | Variance | Std. Dev. | Std. Err |
|---|---|---|---|---|---|
| MCI | 9 | 731.000 | 650139.000 | 806.312 | 268.771 |
| mild | 51 | 793.275 | 315391.883 | 561.598 | 78.639 |
| moderate | 37 | 649.405 | 204231.470 | 451.920 | 74.295 |
| normal | 96 | 773.865 | 318171.171 | 564.067 | 57.570 |
| questionable | 21 | 539.429 | 233024.657 | 482.726 | 105.340 |
| severe | 2 | 94.000 | 648.000 | 25.456 | 18.000 |

Figure 7:
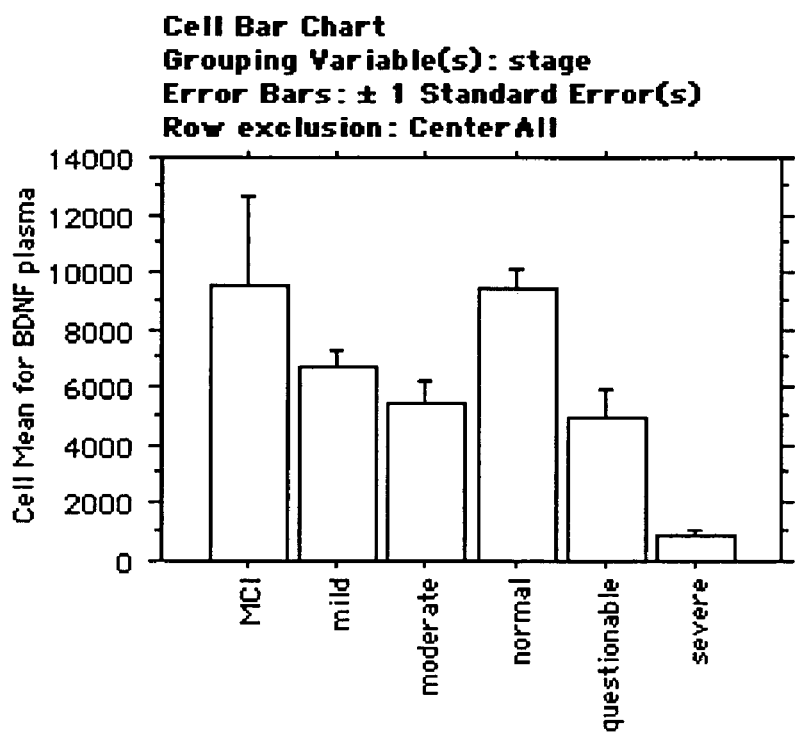
FIG. 7 shows BDNF concentration in plasma. (Cell Bar Chart Grouping Variable(s): stage Error Bars: ±1 Standard Error(s) Row exclusion: Center All)

Additionally, absolute biomarker concentrations in plasma were measured for BDNF in plasma samples collected from four different Alzheimer's centers, and means concentrations for Controls were compared to MCI (Mild Cognitive Impairment), Questionable AD (MMSE 25-28), Mild differences between MCI compared to Moderate AD, MCI compared to Questionable AS, Mild AD to Normal, Mild AD to sever AD, Moderate to Normal, Normal to Questionable AD, and Normal to Severe were all found to be statistically significant. FIG. 7.

Unpaired t-test for BDNF plasma
Grouping Variable: stage
Hypothesized Difference = 0
Row exclusion: Center All

|  | Mean Diff. | DF | t-Value | P-Value |
|---|---|---|---|---|
| MCI, mild | 2819.186 | 64 | 1.433 | .1568 |
| MCI, moderate | 4071.016 | 51 | 1.877 | .0663 |
| MCI, normal | 124.278 | 106 | .053 | .9578 |
| MCI, questionable | 4535.757 | 29 | 1.806 | .0813 |
| MCI, severe | 8660.400 | 10 | 1.202 | .2570 |
| mild, moderate | 1251.831 | 97 | 1.262 | .2098 |
| mild, normal | −2694.908 | 152 | −2.638 | .0092 |
| mild, questionable | 1716.571 | 75 | 1.447 | .1520 |
| mild, severe | 5841.214 | 56 | 1.726 | .0898 |
| moderate, normal | −3946.739 | 139 | −3.431 | .0008 |
| moderate, questionable | 464.741 | 62 | .360 | .7199 |
| moderate, severe | 4589.384 | 43 | 1.265 | .2128 |
| normal, questionable | 4411.480 | 117 | 2.868 | .0049 |
| normal, severe | 8536.122 | 98 | 1.781 | .0781 |
| questionable, severe | 4124.643 | 21 | 1.321 | .2006 |

Group Info for BDNF plasma
Grouping Variable: stage
Row exclusion: Center All

|  | Count | Mean | Variance | Std. Dev. | Std. Err |
|---|---|---|---|---|---|
| MCI | 10 | 9511.900 | 96113654.322 | 9803.757 | 3100.220 |
| mild | 56 | 6692.714 | 22509096.208 | 4744.375 | 633.994 |
| moderate | 43 | 5440.884 | 25765123.534 | 5075.936 | 774.073 |
| normal | 98 | 9387.622 | 45504479.969 | 6745.701 | 681.419 |
| questionable | 21 | 4976.143 | 18681976.129 | 4322.265 | 943.196 |
| severe | 2 | 851.500 | 63724.500 | 252.437 | 178.500 |

It has been found that for Questionable AD (MMSE score in the range of 25-28) the levels of Leptin and PDGF-BB increase significantly whereas BDNF and RANTES do not change significantly. It has been found that from Mild AD (MMSE score in the range of 20-25) to Moderate AD (MMSE score in the range of 10-20) the level of LEPTIN does not decline whereas the levels for RANTES, BDNF and PDGF-BB declines.

Example 8

In an attempt to identify proteins that are altered in the peripheral immune system in AD, expression levels of 120 cytokines, chemokines, and growth factors in plasma from 32 AD patients and 19 nondemented age-matched controls were measured using spotted antibody microarrays on filters. Statistical analysis identified 20 proteins as significantly different between AD and controls. Six of them including brain derived neurotrophic factor (BDNF) and NT-3, and PDGF-BB, EGF, FGF-6, bFGF, TGF-b3 have known neurotrophic activity and were significantly reduced in AD plasma. BDNF levels correlated with better cognitive function in the mini mental state exam (MMSE). BDNF measurements in plasma from two hundred AD cases and controls using commercial sandwich ELISA showed a highly significant 25% reduction in AD cases. Consistent with the array data, reduced plasma BDNF levels were associated with impaired memory function. BDNF is critical for neuronal maintenance, survival, and function. Without being bound by theory decreased blood levels of neurotrophins and BDNF may be linked with neurodegeneration and cognitive dysfunction in AD.

Example 9

Additional Biomarkers

Additionally, qualitative biomarker levels for GDNF, SDF-1, IGFBP3, FGF-6, TGF-b3, BMP-4, NT-3, EGF, BDNF, IGFBP-2 were correlated with MMSE scores (range 12-30) for AD (MMSE range 12-28) and control samples (MMSE range 25-30). Table 5 shows the correlations and their statistical significance (p-value). The upper and lower correlations show whether the upper end of the range of MMSE Scores and biomarker concentrations or the lower end of the range of MMSE scores and biomarker concentrations are more correlated. A negative correlation means that MMSE scores increase with decreasing levels of biomarker and vice versa. A positive correlation mean that MMSE scores increase with increasing levels of biomarker.

TABLE 5

| | Correlation | Count | Z-value | P-value | 95% Lower | 95% Upper |
| --- | --- | --- | --- | --- | --- | --- |
| GDNF to MMSE | −0.258 | 42 | −1.646 | 0.0997 | −0.521 | 0.05 |
| SDF-1 to MMSE | −0.363 | 42 | −2.375 | 0.0175 | −0.601 | −0.066 |
| IGFBP-3 to MMSE | 0.293 | 42 | 1.886 | 0.0593 | −0.012 | 0.548 |
| FGF-6 to MMSE | 0.471 | 42 | 3.192 | 0.0014 | 0.195 | 0.687 |
| TGF-b3 to MMSE | 0.317 | 42 | 2.049 | 0.0405 | 0.014 | 0.566 |
| BMP-4 to MMSE | 0.294 | 42 | 1.845 | 0.0583 | −0.011 | 0.545 |
| NT-3 to MMSE | 0.327 | 42 | 2.118 | 0.0342 | 0.025 | 0.574 |
| EGF to MMSE | 0.409 | 42 | 2.711 | 0.0067 | 0.12 | 0.634 |
| BDNF to MMSE | 0.464 | 42 | 3.139 | 0.0017 | 0.187 | 0.673 |
| IGFBP-2 to MMSE (Females) | 0.498 | 24 | 2.5 | 0.0123 | 0.118 | 0.75 |

Example 10

This example shows Table 6, a Summary of Quantitative Markers for Identification and Stratification of AD.

TABLE 6

| References | Samples | Plasma BioMarker | % Difference in Samples | p-value |
| --- | --- | --- | --- | --- |
| Normal | Questionable AD | BDNF | −46% | 0.0049 |
| Normal | Questionable AD | Leptin | −52% | 0.0195 |
| Normal | Questionable AD | RANTES | −31% | 0.0203 |
| Normal | Questionable AD | PDGF-BB | −30% | 0.0799 |
| Normal | Mild AD | BDNF | −29% | 0.0092 |
| Normal | Mild AD | Leptin | −29% | 0.0359 |
| Normal | Mild AD | RANTES | −16% | 0.0780 |
| Normal | Moderate AD | BDNF | −42% | 0.0008 |
| Normal | Moderate AD | Leptin | −33% | 0.0359 |
| Normal | Moderate AD | RANTES | −35% | 0.0004 |
| Normal | Severe AD | BDNF | −90% | 0.0781 |
| Normal | Severe AD | RANTES | −93% | 0.0185 |
| Normal | Severe AD | PDGF-BB | −89% | 0.0931 |
| Questionable AD | Mild AD | Leptin | 45% | 0.0617 |
| Questionable AD | Mild AD | PDGF-BB | 46% | 0.0742 |
| Mild AD | Moderate AD | RANTES | −23% | 0.0780 |
| Mild AD | Severe AD | BDNF | −87% | 0.0898 |
| Mild AD | Severe AD | RANTES | −92% | 0.0470 |
| Mild AD | Severe AD | PDGF-BB | −88% | 0.0871 |
| Questionable AD | MCI | BDNF | 91% | 0.0813 |
| Questionable AD | MCI | Leptin | 98% | 0.0550 |
| MCI | Mild AD | BDNF | −42% | 0.0038 |

Accordingly, the present invention provides methods of aiding diagnosis of Alzheimer's disease ("AD"), comprising comparing a measured level of at least 4 AD diagnosis biomarkers, wherein said biomarkers comprise BDNF, PDGF-BB, Leptin and RANTES, in a biological fluid sample from an individual to a reference level for each AD diagnosis biomarker. Accordingly, methods are provided in which BDNF decreased at least about 10%, about 15%, about 20%, about 25% or about 30% as compared to a reference level of BDNF, indicates cognitive impairment, such as for example, an indication of AD. Accordingly, methods are provided in which Leptin decreased at least about 10%, about 15%, about 20%, about 25% or about 30% as compared to a reference level of Leptin, indicates cognitive impairment, such as for example, an indication of AD. Accordingly, methods are provided in which RANTES decreased at least about 5%, about 10%, or about 15% as compared to a reference level of RANTES, indicates cognitive impairment, such as for example, an indication of AD. Accordingly, methods are provided in which PDGF-BB decreased at least about 80%, about 85% or about 90% as compared to a reference level of PDGF-BB, indicates cognitive impairment, such as for example, an indication of severe AD.

TABLE 7

| Protein | Alternate names | Class | Protein ID |
|---|---|---|---|
| alpha-1 acid glycoprotein | | acute phase | |
| alpha-1 antitrypsin | | acute phase | |
| Ceruloplasmin | | acute phase | |
| Haptoglobin | | acute phase | |
| Hemopexin | | acute phase | |
| Hemoxygenase | | acute phase | |
| plasminogen activator inhibitor-1 | PAI-1 | acute phase | |
| serum amyloid A | SAA | acute phase | |
| serum amyloid P | SAP | acute phase | |
| 4-11313 ligand | 4-1BBL/CD137L | apoptosis | P41273 |
| BAFF | TALL-1 | apoptosis | Q9Y275 |
| soluble TRAIL receptor 3 | TRAIL sR3/TNFR S10C | apoptosis | O14755 |
| soluble TRAIL receptor 4 | TRAIL sR4/TNFR S10D | apoptosis | Q9UBN6 |
| TNF-related death ligand 1a | TRDL-1a/APRIL | apoptosis | AF046888 |
| TNFSF-14 | LIGHT | apoptosis | O43557 |
| TRAIL | Apo2L | apoptosis | P50591 |
| BCA-1 | BLC | chemokine | O43927 |
| CCL-28 | CCK-1 | chemokine | |
| cutaneous T cell attracting chemokine | CTACK, CCL27 | chemokine | Qgz1X0 |
| ENA-78 | | chemokine | P42830 |
| Eotaxin-1 | | chemokine | P51671 |
| Eotaxin-2 | MPIF-2 | chemokine | O00175 |
| Eotaxin-3 | CCL26 | chemokine | Q9Y258 |
| Fractalkine | neurotactin | chemokine | P78423 |
| Granulocyte chemotactic protein 2 | GCP-2 | chemokine | P80162 |
| GRO alpha | MGSA | chemokine | P09341 |
| GRO beta | MIP-2alpha | chemokine | P19875 |
| GRO gamma | MIP-2beta | chemokine | P19876 |
| haemoinfiltrate CC chemokine 1 | HCC-1 | chemokine | Q16627 |
| haemoinfiltrate CC chemokine 4 | HCC-4/CCL16 | chemokine | O15476 |
| I-309 | TCA-3/CCL-1 | chemokine | P22362 |
| IFNgamma inducible protein-10 | IP-10 | chemokine | P02778 |
| IFN-inducible T cell alpha chemokine | I-TAC/CXCL11 | chemokine | AF030514 |
| interleukin-8 | IL-8/NAP-1 | chemokine | P10145 |
| leucocyte cell-derived chemotaxin-2 | LECT2 | chemokine | |
| Lungkine | CXCL-15/WECHE | chemokine | |
| Lymphotactin | Lptn/ATAC | chemokine | P47992 |
| macrophage inflammatory protein 1alpha | CCL3 | chemokine | MIP-1alpha/pLD78/P10147 |
| macrophage inflammatory protein 1beta | MIP-1beta/ACT-2/CCL4 | chemokine | P13236 |
| macrophage inflammatory protein 1d | MIP-1d/CCL15/LKN-1 | chemokine | |
| macrophage inflammatory protein 1gamma | MIP-1gamma/CCL9/MIP-3alpha/CCL20/ | chemokine | |
| macrophage inflammatory protein 3alpha | LARC | chemokine | P78556 |
| macrophage inflammatory protein 3beta | MIP-3beta/ELC/CCL19 | chemokine | Q99731 |
| macrophage-derived chemokine | MDC/STCP-1 | chemokine | O00626 |
| monocyte chemoattractant protein-1 | MCP-1/CCL2 | chemokine | P13500 |
| monocyte chemoattractant protein-2 | MCP-2/CCL8 | chemokine | P78388 |
| monocyte chemoattractant protein-3 | MCP-3/CCL7 | chemokine | P80098 |
| monocyte chemoattractant protein-4 | MCP-4/CCL13 | chemokine | Q99616 |
| monocyte chemoattractant protein-5 | MCP-5/CCL12 | chemokine | |
| monokine induced by IFN gamma | MIG | chemokine | Q07325 |
| mucosa-associated chemokine | MEC | chemokine | AF266504 |
| Myeloid progenitor inhibitory factor | MPIF/CKbeta8/CCL23 | chemokine | |
| platelet basic protein | PBP/CTAP-III/NAP-2 | chemokine | P02775 |
| platelet factor 4 | PF-4/CXCL4 | chemokine | P02776 |
| pulmonary activation regulated chemokine | PARC/CCL18/MIP-4 | chemokine | |
| RANTES | CCL5 | chemokine | P13501 |
| secondary lymphoid tissue chemokine | SLC/6Ckine | chemokine | O00585 |
| stromal cell derived factor 1 | SDF-1/CXCL12 | chemokine | P48061 |
| thymus activation regulated chemokine | TARC/CCL17 | chemokine | Q92583 |
| thymus expressed chemokine | TECK/CCL25 | chemokine | O15444 |
| C1q | | collectin | |
| mannose binding lectin | MBL | collectin | |
| surfactant protein A | SP-A | collectin | |
| surfactant protein D | SP-D | collectin | |
| C1 inhibitor | | complement | |
| C3a | | complement | |
| C4b binding protein | C4BP | complement | |
| C5a | | complement | |
| complement C3 | C3 | complement | |
| complement C5 | C5 | complement | |
| complement C8 | C8 | complement | |

TABLE 7-continued

| Protein | Alternate names | Class | Protein ID |
|---|---|---|---|
| complement C9 | C9 | complement | |
| decay accelerating factor | DAF | complement | |
| Factor H | | complement | |
| membrane inhibitor of reactive lysis | MIRL/CD59 | complement | |
| Properdin | | complement | |
| soluble complement receptor 1 | sCR1 | complement | |
| soluble complement receptor 2 | sCR2 | complement | |
| cardiotrophin-1 | CT-1 | cytokine | Q16619 |
| CD27 | | cytokine | P26842 |
| CD27L | CD70 | cytokine | P32970 |
| CD30 | Ki-1 | cytokine | P28908 |
| CD30L | TNFSF8 | cytokine | P32971 |
| CD40L | TRAP/CD154 | cytokine | P29965 |
| interferon alpha | IFNalpha | cytokine | P01562 |
| interferon beta | IFNbeta | cytokine | P01574 |
| interferon gamma | IFNgamma | cytokine | P01579 |
| interferon omega | IFNomega | cytokine | P05000 |
| interferon-sensitive gene 15 | ISG-15 | cytokine | P05161 |
| Leptin | OB | cytokine | P41159 |
| leukemia inhibitory factor | LIF/CNDF | cytokine | P15018 |
| Lymphotoxin | LT/TNF beta | cytokine | P01374 |
| macrophage colony stimulating factor | M-CSF/CSF-1 | cytokine | P09603 |
| macrophage stimulating protein-alpha | MSPalpha/HGF1 | cytokine | P26927 |
| macrophage stimulating protein-beta | MSPbeta/HGF1 | cytokine | P26927 |
| migration inhibition factor | MIF/GIF | cytokine | P14174 |
| oncostatin M | OSM | cytokine | P13725 |
| RANKL | TRANCE/TNFSF-11 | cytokine | O14788 |
| soluble IL6 R complex | sIL6RC (gp130 + sIL6R) | cytokine | |
| soluble Fas ligand | sCD95L | cytokine | P48023 |
| TNF type I receptor | TNF-RI p55 | cytokine | P19438 |
| TNF type II receptor | TNF-R p75 | cytokine | P20333 |
| TNFSF-18 | GITRL/AITRL | cytokine | O95852 |
| tumor necrosis factor alpha | TNF-alpha/Apo3L/DR3-L/ TNFSF-12 | cytokine | P01375 |
| TWEAK | | cytokine | O43508 |
| acidic fibroblast growth factor | aFGF | growth factor | P05230 |
| activin beta A | | growth factor | P08476 |
| agouti related protein | AGRP | growth factor | AAB52240 |
| Amphiregulin | AR/SDGF | growth factor | P15514 |
| angiopoietin-like factor | ALF | growth factor | |
| basic fibroblast growth factor | bFGF | growth factor | P09038 |
| Betacellulin | | growth factor | P35070 |
| bone morphogenic protein 2 | BMP2 | growth factor | P12643 |
| bone morphogenic protein 4 | BMP4 | growth factor | |
| bone morphogenic protein 5 | BMP5 | growth factor | |
| bone morphogenic protein 6 | BMP6 | growth factor | |
| bone morphogenic protein 7 | BMP7 | growth factor | |
| cripto-1 | CRGF | growth factor | |
| epidermal growth factor | EGF | growth factor | P01133 |
| Erythropoietin | Epo | growth factor | |
| fibroblast growth factor 17 | FGF-17 | growth factor | |
| fibroblast growth factor 18 | FGF-18 | growth factor | |
| fibroblast growth factor 19 | FGF-19 | growth factor | |
| fibroblast growth factor 2 | FGF-2 | growth factor | |
| fibroblast growth factor 4 | FGF-4 | growth factor | |
| fibroblast growth factor 6 | FGF-6 | growth factor | |
| fibroblast growth factor 7 | FGF-7/KGF | growth factor | |
| fibroblast growth factor 8 | FGF-8 | growth factor | |
| fibroblast growth factor 9 | FGF-9 | growth factor | |
| Flt3 ligand | Flt L | growth factor | P49771 |
| Follistatin | FSP | growth factor | |
| Granulocyte colony stimulating factor | G-CSF | growth factor | P09919 |
| granulocyte/macrophage CSF | GM-CSF | growth factor | P04141 |
| growth and differentiation factor 11 | GDF-11 | growth factor | |
| growth and differentiation factor 15 | GDF-15 | growth factor | |
| growth arrest specific gene 6 | Gas-6 | growth factor | |
| heparin-binding epidermal growth factor | HB-EGF | growth factor | Q99075. |
| hepatocyte growth factor | HGF/SF | growth factor | P14210 |
| hepatopoietin A | HPTA/HRG alpha/ neuregulin | growth factor | |
| heregulin alpha | NDF/HRG beta/neuregulin/ | growth factor | |
| heregulin beta | NDF | growth factor | |
| IGF binding protein-1 | IGFBP-1 | growth factor | |
| IGF binding protein-2 | IGFBP-2 | growth factor | |
| IGF binding protein-3 | IGFBP-3 | growth factor | |

TABLE 7-continued

| Protein | Alternate names | Class | Protein ID |
|---|---|---|---|
| IGF binding protein-4 | IGFBP-4 | growth factor | |
| inhibin A | | growth factor | |
| inhibin B | | growth factor | |
| insulin-like growth factor IA | IGF-IA | growth factor | P01343 |
| insulin-like growth factor IB | IGF-IB | growth factor | P05019 |
| insulin-like growth factor II | IGF-II | growth factor | P01344 |
| macrophage galatose-specific lectin 1 | MAC-1 | growth factor | |
| Neuritin | | growth factor | |
| Neurturin | | growth factor | |
| orexin A | | growth factor | |
| Osteonectin | SPARC | growth factor | |
| Osteoprotegrin | TNFRSF11B | growth factor | |
| placenta growth factor | PGIF | growth factor | |
| platelet derived growth factor alpha | PDGF-A | growth factor | P04085 |
| platelet derived growth factor beta | PDGF-B | growth factor | P01127 |
| pregnancy zone protein | | growth factor | |
| Prolactin | PRL | growth factor | P01236 |
| sensory and motor neuron-derived factor | SMDF | growth factor | |
| soluble GM-CSF receptor | sGM-CSF R | growth factor | P15509 |
| stem cell factor | SLF/SCF/kit ligand/MGF | growth factor | P21583 |
| Thrombopoietin | TPO/c-MPL ligand | growth factor | P40225 |
| thymic stromal lymphoprotein | TSLP | growth factor | |
| Thymopoietin | Tpo | growth factor | |
| transforming growth factor alpha | TGF-alpha | growth factor | P01135 |
| transforming growth factor beta 1 | TGF-beta1 | growth factor | P01137 |
| transforming growth factor beta 2 | TGF-beta2 | growth factor | P08112 |
| transforming growth factor beta 3 | TGF-beta3 | growth factor | P10600 |
| vascular endothelial growth factor | VEGF | growth factor | P15692 |
| interleukin-1 receptor antagonist | ILiRa | interleukin | P18510 |
| interleukin-10 | IL-10 | interleukin | P22301 |
| interleukin-11 | IL-11 | interleukin | P20809 |
| interleukin-12p35 | IL-12p35 | interleukin | P29459 |
| interleukin-12p40 | IL-12p40 | interleukin | P29460 |
| interleukin-13 | IL-13 | interleukin | P35225 |
| interleukin-14 | IL-14 | interleukin | L15344 |
| interleukin-15 | IL-15 | interleukin | P40933 |
| interleukin-16 | IL-16 | interleukin | Q14005 |
| interleukin-17 | IL-17 | interleukin | Q16552 |
| interleukin-18 | IL-18 | interleukin | Q14116 |
| interleukin-1alpha | IL-1al.pha | interleukin | P01583 |
| interleukin-1beta | IL-1beta | interleukin | P01584 |
| interleukin-2 | IL-2 | interleukin | P01585 |
| interleukin-3 | IL-3 | interleukin | P08700 |
| interleukin-4 | IL-4 | interleukin | P05112 |
| interleukin-5 | IL-5 | interleukin | P05113 |
| interleukin-6 | IL-6 | interleukin | P05231 |
| interleukin-7 | IL-7 | interleukin | P13232 |
| interleukin-9 | IL-9 | interleukin | P15248 |
| soluble interleukin-1 receptor I | sILIR/CD121a | interleukin | P14778 |
| soluble interleukin-1 receptor II | sIL1R/CD121b | interleukin | P27930 |
| soluble interleukin-2 receptor | IL-2R/CD25 | interleukin | P01589 |
| soluble interleukin-5 receptor | sIL-5R/CD125 | interleukin | Q01344 |
| soluble interleukin-6 receptor | sIL-6R/CD126 | interleukin | P08887 |
| soluble interleukin-7 receptor | sIL-7R/CD127 | interleukin | P16871 |
| soluble interleukin-9 receptor | sIL-9R | interleukin | PQ01113 |
| AD7C | NTP | neuronal | AF010144 |
| alpha synuclein | | neuronal | AAH13293 |
| GAP-43 | | neuronal | |
| Neurofilament | | neuronal | |
| Synaptogamin | | neuronal | |
| Synaptophysin | | neuronal | |
| tau P199 | | neuronal | |
| brain derived neurotrophic factor | BDNF | neurotrophin | P23560 |
| ciliary neurotrophic factor | CNTF | neurotrophin | P26441 |
| glial derived neurotrophic factor | GDNF | neurotrophin | P39905 |
| nerve growth factor | NGF | neurotrophin | P01138 |
| neurotrophin 3 | NT-3 | neurotrophin | P20783 |
| neurotrophin 4 | NT-4 | neurotrophin | P34130 |
| soluble CNTF receptor | sCNTFR | neurotrophin | P26992 |
| alpha2-macroglobulin | alpha 2M | others | |
| Alzheimer associated protein | ALZAS | others | |
| amyloid beta protein | Abeta 1-x | others | |
| apolipoprotein A | apoA | others | |
| apolipoprotein B | apoB | others | |
| apolipoprotein D | apoD | others | |

TABLE 7-continued

| Protein | Alternate names | Class | Protein ID |
|---|---|---|---|
| apolipoprotein E | apoE | others | |
| apolipoprotein J | apoD/clusterin | others | |
| C reactive protein | CRP | others | |
| clara cell protein | CC16 | others | |
| glial fibrillary acidic protein | GFAP | others | |
| Melanotransferrin | | others | |
| soluble transferring receptor | TfR | others | |
| Thrombomodulin | | others | |
| Thrombospondin | Tsp | others | |
| tissue transglutaminase | | others | |
| Transferrin | | others | |
| alpha 1-antichymotrypsin | ACT | protease | NP001076 |
| C1r | | protease | |
| C1s | | protease | |
| complement C2 | C2 | protease | |
| Factor B | | protease | |
| Factor D | adipsin | protease | |
| FactorI | | protease | |
| Kallikrein | | protease | |
| MBL-associated serine protease 1 | MASP-1 | protease | |
| MBL-associated serine protease 2 | MASP-2 | protease | |
| Neuroserpin | | protease | AAH18043 |
| secretory leukocyte protease inhibitor | SLPI | protease | |
| Angiogenin | | vascular | |
| Angiostatin | | vascular | P00747 |
| Endostatin | | vascular | |
| Endothelin | | vascular | |
| soluble E selectin | s E selectin | vascular | |
| vascular endothelial growth inhibitor | VEGI | vascular | |

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention.

We claim:

1. A method of aiding diagnosis of Alzheimer's disease ("AD"), comprising comparing normalized measured levels of at least forty-six AD diagnosis biomarkers in a blood sample from a human individual seeking a diagnosis for AD to reference levels for the at least forty-six biomarkers in the blood sample, wherein the human individual has a Mini Mental State Exam (MMSE) score of 14-26, wherein the reference levels are obtained from normalized measured values of the at least forty-six biomarkers from samples in the blood of human individuals without AD, wherein the at least forty-six AD diagnosis biomarkers comprise: GCSF (granulocyte-colony stimulating factor); IFN-g (interferon-gamma); IGFBP-1 (insulin-like growth factor binding protein 1); BMP-6 (bone morphogenetic protein 6); BMP-4 (bone morphogenetic protein 4); Eotaxin-2; IGFBP-2 (insulin-like growth factor binding protein 2); TARC (thymus and activation-regulated chemokine); RANTES; ANG (angiogenin); PARC (pulmonary and activation-regulated chemokine); Acrp30 (adipocyte complement-related protein of 30 kDa); AgRP(ART) (agouti-related protein (agouti-related transcript)); TIMP-1 (tissue inhibitor of metalloproteinase 1); TIMP-2 (tissue inhibitor of metalloproteinase 2); ICAM-1 (intercellular adhesion molecule 1); TRAIL R3 (tumor necrosis factor-related apoptosis-inducing ligand receptor 3); uPAR (urokinase-type plasminogen activator receptor); IGFBP-4 (insulin-like growth factor binding protein 4); LEPTIN(OB); PDGF-BB (platelet-derived growth factor BB); EGF (epidermal growth factor); BDNF (brain-derived neurotrophic factor); NT-3 (neurotrophin 3); NAP-2(neutrophil-activating peptide 2); IL-1ra (interleukin 1 receptor antagonist); MSP-a (macrophage stimulating protein alpha); SCF (stem cell factor); TGF-b3 (transforming growth factor, beta 3); TNF-b (tumor necrosis factor beta); MIP-1d; IL-3 (interleukin 3); FGF-6 (fibroblast growth factor 6); IL-6 R (interleukin-6 receptor); sTNF RII (soluble tumor necrosis factor receptor II); AXL; bFGF (basic fibroblast growth factor); FGF-4 (fibroblast growth factor 4); CNTF (ciliary neurotrophic factor); MCP-1 (monocyte chemoattractant protein 1); MIP-1b (macrophage inflammatory protein-1beta); TPO (thrombopoietin); VEGF-B (vascular endothelial growth factor B); IL-8 (interleukin 8); FAS; and EGF-R (epidermal growth factor receptor), whereby the diagnosis of AD is aided by determining a difference between the normalized measured levels of the at least forty-six AD diagnosis biomarkers to the reference levels of the at least forty-six biomarkers from non-AD samples wherein the difference meets or exceeds a statistically significant difference between normalized measured values of the at least forty-six AD diagnosis biomarkers in the blood samples from individuals without AD and individuals with AD, wherein the statistically significant difference indicates a diagnosis of AD.

2. The method of claim 1, wherein said blood sample is serum or plasma.

3. The method of claim 1, wherein the blood sample is obtained from the human individual immediately prior to measuring the levels of said biomarkers.

4. The method of claim 1, wherein measured values are measured from the blood samples from individuals without AD and individuals with AD.

5. The method of claim 1, wherein the reference levels for the at least forty-six biomarkers are obtained by a method comprising: determining normalized measured levels of the at least forty-six biomarkers in normal individuals with a Mini Mental State Examination (MMSE) score greater than 25, having a statistically significant difference from normalized measured levels of the at least forty-six biomarkers in AD subjects with MMSE score of 25 and below.

6. The method of claim 1, wherein the statistically significant difference in normalized measured values of the at least forty-six AD diagnosis biomarkers in blood samples from individuals with AD relative to samples from individuals without AD is determined by a method comprising Significance Analysis of Microarrays (SAM).

7. The method of claim 6, wherein the statistically significant difference in normalized measured values of the at least forty-six AD diagnosis biomarkers determined by SAM has a q-value range from about 0.0001 to about 0.05.

8. The method of claim 1, wherein the statistically significant difference in normalized measured values of the at least forty-six AD diagnosis biomarkers in blood samples from individuals with AD relative to samples from individuals without AD is determined by a method comprising a t test.

9. The method of claim 8, wherein the statistically significant difference is measured in terms of a p-value or a q-value.

10. The method of claim 9, wherein the statistically significant difference is measured in terms of a p-value, and wherein the p-value is less than about 0.0403.

11. The method of claim 1, wherein the normalized measured values are normalized relative to median values determined contemporaneously using a pool of samples from individuals with AD and individuals without AD which includes the sample from the individual.

12. The method of claim 1, wherein comparing the measured levels comprises a method selected from the group consisting of Significance Analysis of Microarrays, Tree Harvesting, CART, MARS, Self Organizing Maps, Frequent Item Set, and Bayesian networks.

13. The method of claim 1, wherein the aiding the diagnosis of AD further comprises clinical diagnostic methods comprising taking patient histories, administering memory tests, attributing a MMSE score, administering psychological tests, or ruling out temporary or permanent conditions that may explain memory loss.

14. The method of claim 1, wherein determining the statistically significant difference associated with a diagnosis of AD comprises:
   determining a mean value of normalized measured values of each of the at least forty-six AD diagnosis biomarkers in the blood samples from a group of individuals with AD;
   determining a mean value of normalized measured values of each of the at least forty-six AD diagnosis biomarkers in the blood samples from a group of individuals without AD; and
   finding a statistically significant difference between the mean values of the normalized measured values of the at least forty-six AD diagnosis biomarkers in the blood samples between the two groups.

15. The method of claim 14, wherein the group of individuals with AD and group of individuals without AD are age-matched populations.

16. The method of claim 1, wherein determining the statistically significant difference associated with progression of AD comprises:
   determining a mean value of normalized measured values of each of the at least forty-six AD diagnosis biomarkers in the blood samples from a group of individuals with AD;
   determining a mean value of normalized measured values of each of the at least forty-six AD diagnosis biomarkers in the blood samples from a group of individuals without AD; and
   finding a statistically significant difference between the mean values of the normalized measured values of the at least forty-six AD diagnosis biomarkers in the blood samples between the two groups.

17. The method of claim 16, wherein the group of individuals with AD and group of individuals without AD are age-matched populations.

* * * * *